US006221376B1

(12) United States Patent
Lin et al.

(10) Patent No.: US 6,221,376 B1
(45) Date of Patent: *Apr. 24, 2001

(54) GLIAL CELL LINE-DERIVED NEUROTROPHIC FACTOR

(75) Inventors: Leu-Fen H. Lin, Cambridge, MA (US); Franklin D. Collins, Bellvue, WA (US); Daniel H. Doherty, Boulder, CO (US); Jack Lile; Susan Bektesh, both of Boulder, CO (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/935,268

(22) Filed: Sep. 22, 1997

Related U.S. Application Data

(62) Continuation of application No. 08/453,176, filed on May 30, 1995, now Pat. No. 6,015,572, which is a division of application No. 08/182,183, filed as application No. PCT/US92/07888 on Sep. 17, 1992, which is a continuation-in-part of application No. 07/855,413, filed on Mar. 19, 1992, now abandoned, which is a continuation-in-part of application No. 07/788,423, filed on Nov. 6, 1991, now abandoned, which is a continuation-in-part of application No. 07/774,109, filed on Oct. 8, 1991, now abandoned, which is a continuation-in-part of application No. 07/764,685, filed on Sep. 20, 1991, now abandoned.

(51) Int. Cl.$^7$ ................... A61F 2/00; A61K 9/00; C12N 11/04
(52) U.S. Cl. .............. 424/424; 435/182; 514/12; 604/891.1
(58) Field of Search ................ 424/422, 423, 424/424, 486, 489, 491, 499; 530/350, 399; 514/2, 12, 21; 604/891.1; 935/66; 435/182

(56) References Cited

U.S. PATENT DOCUMENTS

| | | |
|---|---|---|
| 4,518,526 | 5/1985 | Olson . |
| 4,742,003 | 5/1988 | Derynck et al. . |
| 4,886,747 | 12/1989 | Derynck et al. . |
| 4,892,538 | 1/1990 | Aebischer et al. . |
| 5,011,472 | 4/1991 | Aebischer et al. . |
| 5,017,735 | 5/1991 | Fellmann et al. . |
| 5,106,627 | 4/1992 | Aebischer et al. . |
| 5,158,881 | 10/1992 | Aebischer et al. . |
| 5,215,969 | 6/1993 | Springer et al. . |
| 5,250,414 | 10/1993 | Schwab et al. . |
| 5,276,145 | 1/1994 | Bottenstein . |
| 5,283,187 | 2/1994 | Aebischer et al. . |
| 5,284,761 | 2/1994 | Aebischer et al. . |

FOREIGN PATENT DOCUMENTS

| | | |
|---|---|---|
| 0233838 | 1/1987 | (EP) . |
| WO 90/05191 | 5/1990 | (WO) . |
| WO 91/01739 | 2/1991 | (WO) . |
| WO 91/02003 | 2/1991 | (WO) . |
| WO 91/10425 | 7/1991 | (WO) . |
| WO 91/10470 | 7/1991 | (WO) . |

OTHER PUBLICATIONS

Aebischer et al. (1991), 'Long–Term Cross–Species Brain Transplantation of a Polymer–Encapsulated Dopamine–Secreting Cell Line', *Exper. Neurol.*, 111:269–275.

Beltz et al. (1983), 'Isolation of Multigene Families and Determination of Homologies by Filter Hybridization Methods', *Methods in Enzymology*, 100:266–285.

Engele et al. (1989), The Development of Mesencephalic Dopaminergic Neurons in Vitro is Affected by Neurotrophic Activities Derived from Neural Cell Lines, *Soc. Neurosci. Abs.*, 15:277.

Collins (1978), 'Axon Initiation by Ciliary Neurons in Culture', *Develop. Biol.*, 65:50–57.

Dayhoff, in Atlas of Protein Sequence and Structure vol. 5, p. 124 (1972), National Biochemical Research Foundation, Washington, D.C.

Friedman et al. (1987), 'The toxicity of MPTP to dopamine neurons in culture is reduced at high concentrations', *Neuroscience Letters*, 79:65–72.

Heikkila et al. (1984), 'Behavioral Properties of GBR 12909, GBR 13069 and GBR 13098: Specific Inhibitors of Dopamine Uptake', *Euro J. Pharmacol.*, 103:241–248.

Hofer and Barde (1988), 'Brain–derived neurotrophic factor prevents neuronal death in vivo', *Nature*, 331 :261.

Kozak (1987), 'An analysis of 5'–noncoding sequences from 699 vertebrate messenger RNAs', *Nucleic Acids Res.*, 15:125–48.

Leibrock et al. (1989), 'Molecular cloning and expression of brain–derived neurotropic factor', *Nature*, 341 :149–152.

Lin et al. (1989), 'Purification, Cloning, and Expression of Ciliary Neurotrophic Factor (CNTF)', *Science*, 246 :1023.

Lo et al. (1990), 'A Striatal–Derived Neurotrophic Factor (NTF): Relationship to Parkinson's Disease (PD)', *Soc. Neurosci. Abstr.*, 16:809.

Maisonpierre et al. (1990), 'Neurotrophin–3: A Neurotrophic Factor Related to NGF and BDNF', *Science*, 247 :1446–1451.

Manthorpe et al. (1986), An Automated Colorimetric Microassay for Neuronotrophic Factors, *Develop. Brain Res.*, 25:191–198.

(List continued on next page.)

Primary Examiner—Gary L. Kunz
Assistant Examiner—Stephen Gucker
(74) Attorney, Agent, or Firm—Daniel R. Curry; Ron K. Levy; Steven M. Odre

(57) ABSTRACT

A novel neurotrophic factor referred to as glial cell line-derived neurotrophic factor (GDNF) has been identified. Genes encoding GDNF have been cloned and sequenced. Methods and devices are disclosed for the delivery of GDNF using either an implantable cell which expresses human GDNF or a biocompatible semipermeable membrane containing genetically engineered cells which express and secrete the neurotrophic factor.

20 Claims, 31 Drawing Sheets

OTHER PUBLICATIONS

Nijima et al. (1990), 'Enhanced survival of cultured dopamine neurons by treatment with soluble extracts from chemically deafferentiated striatum of adult rat brain', *Brain Res.*, 528:151–154.

Schubert et al. (1974), 'Clonal cell lines from the rat central nervous system', *Nature*, 249:224–227.

Thoenen and Edgar (1985), 'Neurotrophic Factors', *Science*, 229 :238–242.

Tresco et al. (1992), 'Polymer Encapsulated Neurotransmitter Secreting Cells', *ASAIO*, 38:17–23.

Varon and Bunge (1979), 'Trophic Mechanisms in the Peripheral Nervous System', *Ann. Rev. Neuroscience*, 1:327–361.

Williams, et al. (1986), 'Continuous infusion of nerve growth factor prevents basal forebrain neuronal death after fimbria fornix transection', *Proc. Natl. Acad. Sci. USA*, 83:9231.

Winn et al. (1991), 'Behavioral Recovery following Intrastriatal Implantation of Microencapsulated PC12 Cells', *Exper. Neurol.*, 113:322–329.

Wurm, Florian M. (1990), 'Integration, Amplification and Stability of Plasmid Sequences in CHO Cell Cultures', *Biologicals*, 18:159–164.

Bakhit et al. (1991) Brain Res. 560:76.

Burt (1992) Biochem. and Biohphys. Res. Comm. 184:590.

Creighton et al. (1984) Proteins: Structure & Molecular Properties (Freeman Co., New York) 39–41.

Edgar et al. (1979) Experimental Cell Res. 121:353.

Engele et al. (1989) Soc. Neuroscience Abstract 15:277.

Gentry et al. (1989) Growth Inhibitory and Cytotoxic Polypeptides 143:154.

Guenther et al. (1985) EMBO J. 4:1963.

Houlgatte et al. (1989) J. Neuroscience Res. 24:143.

Ito et al. (1986) Brain Res. 374:335.

Kaisho et al. (1990) Febs Letters 266:187.

Kim et al. (1991) The International J. Biochem. 23:1307.

Kimura et al. (1990) Nature 348:257.

Lin et al. (1993) Science 260:1131.

Lin et al. (1993) Soc. Neuroscience Abstracts 19:651.

Norrgren et al. (1980) Exp. Cell Res. 130:31.

Purchio et al. (1987) Gene 60:175.

Selingfreund et al. (1991) Proc. Natl. Acad. Sci. USA 88:3554.

Sofer and Britton (1983) Biotechniques 1:198.

Ullrich et al. (1983) Nature 303:821.

Watson et al. (1987) in *Molecular Biology of the Gene*, 4th ed., (eds.) Benjamin Cummings Publishing Co. Amenlo Park, CA, p. 607.

FIG.8

(Ser)-Pro-Asp-Lys-Gln-Ala-Ala-Ala-Leu-Pro-Arg-Arg-Arg-Glu-
(Arg)-Asn-( )*-Gln-Ala-Ala-Ala-Ala-(Ser)-Pro-(Asp)-(Asn)

FIG.12

Asp-(Lys/Gln)-Ile-Leu-Lys-Asn-Leu-(Gly)*-(Arg)-(Val)-(Arg)-(Arg)-Leu

FIG.13A

```
                                                   1                                              34
CCCCCGGGCT GCAGGAATTC GGGG GTC TAC GGA GAC CGG ATC CGA GGT GCC GCC
                              V   Y   G   D   R   I   R   G   A   A

88
GGA CGG GAC TCT AAG ATG AAG TTA TGG GAT GTC GTG GCT GTC TGC CTG GTG TTG
 G   R   D   S   K   M   *   L   W   D   V   V   A   V   C   L   V   L

142
CTC CAC ACC GCG TCT GCC TTC CCG CTG CCC GCC GGT AAG CTT CTC GAA GCG
 L   H   T   A   S   A   F   P   L   P   A   G   K   L   L   E   A

196
CCC GCC GAA GAC CAC TCC CTC GGC CAC CGC CGC GTG CCC TTC GCG CTG ACC AGT
 P   A   E   D   H   S   L   G   H   R   R   V   P   F   A   L   T   S

250
GAC TCC AAT ATG CCC GAA GAT TAT CCT GAC CAG TTT GAT GAC GTC ATG GAT TTT
 D   S   N   M   P   E   D   Y   P   D   Q   F   D   D   V   M   D   F

304
ATT CAA GCC ACC ATC AAA AGA CTG AAA AGG TCA CCA GAT AAA CAA GCG GCG GCA
 I   Q   A   T   I   K   R   L   K   R   S   P   D   K   Q   A   A   A

358
CTT CCT CGA AGA GAG AGG AAC CGG CAA GCT GCA GCT GCC AGC CCA GAG AAT TCC
 L   P   R   R   E   R   N   R   Q   A   A   A   A   S   P   E   N   S
```

```
AGA GGG AAA GGT CGC AGA GGC CAG AGG GGC AAA AAT CGG GGG TGC GTC TTA ACT
 R   G   K   G   R   R   G   Q   R   G   K   N   R   G   C   V   L   T  412

GCA ATA CAC TTA AAT GTC ACT GAC TTG GGT TTG GGC TAC GAA ACC AAG GAG GAA
 A   I   H   L   N   V   T   D   L   G   L   G   Y   E   T   K   E   E  466

CTG ATC TTT CGA TAT TGT AGC GGT TCC TGT GAA GCG GCC GAG ACA ATG TAC GAC
 L   I   F   R   Y   C   S   G   S   C   E   A   A   E   T   M   Y   D  520

AAA ATA CTA AAA AAT CTG TCT CGA AGT AGA AGG CTA ACA AGT GAC AAG GTA GGC
 K   I   L   K   N   L   S   R   S   R   R   L   T   S   D   K   V   G  574

CAG GCA TGT TGT AGG CCG GTC GCC TTC GAC GAC GAC CTG TCG TTT TTA GAC GAC
 Q   A   C   C   R   P   V   A   F   D   D   D   L   S   F   L   D   D  628

AGC CTG GTT TAC CAT ATC CTA AGA AAG CAT TCC GCT AAA CGG TGT GGA TGT ATC
 S   L   V   Y   H   I   L   R   K   H   S   A   K   R   C   G   C   I  682

>
TGA CCCTGGCTCC AGAGACTGCT GTGTATTGCA TTCCTGCTAC AGTGGGAAGA AAGGACCAA    745

GGTTCCAGG AAATATTTGC CCAGAAAGGA AGATAAGGAC CAAGAAGGCA GAGGCAGAGG CGGAAGAAGA    815

AGAAGAAAAG AAGGACGAAG GCAGCCATCT GTGGGAGCCT GTAGAAGGAG GCCCAGCTAC AG    875
```

```
                                                                    >1                                                      68
     atttctctttcttttgaacag CA  AAT ATG CCA GAG GAT TAT CCT GAT CAG TTC GAT GAT GTC ATG
                               N   M   P   E   D   Y   P   D   Q   F   D   D   V   M 131
     GAT TTT ATT CAA GCC ACC ATT AAA AGA CTG AAA AGG TCA CCA GAT AAA CAA ATG GCA GTG CTT
     D   F   I   Q   A   T   I   K   R   L   K   R   S   P   D   K   Q   M   A   V   L 194
     CCT AGA AGA GAG CGG AAT CGG CAG GCT GCA AAC CCA GAG AAT TCC AGA GGA AAA GGT
     P   R   R   E   R   N   R   Q   A   A   N   P   E   N   S   R   G   K   G 257
     CGG AGA GGC CAG AGG GGC AAA AAC CGG GGT TGT GTC TTA ACT GCA ATA CAT TTA AAT GTC ACT
     R   R   G   Q   R   G   K   N   R   G   C   V   L   T   A   I   H   L   N   V   T 320
     GAC TTG GGT CTT GGC TAT GAA ACC AAG GAG GAA CTG ATT TTT AGG TAC TGC AGC GGC TGC
     D   L   G   L   G   Y   E   T   K   E   E   L   I   F   R   Y   C   S   G   C 383
     GAT GCA GCT GAG ACA ACG TAC GAC AAA ATA TTG AAA AAC TTA TCC AGA AAT AGA AGG CTG GTG
     D   A   A   E   T   T   Y   D   K   I   L   K   N   L   S   R   N   R   R   L   V 446
     AGT GAC AAA GTA GGG CAG GCA TGT TGC AGA CCC ATC GCC TTT GAT GAC CTG TCG TTT TTA
     S   D   K   V   G   Q   A   C   C   R   P   I   A   F   D   D   L   S   F   L
```

FIG. 19B

```
GAT GAT AAC CTG GTT TAC CAT ATT CTA AGA AAG CAT TCC GCT AAA AGG TGT GGA TGT ATC TGA    509
 D   D   N   L   V   Y   H   I   L   R   K   H   S   A   K   R   C   G   C   I ctccggctccagagactgctgtgtattgcattcctgctacagtgcaaagaaag                                  562
```

FIG. 22

```
                                                           43
ttctctccccactcccgcctgcccgcgca gGT GCC GCC GCC
                                   G   A   A   A
                                                           97
GGA CGG GAC TTT AAG ATG AAG TTA TGG GAT GTC GTG GCT GTC GTG CTG
 G   R   D   F   K   M   K   L   W   D   V   V   A   V   V   L
         *
                                                           151
CTC CAC ACC GCG TCC GCC TTC CCG CTG CCC GCC GGT AAG AGG CCT CCC GAG GCG
 L   H   T   A   S   A   F   P   L   P   A   G   K   R   P   P   E   A
                                                           205
CCC GCC GAA GAC CGC TCC CTC GGC CGC CGC GCG CCC TTC GCG CTG AGC AGT
 P   A   E   D   R   S   L   G   R   R   A   P   F   A   L   S   S
         223
GAC Tgtaagaaccgttcc
 D
```

GLIAL CELL LINE-DERIVED NEUROTROPHIC FACTOR

The present application is a continuation of U.S. application Ser. No. 08/453,176, filed May 30, 1995 now U.S. Pat. No. 6,015,572; which is a divisional of U.S. application Ser. No. 08/182,183, filed May 23, 1994; which is a 371 of PCT/US92/07888, filed Sep. 17, 1992; which is a continuation-in-part of U.S. application Ser. No. 07/855,413, filed Mar. 19, 1992, now abandoned; which is a continuation-in-part of U.S. application Ser. No. 07/788,423, filed Nov. 6, 1991, now abandoned; which is a continuation-in-part of U.S. application Ser. No. 07/774,109, filed Oct. 8, 1991, now abandoned; which is a continuation-in-part of U.S. application Ser. No. 07/764,685, filed Sep. 20, 1991, now abandoned.

FIELD OF THE INVENTION

The present invention relates to neurotrophic factors and glial cell line-derived neurotrophic factor (GDNF) in particular. Also included within this invention are processes for purification of GDNF from natural sources and processes for cloning rat and human genes encoding GDNF, as well as the nucleic acid sequence of the rat and human genes that encode GDNF. The GDNF gene has been subcloned into an expression vector, and the vector used to express biologically active GDNF. In addition, this invention includes the use of GDNF for preventing and treating nerve damage and nerve related diseases such as Parkinson's disease.

Antibodies to GDNF are disclosed, as well as methods for identifying members of the GDNF family of neurotrophic factors. And finally, methods are described for preventing or treating nerve damage by implanting into patients cells that secrete GDNF.

BACKGROUND OF THE INVENTION

Neurotrophic factors are natural proteins, found in the nervous system or in non-nerve tissues innervated by the nervous system, whose function is to promote the survival and maintain the phenotypic differentiation of nerve and/or glial cells (Varon and Bunge 1979 *Ann. Rev. Neuroscience* 1:327; Thoenen and Edgar 1985 *Science* 229:238). Because of this physiological role, neurotrophic factors may be useful in treating the degeneration of nerve cells and loss of differentiated function that occurs in a variety of neurodegenerative diseases.

In order for a particular neurotrophic factor to be potentially useful in treating nerve damage, the class or classes of damaged nerve cells must be responsive to the factor. Different neurotrophic factors typically affect distinctly different classes of nerve cells. Therefore, it is advisable to have on hand a variety of different neurotrophic factors to treat each of the classes of damaged neurons that may occur with different forms of disease or injury.

Neurotrophic factors can protect responsive neurons against a variety of unrelated insults. For example, the neurotrophic factor nerve growth factor (NGF) will rescue a significant portion of sensory neurons from death caused by cutting their axonal processes (Rich et al. 1987 *J. Neurocytol* 16:261; Otto et al. 1987 *J. Neurosci* 83:156), from ontogenetic death during embryonic development (Hamburger et al. 1984 *J. Neurosci* 4:767), and from damage caused by administration of taxol or cisplatin (Apfel et al. 1991 *Ann Neurol.* 29: 87). This apparent generality of protection has lead to the concept that if a neurotrophic factor protects responsive neurons against experimental damage, it may be useful in treating diseases that involve damage to those neurons in patients, even though the etiology may be unknown.

A given neurotrophic factor, in addition to having the correct neuronal specificity, must be available in sufficient quantity to be used as a pharmaceutical treatment. Since neurotrophic factors are typically present in vanishingly small amounts in tissues (e.g., Hofer and Bards 1988 *Nature* 331:261; Lin et al. 1989 *Science* 246:1023), it would be inconvenient to prepare pharmaceutical quantities of neurotrophic factors directly from animal tissues. As an alternative, it would be desirable to locate the gene for a neurotrophic factor and use that gene as the basis for establishing a recombinant expression system to produce potentially unlimited amounts of the protein.

The inventors of this application describe a method for screening biological samples for neurotrophic activity on the embryonic precursors of the substantia nigra dopaminergic neurons that degenerate in Parkinson's disease. This bioassay for identifying neurotrophic factors that may be useful in treating Parkinson's disease is based on an assay previously described (Friedman et al. 1987 *Neuro. Sci. Lett.* 79:65–72, specifically incorporated herein by this reference) and implemented with modifications in the present invention. This assay was used to screen various potential sources for neurotrophic activity directed to dopaminergic neurons. The present invention describes the characterization of a new neurotrophic factor that was purified from one such source, the conditioned culture medium from a glioblastoma cell line, B49 (Schubert et al. 1974 *Nature* 249:224–27, specifically incorporated herein by this reference). The conditioned medium from this cell line was previously reported to contain dopaminergic neurotrophic activity (Bohn et al. 1989 *Soc. Neurosci. Abs.* 15:277). In this previous report, the source of the neurotrophic activity was not purified, characterized chemically, or shown to be the consequence of a single agent in the conditioned medium. Nerve damage is caused by conditions that compromise the survival and/or proper function of one or more types of nerve cells. Such nerve damage may occur from a wide variety of different causes, some of which are indicated below.

Nerve damage may occur through physical injury, which causes the degeneration of the axonal processes and/or nerve cell bodies near the site of injury. Nerve damage may also occur because of temporary or permanent cessation of blood flow to parts of the nervous system, as in stroke. Nerve damage may also occur because of intentional or accidental exposure to neurotoxins, such as the cancer and AIDS chemotherapeutic agents cisplatinum and dideoxycytidine (ddC), respectively. Nerve damage may also occur because of chronic metabolic diseases, such as diabetes or renal dysfunction. Nerve damage may also occur because of neurodegenerative diseases such as Parkinson's disease, Alzheimer's disease, and Amyotrophic Lateral Sclerosis (ALS), which result from the degeneration of specific neuronal populations.

This application describes a novel neurotrophic factor. Neurotrophic factors are natural proteins that promote the normal functions of specific nerve cells and/or protect the same cells against a variety of different forms of damage. It is these properties that suggest that GDNF may be useful in treating various forms of nerve damage, including those forms indicated specifically above.

Parkinson's disease is identified by a unique set of symptoms that include rigidity, bradykinesis, seborrhea, festination gait, flexed posture, salivation, and a "pill rolling"

tremor. The disease is encountered in all races throughout the world, and the average age of onset is 60 years.

After years of conflicting theories and controversy, a biochemical basis for Parkinson's disease has emerged as the major cause. (See, e.g., Bergman, 1990 *Drug Store News,* 12:IP19.) Of significant importance to an understanding of Parkinson's disease are the areas of the brain known as the substantia nigra the basal ganglia, and particularly, the corpus striatum. The substantia nigra, a bilaterally paired layer of pigmented gray matter in the mid-brain, is involved with dopamine transmission, while the normal basal ganglia function involves a series of interactions and feedback systems which are associated with the substantia nigra and mediated in part by dopamine, acetylcholine and other substances.

In Parkinson's disease, there is a dysfunction in the dopaminergic activity of the substantia nigra which is caused by neuronal degeneration. This results in a state of dopamine deficiency and a shift in the balance of activity to a cholinergic predominance. Therefore, although there is no increase in the concentration of acetylcholine, the excitatory effects on the central nervous system (i.e., tremors) by this cholinergic mediator overwhelm the inhibiting effects of the depleted dopamine.

The most effective treatment for Parkinson's disease to date is the oral administration of Levodopa. Levodopa penetrates the central nervous system and is enzymatically converted to dopamine in the basal ganglia. It is believed that beneficial effects of Levodopa are, therefore, in increasing the concentration of dopamine in the brain. Unfortunately, neither Levodopa or any of the less commonly utilized medications actually stem the progression of the disease which is caused by the degeneration of dopaminergic neurons.

Other researchers have reported the existence of dopaminergic activity in various biological sources. In PCT publication WO91/01739 of Springer et al., a dopaminergic neurotrophic activity was identified in an extract derived from cells of the peripheral nervous system. The activity identified was not purified, but was attributed to a factor having a molecular weight of less than 10,000 daltons. The factor was isolated from rat sciatic nerve but is apparently not CNTF, which is also found in the nerve (Lin et al. 1989 *Science* 246:1023).

In U.S. Pat. No. 5,017,735 of Appel et al., dopaminergic activity was identified in an extract from caudate-putamen tissue. Again, no factors giving rise to the activity were purified and the apparent molecular weight of the activity containing fractions was relatively small. See also, Niijima et al. 1990 *Brain Res.* 528:151–154 (chemically deafferented striatum of adult rat brain); Lo et al. 1990 *Soc. Neurosci. Abstr.,* 16:809 (striatal-derived neurotrophic factor). In addition, other known neurotrophic factors have also been shown to have dopaminergic activity, e.g., Brain derived neurotrophic factor (BDNF), and acidic and basic Fibroblast Growth Factors.

The GNDF of the present invention was isolated based on its ability to promote the functional activity and survival in cell culture of dopaminergic nerve cells isolated from the rat embryo mesencephalon. These dopaminergic nerve cells are the embryonic precursor of the dopaminergic nerve cells in the adult substantia nigra that degenerate in Parkinson's disease. Therefore, GDNF may be useful in reducing the neuronal degeneration that causes the symptoms of Parkinson's disease.

Furthermore, GDNF may be useful in treating other forms of damage to or improper function of dopaminergic nerve cells in human patients. Such damage or malfunction may occur in schizophrenia and other forms of psychosis. Current treatments for such conditions often require drugs active at dopamine receptors, suggesting that improper function of the dopaminergic neurons innervating these receptor-bearing neuronal populations may be involved in the disease process.

Based on previous experience with other neurotrophic factors, new forms of nerve damage that may be treated with GDNF will emerge as more is learned about the various types of nerve cells that are responsive to this neurotrophic factor. For example, nerve growth factor (NGF) only emerged as a potentially useful treatment for Alzheimer's disease when it was recently discovered that NGF acts as a neurotrophic factor for the basal forebrain cholinergic neurons that degenerate in Alzheimer's disease. (Williams, et al. 1986 *Proc. Natl. Acad. Sci. USA* 83:9231). Methods are provided in the present invention for determining other forms of nerve damage that may be usefully treated with GDNF.

Patrick Aebischer and coworkers have described the use of semipermeable, implantable membrane devices that are useful as means for delivering drugs or medicaments in certain circumstances. For example, they have proposed the encapsulation of cells that secrete neurotransmitter factors, and the implantation of such devices into the brain of patients suffering from Parkinson's Disease. See, U.S. Pat. No. 4,892,538 of Aebischer et al.; U.S. Pat. No. 5,011,472 of Aebischer et al.; U.S. Pat. No. 5,106,627 of Aebisher et al.; PCT Application WO 91/10425; PCT Application WO 91/10470; Winn et al. 1991 *Exper. Neurol.* 113:322–329; Aebischer et al. 1991 *Exper. Neurol.* 111:269–275; and Tresco et al. 1992 *ASAIO* 38:17–23.

SUMMARY OF THE INVENTION

This invention relates to and claims substantially purified glial cell line-derived neurotrophic factor (GDNF). In one embodiment of this invention, substantially purified GDNF is obtained having a specific activity at least about 24,000 times greater than the specific activity of B49 conditioned medium. The substantially purified GDNF has a specific activity of at least about 12,000 TU/µg.

The substantially purified GDNF of the present invention has an apparent molecular weight of about 31–42 kD on non-reducing SDS-PAGE, and about 20–23 kD on reducing SDS-PAGE. The substantially purified GDNF has an amino terminal sequence comprised substantially of the amino acid sequence (SEQ ID NO:1):
(Ser)-Pro-Asp-Lys-Gln-Ala-Ala-Ala-Leu-Pro-Arg-Arg-Glu-(Arg)-Asn-( )-Gln-Ala-Ala-Ala-Ala-(Ser)-Pro-(Asp)-(Asn).

The amino acid sequence of mature and "pre-pro" forms of rat GDNF is as set forth in FIGS. 13 and 14 (SEQ ID NO:3 and SEQ ID NO:4). The amino acid sequence of mature human GDNF is as set forth in the underlined portion of FIG. 19 (SEQ ID NO:6). The amino acid sequence of the pre-pro form of human GDNF is set forth in FIGS. 19 (SEQ ID NO:5) and 22 (SEQ ID NO:8).

One aspect of the invention is a method for obtaining purified GDNF comprising: 1) preparing a serum-free growth conditioned medium of B49 glioblastoma cells; 2) concentrating the conditioned medium; 3) performing heparin sepharose chromatography on the concentrated conditioned medium; 4) performing fast protein liquid chromatography on fractions obtained from said heparin sepharose chromatography; and 5) performing reverse-phase high-performance liquid chromatography on fractions obtained from said fast protein liquid chromatography. In one embodiment, the method of obtaining purified GDNF is further comprised of the steps: 6) subjecting fractions obtained by reverse-phase high performance liquid chromatography to preparative SDS-PAGE; and 7) performing reverse-phase high-performance liquid chromatography on factions obtained by preparative SDS-PAGE.

Also described is the cloning of the rat GDNF gene from a cDNA library prepared from the B49 cell line. The nucleic acid sequence encoding mature and pre-pro rat GDNF is set forth in FIG. 13 (SEQ ID NO:3). The method for obtaining a human gene coding for GDNF is also disclosed. The nucleic acid sequence encoding mature human GDNF is as set forth in FIG. 19 (SEQ ID NO:5). The nucleic acid sequence encoding the first 50 amino acids of the pre-pro segment of human GDNF is as set forth in FIG. 22 (SEQ ID NO:8).

This invention also includes pharmaceutical compositions comprising an effective amount of purified GDNF in a pharmaceutically suitable carrier. Also described is a method for preventing or treating nerve damage which comprises administering to a patient in need thereof a therapeutically affective amount of GDNF. In preferred embodiments, the nerve damage is Parkinson's disease or damaged or improperly functioning dopaminergic nerve cells.

In the preferred embodiment of this invention, GDNF is produced by recombinant DNA methods, utilizing the genes coding for GDNF as described herein. The present invention includes a vector for use in producing biologically active GDNF comprised of expression regulatory elements operatively linked to a nucleic acid sequence coding for mature or pre-pro GDNF, and a host cell transformed by such a vector. Also included is a recombinant DNA method for the production of GDNF comprising: subcloning a DNA sequence coding for GDNF into an expression vector which comprises the regulatory elements needed to express the DNA sequence; transforming a host cell with said expression vector; culturing the host cells under conditions for amplification of the vector and expression of GDNF; and harvesting the GDNF.

A recombinant DNA method is described for the production of GDNF comprising: culturing the host cells of this invention under conditions for amplification of the vector and expression of GDNF; and harvesting the GDNF.

This invention includes substantially purified antibodies that recognize GDNF. Also included is a method for preventing or treating nerve damage which comprises implanting cells that secrete glial cell line-derived neurotrophic factor into the body of patients in need thereof. Finally, the present invention includes a device for preventing or treating nerve damage by implantation into a patient comprising a semipermeable membrane, and a cell that secretes GDNF encapsulated within said membrane and said membrane being permeable to GDNF and impermeable to factors from the patient detrimental to the cells.

DESCRIPTION OF THE DRAWINGS

FIG. 8 (SEQ ID NO:1) describes the amino-terminal amino acid sequence obtained from purified GDNF. The empty parenthesis indicates a position where the amino acid could not be determined using the sequencing technique employed. Where residues are given in parentheses, there was some uncertainty as to the identification of that residue. The complete correct amino-terminal amino acid sequence is shown in FIG. 19 (SEQ ID NO:5) below.

FIG. 12 (SEQ ID NO:2) describes an internal amino acid sequence obtained from purified GDNF.

FIGS. 13A–B (SEQ ID NO:3) depicts the nucleic acid sequence obtained for rat GDNF derived from a B49 cell library cDNA clone λZapII76.1. Also depicted is the inferred amino acid sequence for GDNF. The nucleic acid sequence coding for mature GDNF is underlined. The amino-terminal sequence of the most preferred pre-pro form of GDNF is marked with an *.

FIG. 14 (SEQ ID NO:4) depicts the inferred amino acid sequence of mature GDNF.

FIGS. 19A–B (SEQ ID NO:5) depicts a portion of the nucleic acid sequence obtained for human GDNF, as described in Example 2C below, including the entire portion of the gene encoding for mature human GDNF. Also depicted is the inferred amino acid sequence for mature human GDNF. The amino acid sequence (SEQ ID NO:6) for mature human GDNF is underlined.

FIG. 22 (SEQ ID NO:8) depicts a portion of the nucleic acid sequence obtained for human GDNF, as described in Example 2D below, including the coding sequence of amino acids 1–50 of human pre-pro GDNF. Also depicted is the inferred amino acid sequence for the first 50 amino acids of human pre-pro GDNF. This information, in conjunction with coding sequence information given in FIG. 19, provides the full coding sequence for human pre-pro GDNF, and the inferred amino acid sequence for the human pre-pro GDNF protein.

DETAILED DESCRIPTION OF PREFERRED EMBODIMENTS

Figure 1:
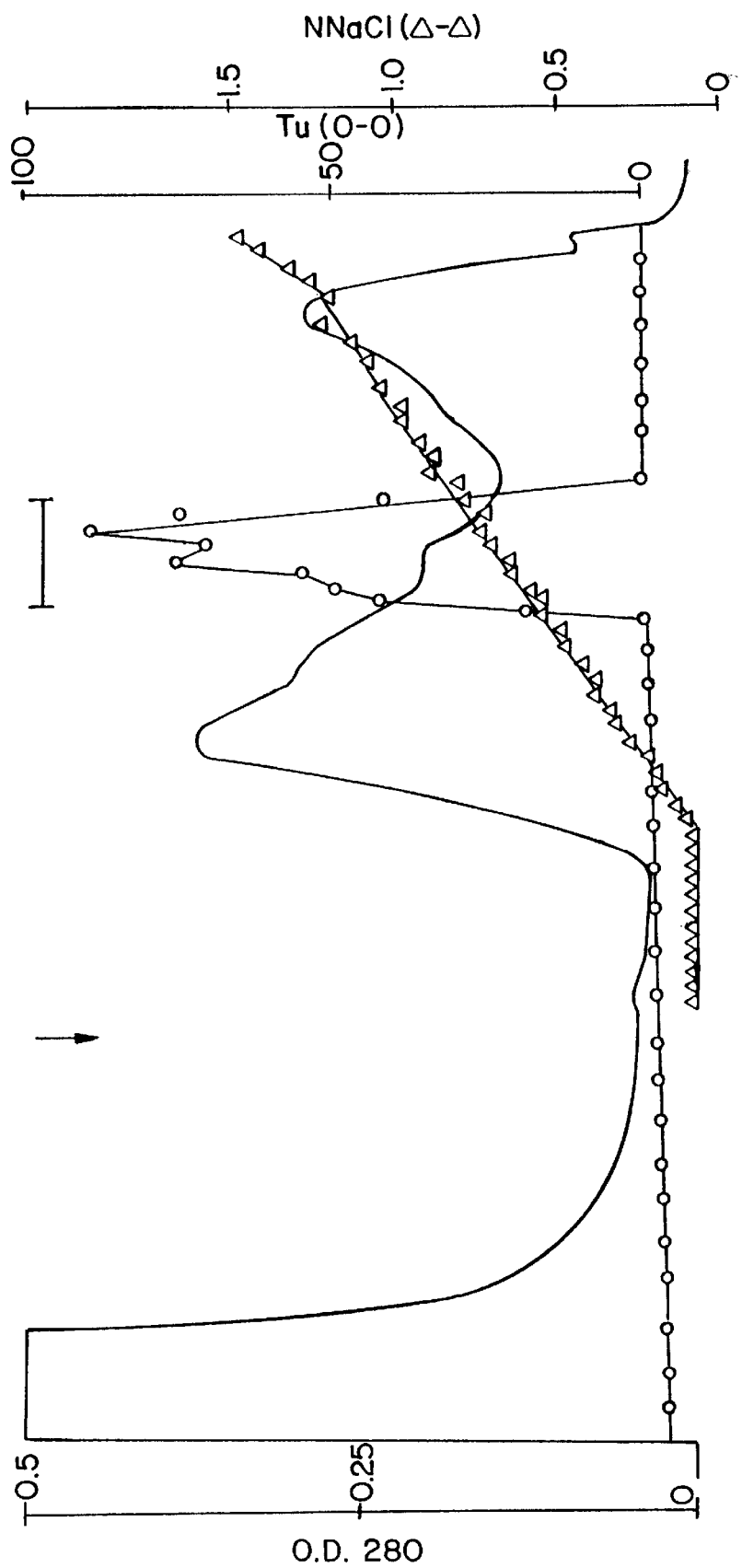
FIG. 1 depicts the results of heparin sepharose chromatography on a solution of concentrated B49 glioblastoma cells serum-free growth conditioned medium. The results show the eluate $O.D._{290}$ (——), conductance (-Δ-), and GDNF activity in TU (-o-). Fractions marked by a bar were pooled for further purification.

Reference will now be made in detail to the presently preferred embodiments of the invention, which, together with the following examples, serve to explain the principles of the invention.

Prior to this invention, GDNF had not been identified as a discrete biologically active substance and had not existed in a substantially pure form. As described herein, a detailed description of GDNF is provided, along with a description of: its physical, chemical and biological characteristics; its utility; how to make it; useful compositions containing it; nucleic acid sequences coding for it; vectors containing such nucleic acid sequences; host cells transformed by such vectors; recombinant techniques for its production; and other aspects of the invention.

GDNF is a protein that may be identified in or obtained from glial cells and that exhibits neurotrophic activity. More specifically, GDNF is a dopaminergic neurotrophic protein that is characterized in part by its ability to increase dopamine uptake on the embryonic precursors of the substantia nigra dopaminergic neurons, and further by its ability to promote the survival of parasympathetic and sympathetic nerve cells. Substantially purified GDNF is further characterized in several ways:

1. It has a specific activity of at least about 12,000 TU/µg.
2. It has a molecular weight on reducing SDS-PAGE of about 20–23 kD.
3. It has a molecular weight on non-reducing SDS-PAGE of about 31–42 kD.
4. It has a specific activity of at least about 24,000 times greater than the specific activity of B49-conditioned medium.
5. It has the ability to upregulate tyrosine hydroxylase immunoreactivity in mesencephalic culture.
6. It has the amino terminal amino acid sequence as shown in FIG. 8 (SEQ ID NO:1).
7. It has the internal amino acid sequence as shown in FIG. 12 (SEQ ID NO:2).

The GDNF of the present invention is more fully described in detail below. It is to be understood that this aspect of the invention covers any dopaminergic neurotrophic protein having an amino terminal amino acid sequence the same or substantially homologous to that given in FIG. 8 (SEQ ID NO:1). This invention also includes any dopaminergic neurotrophic protein having an internal amino acid sequence the same or substantially homologous to that given in FIG. 12 (SEQ ID NO:2).

This invention includes a novel dopaminergic neurotrophic protein that is defined herein as glial-derived neurotrophic factor (GDNF). GDNF has been identified in and isolated from a serum-free growth conditioned medium of B49 glioblastoma cells in a substantially purified form.

GDNF has been purified and characterized, and partial amino acid sequences of the purified material have been obtained. Based on the partial amino acid sequence obtained, DNA probes were designed for obtaining a rat cDNA clone that may be used in the recombinant production of GDNF. The nucleic acid sequence of such clone and the inferred amino acid sequence of rat GDNF is given in FIGS. 13 (SEQ ID NO:3) and 14 (SEQ ID NO:4).

The amino-terminal amino acid sequence of GDNF has been determined, and is shown in FIG. 8 (SEQ ID NO:1). A portion of the internal amino acid sequence of GDNF has also been determined, and is shown in FIG. 12 (SEQ ID NO:2). The purified GDNF has an apparent molecular weight of about 31–42 kD on SDS-PAGE under non-reducing conditions, and about 20–23 kD on SDS-PAGE under reducing conditions. Although not being limited by such theory, it is postulated that this information is consistent with GDNF being a glycosylated, disulfide-bonded dimer in its naturally occurring state.

As described in more detail in Example 6C below, expression of the human GDNF gene in a bacterial expression system leads to the production of recombinant human GDNF or rhGDNF. The material isolated after expression is essentially biologically inactive, and exists as a monomer. Following refolding, GDNF exists as a biologically active disulfide-bonded dimer. GDNF, therefore, is a disulfide-bonded dimer in its natural, biologically active form. This invention, however, includes GDNF in both its monomeric and dimeric, and biologically inactive and biologically active forms.

Probes were prepared based on the nucleic acid sequence of rat GDNF in order to clone the genomic DNA gene coding for human GDNF. The human gene encoding mature GDNF, and the amino acid sequence of human mature GDNF are given in FIG. 19 (SEQ ID NOS:5 and 6).

GDNF may also be characterized by its ability to increase dopamine uptake on the embryonic precursors of the substantia nigra dopaminergic neurons, as described in Example 1 below. GDNF may further be characterized by its ability to promote the survival of parasympathetic and sympathetic nerve cells, as described in Example 4 below.

Figure 24A:
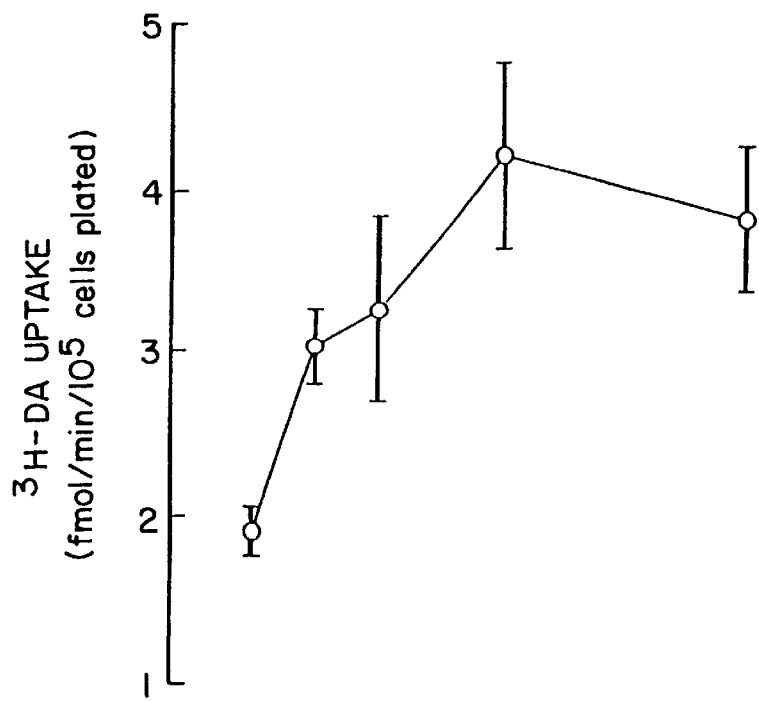
FIGS. 24A–B depicts the specificity of GDNF to dopaminergic neurons. Cultures were prepared as described in Example 1B. GDNF was added on the day of plating, and uptake was measured after 6 days in vitro. A depicts dopamine uptake and B depicts serotonin uptake.
Figure 24B:
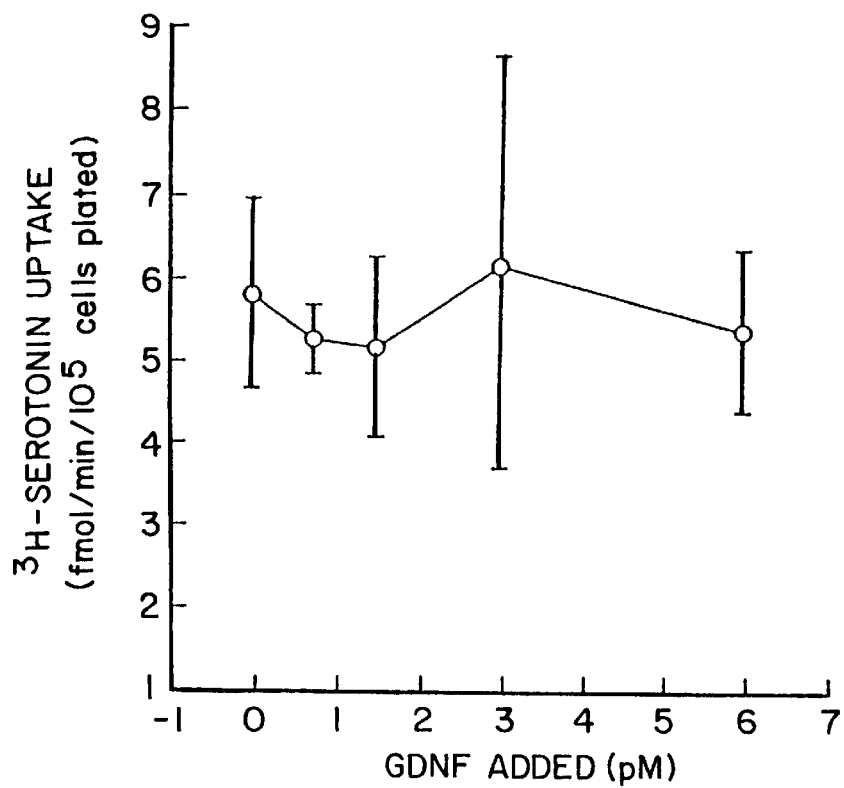

GDNF may be characterized additionally by its ability to upregulate tyrosine hydroxylase inmunoreactivity in mesencephalic cultures. An example of this characteristic is described in Example 1E and shown in FIG. 20. In addition, GDNF has been shown to have some specificity to dopaminergic neurons relative to neurons generally. For example, this was demonstrated by the limited effect on γ-aminobutyric acid (GABA) uptake in neurons containing GABA. This is also described in Example 1E and shown in FIG. 21. GDNF has also been shown to have limited, if any, effect on serotonin uptake in serotonergic neurons. This is described in Example 1E and shown in FIG. 24.

Throughout this specification, any reference to glial cell line-derived neurotrophic factor should be construed to refer to neurotrophic factors of any origin which are substantially homologous to and which are biologically equivalent to the GDNF characterized and described herein. The degree of homology between the rat and human protein is about 93% and all mammalian GDNF will have a similarly high degree of homology. Such GDNFs may exist as diners in their biologically active form.

The present invention encompasses glycosylated and non-glycosylated forms of GDNF as well as truncated forms of the naturally-occurring and recombinant GDNF as described herein. In a further embodiment, GDNF is modified by attachment of one or more polyethylene glycol (PEG) or other repeating polymeric moieties. The present invention also encompasses GDNF recombinantly produced in bacterial expression systems containing an amino-terminal methionine residue.

By "biologically equivalent" as used throughout the specification and claims, we mean compositions of the present invention which are capable of demonstrating some or all of the same neurotrophic properties in a similar fashion, but not necessarily to the same degree as the GDNF isolated from the B49 conditioned medium. By "substantially homologous" as used throughout the ensuing specification and claims, is meant a degree of homology to the GDNF isolated from the B49 conditioned medium in excess of that displayed by any previously reported GDNF. Preferably, the degree of homology is in excess of 70%, most preferably in excess of 80%, and even more preferably in excess of 90%, 95% or 99%. The percentage of homology as described herein is calculated as the percentage of amino acid residues found in the smaller of the two sequences which align with identical amino acid residues in the sequence being compared when four gaps in a length of 100 amino acids may be introduced to assist in that alignment as set forth by Dayhoff, in *Atlas of Protein Sequence and Structure* Vol. 5, p. 124 (1972), National Biochemical Research Foundation, Washington, D.C., specifically incorporated herein by reference. Also included as substantially homologous is any GDNF which may be isolated by virtue of cross-reactivity with antibodies to the GDNF described herein or whose genes may be isolated through hybridization with the gene or with segments of the gene for GDNF described herein.

A preferred GDNF of the present invention has been isolated from B49 conditioned medium and has been isolated in a substantially purified form. An additional preferred GDNF is prepared by recombinant DNA technology to yield GDNF in a substantially purified form. For the purposes of the present application, "pure form" or "substantially purified form," when used to refer to the GDNF disclosed herein, shall mean a preparation which is substantially free of other proteins which are not GDNF. Preferably, the GDNF of the present invention is at least 50% percent pure, preferably 75% pure and more preferably 80%, 95% or 99% pure. In one embodiment of the present invention, the GDNF protein preparation is of such substantially purified form so as to enable one of ordinary skill in the art to determine at least portions of its amino acid sequence without first performing further purification steps.

In a preferred embodiment of this invention, GDNF is purified from B49 conditioned medium as described in Example 1 below. Of course, given the information set forth herein, it will be apparent to those skilled in the art that other sources of GDNF may be identified, and that the purification of GDNF from such sources can be accomplished generally according to the method of purification presented here.

The dopaminergic activity of the GDNF is used to facilitate the purification process. The bioassay for dopaminergic neurotrophic activities is described in Example 1B below. Briefly, cultures of dissociated mesencephalic cells are prepared, either in serum rich or serum free environments. Samples to be tested for dopaminergic activity are desalted and serially added to the cell cultures and the dishes are incubated for 6 days at 37° C. in a humidified atmosphere containing 6.5% $CO_2$. The cultures, in the presence of the testing material, are then incubated at 37° C. with tritiated dopamine ($^3$H-DA). The dopamine uptake is halted, the cells washed, and the dopamine uptake analyzed by scintillation counting of retained tritium in the cultures.

The purification of GDNF is described below in detail in Example 1C. The process of purification is detailed in Table I. The conditioned medium starting material is prepared from B49 glioblastoma cells by placing the cells in serum free medium for 2 days, when the conditioned medium is collected and replenished. This cycle is repeated to yield 3 harvests of conditioned medium from each batch of B49 cells. The conditioned medium is centrifuged and concentrated about 10 fold prior to further purification.

The first step of preparation of this crude mixture defined herein as serum-free growth conditioned medium of B49 glioblastoma, is introducing the conditioned medium onto a Heparin Sepharose column equilibrated with 50 mM NaPi buffers, pH 8.0, containing 0.15 N NaCl. A gradient buffer solution made up of 50 mM NaPi, pH 8.0 containing 1.5 N NaCl is introduced to the column after elution is stabilized. Fractions from this chromatography are measured for GDNF activity, and those fractions containing the GDNF activity are pooled for further purification.

The pooled fractions are subjected to fast protein liquid chromatography (FPLC) on a Superose column, with a solvent buffer of 50 mM NaPi buffer, pH 7.4, containing 0.5 N NaCl. Again, the GDNF activity of fractions obtained is determined. A single fraction from this procedure is then acidified and loaded onto a C-8 reverse phase high performance liquid chromatography (HPLC) column. Fractions identified containing GDNF activity are combined for further purification and for protein sequencing. As shown in Table 1 below, the GDNF obtained at this point has a specific activity about 24,000 fold in excess of conditioned medium. Amino terminal sequencing of the protein obtained at this point gives the amino terminal sequence as shown in FIG. 8 (SEQ ID NO:1).

Figure 6A:
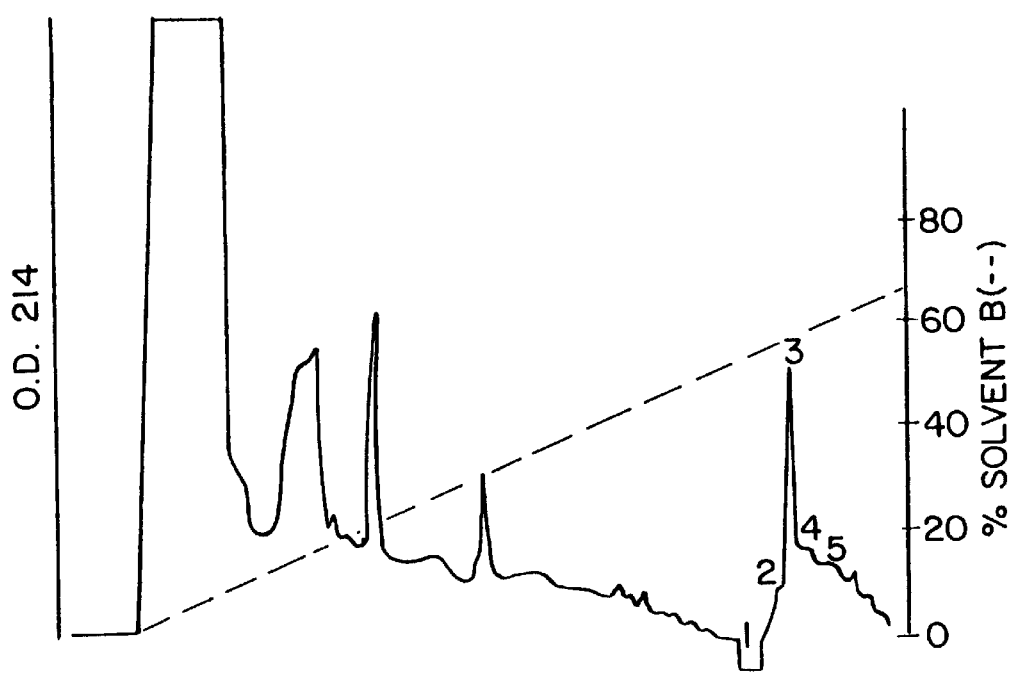
FIGS. 6A–B depicts the results of the RP-HPLC on fractions 16–23 from FIG. 5. Chromatogram A contains the sample, and chromatogram B is a control (pooled gel extract from corresponding slices of a blank lane).
Figure 6B:
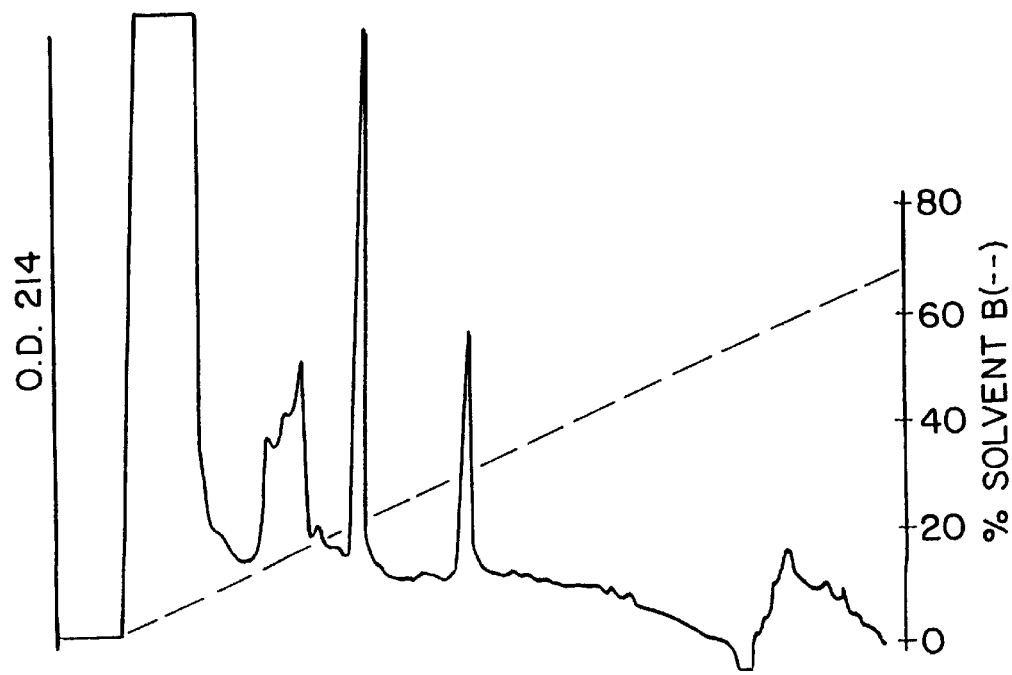

Further purification of the GDNF obtained from HPLC can be accomplished by performing preparative SDS-PAGE on the fractions containing the GDNF activity. Added to the protein containing fractions are buffer containing glycerol and SDS, and the solution is run on non-reduced 15% SDS-PAGE, with electrophoresis conducted at 10° C. at 40 mA/gel for 2 hours. The portion of the gel corresponding to a molecular weight of about 30–42 kD has been found to contain the GDNF activity by bioassay. A second HPLC chromatography of the material isolated from SDS-PAGE yields a single peak of GDNF, as shown in FIG. 6.

TABLE 1

PURIFICATIOH OF GDNF FROM B49 CELL CM

| STEP | | PROTEINS (MG) | BIOACTIVITY (TU × 10$^{-3}$) | SP. ACT (TU/µg) | FOLD | YIELD (%) |
|---|---|---|---|---|---|---|
| CM | | 200 | 94 | 0.5 | (1) | (100) |
| 1. | Heparin Sepharose | 3.1 | 37 | 12 | 24 | 39 |
| 2. | FPLC Superose | 0.3$^a$ | 31 | 103 | 206 | 33 |
| 3. | RP-HPLC | 0.001$^b$ | 12 | 12,000 | 24,000 | 13 |
| 4. | Preparative SDS-PAGE | n.d | 7 | n.d | n.d | 7 |
| 5. | RP-HPLC | 0.0003$^b$ | 5 | 17,000 | 34,000 | 5 |

$^a$based on O.D.$_{280}$
$^b$based on the recovery from protein sequencing (in picamoles) and an assumed molecular weight (from non-reducing SDS-PAGE) OF 36 kD for GDNF.
n.d. = not determined The amino terminal sequences of GDNF were determined for the material from HPLC before and after preparative SDS-PAGE. The procedures utilized for obtaining amino acid sequences of purified GDNF are given in Example 1D. Amino-terminal sequence was obtained with a gas phase protein sequencer. Internal sequences were obtained from the material obtained by HPLC that had not been further purified by preparative SDS-PAGE. Internal amino acid sequence was obtained by incubating the purified GDNF with trypsin. The trypsin fragments obtained were separated by HPLC. One fragment was found to contain the first 13 amino acid residues of the amino-terminal sequence of the untreated protein. A second fragment was treated with CNBr, purified by HPLC, reduced, and again purified on HPLC. The amino acid sequence obtained is shown in FIG. 12 (SEQ ID NO:2). Those sequences given in parentheses were determined to a small degree of confidence.

This invention includes the method for cloning the gene for GDNF, and the gene that was identified that encodes GDNF. A detailed procedure for the cloning of rat and human genes for GDNF is given below in Example 2. Again, those skilled in the art will appreciate that other methods for cloning such a gene are obvious in light of the disclosure herein. In particular, the cloning of genes from other species encoding GDNF will be obvious in view of the disclosures and procedures described herein.

The rat GDNF gene described herein was obtained from a cDNA library constructed from poly A+ RNA isolated from B49 cells, which was screened with a degenerate oligonucleotide probe based on the amino acid sequence obtained from the purified GDNF. The cDNA was obtained according to standard procedures, treated to contain EcoRI-digested linkers, and inserted into the λZap II cloning vector. The hybridization probe used was $^{32}$P-labeled, and consisted of the following degenerate oligonucleotide (SEQ ID NO:7):

```
5' > CCIGATAAACAAGCIGCIGC>3'
          C     G  G
```

Several positive clones were obtained, and one clone (λZapII76.1) was positively identified by DNA sequencing as encoding a portion of GDNF that was not used in designing the degenerate probe.

The procedure for obtaining the nucleotide sequence of the cDNA clone contained in λZapII76.1 is given in Example 2B. below. The nucleotide sequence of the first 877 base pairs of the 5' end of the cDNA clone was determined, and is shown in FIG. 13 (SEQ ID NO:2). In FIG. 13, the clone shown contains an open reading frame (ORF) of 227 amino acids that includes the amino-terminus of purified GDNF and is consistent with the sequence for an internal peptide obtained by cleavage of purified GDNF.

Figure 14:
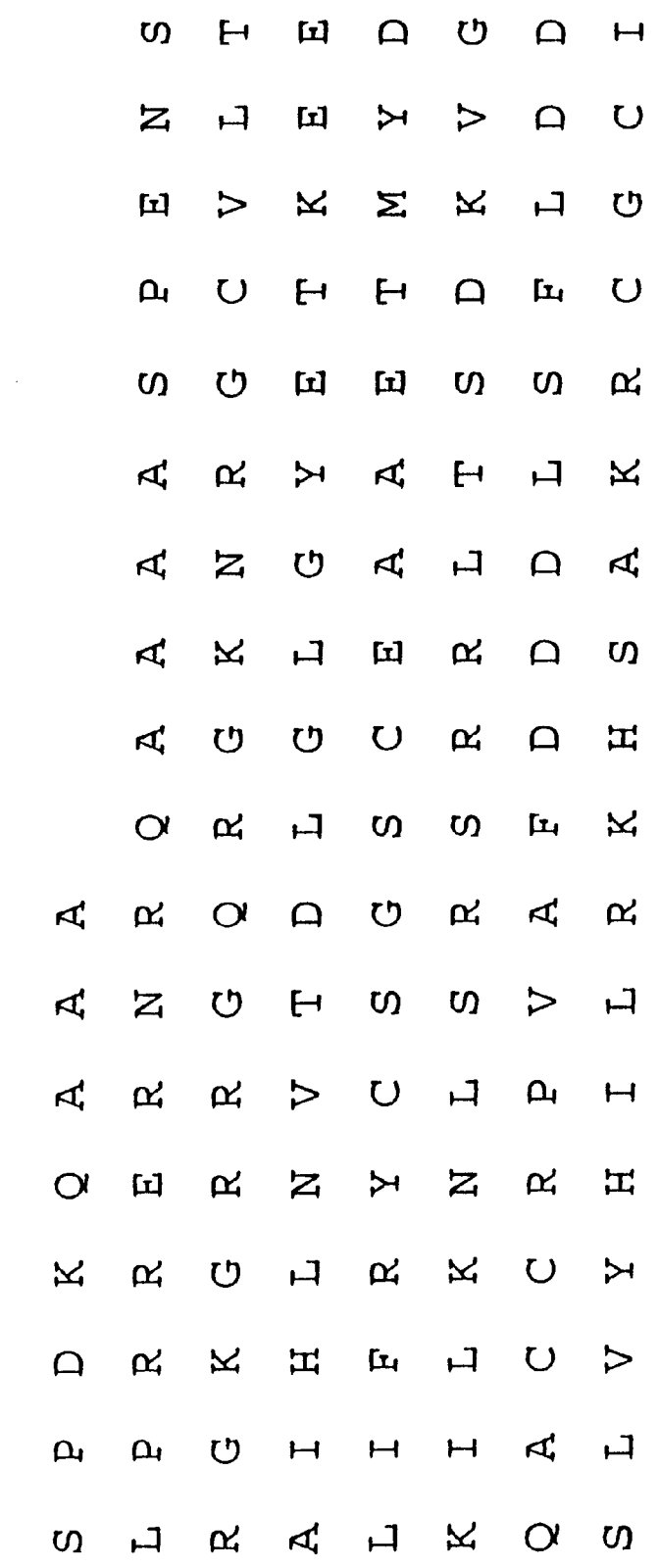

The inferred amino acid sequence given in FIG. 14 (SEQ ID NO:4) shows the amino acid sequence for the "mature GDNF". By. "mature GDNF", is meant the sequence of the purified GDNF obtained from the B49 conditioned medium. Of course, the purified GDNF may exist as a dimer or other multimer and may be glycosylated or chemically modified in other ways. Mature GDNF may be truncated at the carboxyl terminus, in particular by proteolytic processing of the lys-arg residues 6 and 5 residues from the carboxyl terminal end. Examination of the nucleic acid sequence of the λZapII76.1 rat clone as shown in FIG. 13 (SEQ ID NO:2) suggests that GDNF is initially translated as a pre-pro-GDNF polypeptide and that proteolytic processing of the signal sequence and the "pro" portion of this molecule result in purified GDNF having the same mature sequence as that obtained from B49 conditioned medium. It is postulated, that the pre-pro-GDNF polypeptide begins at the first ATG—methionine encoding—codon at the 5' end of the clone (position 50 in FIG. 13). The present invention includes, therefore, any and all pre-pro GDNF polypeptides that may be translated from the gene shown in FIG. 13, as well as any and all pre-pro GDNF polypeptides translated from a more complete clone that may be easily obtained by one of skill in the art using standard laboratory procedures and the clone described herein.

Review of the rat nucleic acid sequence given in FIG. 13 (SEQ ID NO:2) shows that the predicted amino acid sequence located between positions 518 and 538 is Asp-Lys-Ile-Leu-Lys-Asn-Leu which is consistent with the amino acid sequence determined for a peptide derived from purified mature GDNF by the process described in the section on internal sequence in Example 1 below. A TGA stop codon at position 706 terminates the ORF. The predicted length of the purified GDNF is thus 134 amino acid residues, and the predicted molecular weight of this polypeptide is 14,931. Two potential N-linked glycosylation sites occur at positions 425 and 533. Glycosylation at either or both of these sites would increase the molecular weight of the molecule.

The serine residue at position 281, which corresponds to the start of the sequence of purified mature GDNF, is preceded by the sequence Lys-Arg which provides a potential proteolytic cleavage site for processing of a putative precursor form of GDNF to produce the form of the molecule that is purified from B49 cells. A potential translational initiation codon (ATG) occurs at position 50 in the sequence and is closely followed by a potential secretory signal sequence. The sequences flanking this ATG show sufficient similarity to the Kozak consensus sequence (Kozak 1987 *Nucleic Acids Res.* 15:125–48) to indicate that this ATG could be utilized as a translational initiation site. Moreover, this ATG is the most 5' ATG in the sequence of the cDNA clone. These facts suggest it as a potential start site for translation of a precursor form of GDNF.

These above noted features of the nucleotide sequence of the rat cDNA clone suggest the possibility that GDNF is initially translated as a pre-pro-GDNF polypeptide and that proteolytic processing of the signal sequence and the "pro" portion of this molecule result in production of the form of GDNF that is purified from B49 cell conditioned medium. However, the occurrence of other forms of GDNF is also consistent with the sequence data. For example, two other potential ATG translational starts occur within the 681 bp ORF: one at position 206 and one at 242. These ATG'are located upstream of the start of the amino-terminal sequence of purified GDNF. Although, in eukaryotes, translational initiation generally occurs at the 5'-most ATG of the mRNA (Kozak, supra,) there are instances in which a proportion of the translational initiations occur at a downstream ATG. Thus, alternative precursor forms of GDNF could conceivably arise by translational initiation at these ATG codons. Proteolytic processing of these polypeptides could result in production of the same form of purified GDNF observed in B49 cell conditioned medium. Moreover, the open reading frame extends through the 5' end of the sequence of the cDNA clone. It is therefore possible that the initiation of translation occurs at an upstream ATG not present in the cDNA clone. In this eventuality, GDNF would be translated as an even larger precursor containing the amino acid sequence described here and additional sequence upstream. Processing of such a hypothetical precursor form could also lead to production of the purified form of GDNF reported here. It would be possible to detect potential upstream ATG starts by sequencing the 5' end of the mRNA containing the GDNF gene via primer extension with reverse transcriptase (Maniatis et al. supra). Additionally, other cDNA clones could be obtained from B49 libraries and the 5' ends of these clones could be sequenced. The size of the 5' mRNA located upstream of the first ATG could be more roughly determined by the techniques of "S1 mapping" (Maniatis et al. supra) and/or simple sizing of primer extension products of the reverse transcriptase reaction. While a variety of putative forms of the primary translational product that contains the sequences encoding purified GDNF can be postulated, the partial DNA sequence presented here for the cDNA clone carried in the recombinant phage λZapII76.1 clearly defines the coding sequence that constitutes the purified GDNF polypeptide isolated from the B49 cell conditioned medium.

In Example 2C below, the cloning of the human gene that encodes GDNF, is described. A human genomic library was screened with a probe derived from the rat cDNA-clone described in Example 2B. A genomic DNA clone of the human GDNF gene was identified and the sequence of the gene coding for mature human GDNF is given in FIG. 19 (SEQ ID NO:5).

Figure 23:
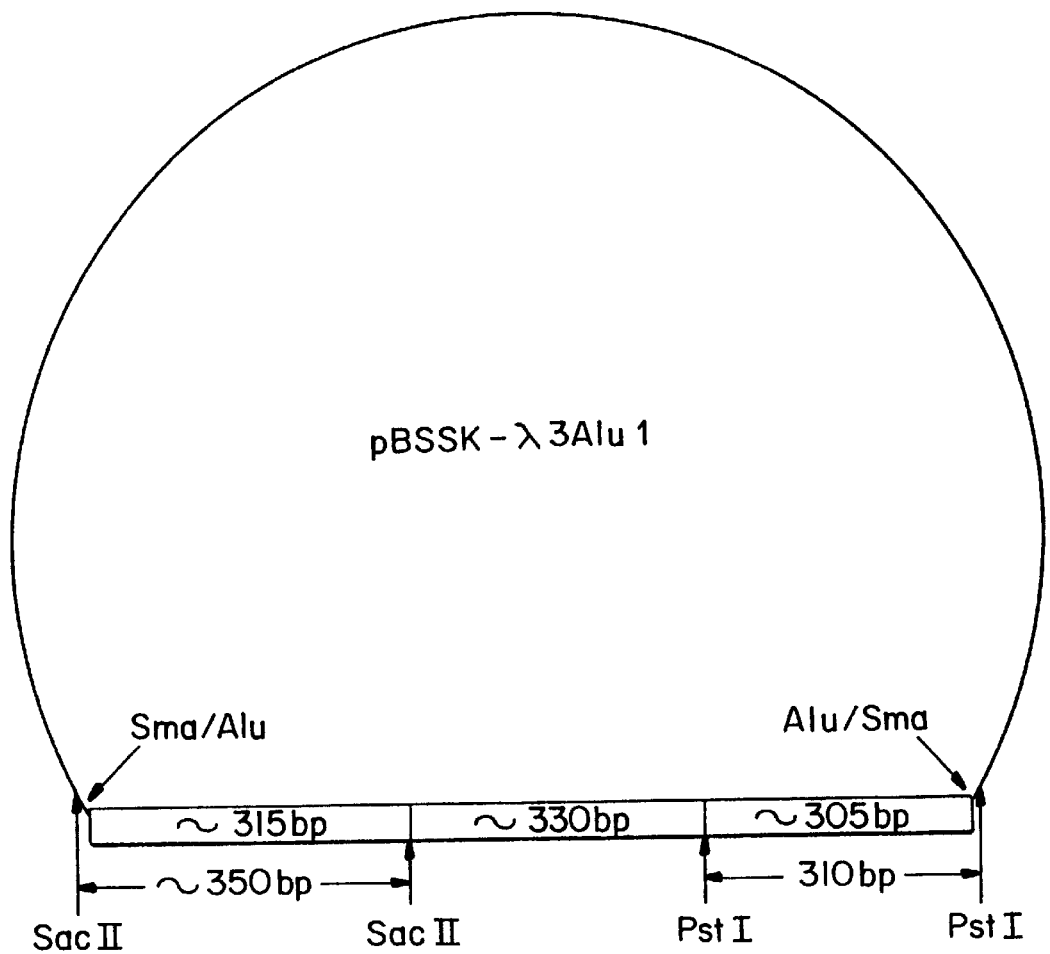
FIG. 23 depicts a map of SacII and PstI sites within the plasmid of pBSSK-λ3AluI, as described in Example 2D below.

The sequence given in FIG. 19 for the gene for human GDNF does not give the entire coding sequence for the pre-pro portion of GDNF. The process for obtaining the coding sequence for the first 50 amino acids of human pre-pro GDNF is described below in Example 2D. The sequence obtained is given in FIG. 22 (SEQ ID NO:8). The map of plasmid pB55K-λ3Alu1 used to obtain the sequence is as shown in FIG. 23.

This invention includes nucleic acid sequences encoding GDNF. Relatively highly homologous sequences coding for rat (FIG. 13) (SEQ ID NO:3) and human (FIG. 19) (SEQ ID NO:5) GDNF are given herein. Also included within the scope of this invention are substantially similar nucleic acid sequences that code for the same or highly homologous amino acid sequences. For example, when preparing a construct for expression of mature GDNF in a bacterial expression system such as *E. coli,* certain codons in the nucleic acid sequence given in FIG. 19 (SEQ ID NO:5) may be substituted with codons more readily expressed in *E. coli* according to well known and standard procedures. Such modified nucleic acid sequences would be included within the scope of this invention.

Specific nucleic acid sequences can be modified by those of skill in the art. Therefore, this invention also includes all nucleic acid sequences which encode for the amino acid sequences for mature rat and mature human GDNF as set forth in FIGS. 14 (SEQ ID NO:4) and 19 (SEQ ID NO:6), and pre-pro rat GDNF as set forth in FIG. 13 (SEQ ID NO:3) and for pre-pro human GDNF as set forth in FIGS. 19 (SEQ ID NO:5) and 22 (SEQ ID NO:8). The present invention also incorporates nucleic acid sequences which will hybridize with all such nucleic acid sequences—or the complements of the nucleic acid sequences where appropriate—and encode for a polypeptide having dopaminergic activity. The present invention also includes nucleic acid sequences which encode for polypeptides that have dopaminergic activity and that are recognized by antibodies that bind to GDNF.

The present invention also encompasses vectors comprising expression regulatory elements operatively linked to any of the nucleic acid sequences included within the scope of the invention. This invention also incorporates host cells—of any variety—that have been transformed with vectors comprising expression regulatory elements operatively linked to any of the nucleic acid sequences included within the scope of this invention.

The expression of GDNF in COS cells is described below in Example 5. The gene encoding GDNF depicted in FIG. 13 was subcloned into the plasmid vector pSG5, a vector designed for the transient expression of cloned gene cells such as COS cells. Plasmids containing the GDNF gene in the proper and improper orientation were selected and the DNA transfected into COS-7 cells. Following cultivation, the transformed cells were harvested. The COS-7 conditioned medium was tested for bioactivity in both the dopaminergic assay and the sympathetic ganglia neuron assay. The conditioned medium from the cells containing the gene for GDNF in the proper orientation was found to have biological activity in both such assays, indicating that biologically active GDNF had been successfully produced via recombinant DNA processes.

In a preferred embodiment of the present invention, human mature GDNF is prepared by recombinant DNA technology in a bacterial expression system.

The expression of human GDNF in *E. coli* is described below in Example 6. The portion of the human GDNF gene that codes for mature human GDNF as shown in FIG. 19, was used to prepare a human GDNF construct. Such construct was ligated into a plasmid vector, which was transformed into *E. coli* strain JM107. After culturing of the transformed host cells, the GDNF produced was harvested. A protein of the expected molecular weight for mature human GDNF (about 15,000 daltons) was obtained, and amino terminal sequencing confirmed that the protein obtained was mature human GDNF.

The refolding and naturation of human GDNF expressed in *E. coli* is described below in Example 6C. In the embodiment of the invention described, the expressed protein-containing extract obtained was partially purified prior to refolding by ion exchange chromatography on S-Sepharose Fast Flow resin. Refolding was accomplished by adding: first dithiothreitol, then glutathione disodium salt, then a refold buffer to the GDNF-containing extract. The refolded rhGDNF was substantially fully biologically active, and existed as a disulfide-bonded dimer in its biologically active form. The GDNF prior to refolding—and after reduction of the refolded material—existed in a monomeric state and was substantially biologically inactive.

GDNF may also be produced by expression in other expression systems. For example, with the nucleic acid sequence coding for mature human GDNF as shown in FIG. 19, one skilled in the art could produce GDNF in other expression systems. Vectors containing the nucleic acid sequence coding for GDNF operatively linked to expression regulatory elements may be transformed into other microorganism host cells including Bacillus, Pseudomonas and yeast. Baculovirus expression systems may also be employed.

As noted above, the present invention relates to methods for treating nerve damage in patients suffering therefrom. These methods comprise the administration of a therapeutically effective amount of a human protein glial-derived neurotrophic factor (GDNF) to a patient suffering from nerve damage.

A disease or medical indication is to be considered to be nerve damage if the survival or function of nerve cells and/or their axonal processes is compromised. In a preferred embodiment, such nerve damage occurs as the result of one of the following conditions: 1) Physical injury, which causes the degeneration of the axonal processes and/or nerve cell bodies near the site of injury; 2) Ischemia, as in stroke; 3) Exposure to neurotoxins, such as the cancer and AIDS chemotherapeutic agents cisplatinum and dideoxycytidine (ddC), respectively; 4) Chronic metabolic diseases, such as diabetes or renal dysfunction; and, 4) Neurodegenerative diseases such as Parkinson's disease, Alzheimer's disease, and Amyotrophic Lateral Sclerosis (ALS), which cause the degeneration of specific neuronal populations. A nonexclusive list of conditions involving nerve damage includes Parkinson's disease, Alzheimer's disease, Amyotrophic Lateral Sclerosis, Stroke, Diabetic Polyneuropathy, Toxic Neuropathy caused by the cancer chemotherapeutic agents taxol or cisplatin or vincristine, Toxic Neuropathy caused by the AIDS chemotherapeutic agents ddI or ddC, and physical damage to the nervous system such as that caused by physical injury of the brain and spinal cord or crush or cut injuries to the arm and hand.

Methods for producing GDNF are also disclosed herein. One disclosed method consists of isolating GDNF from various sources, such as glial cell line conditioned medium. A second method involves isolating the genes responsible for coding GDNF, cloning the gene in suitable vectors and cell types, and expressing the gene in order to produce the GDNF. The latter method, which is exemplary of recombinant DNA methods in general, is a preferred method of the present invention. Recombinant DNA methods are preferred in part because they are capable of achieving comparatively higher amounts of protein at greater purity. Recombinant human GDNF is the most preferred protein for the preparation of therapeutic compositions and for the treatment of nerve damage.

This invention includes means for identifying and cloning genes that encode proteins that share amino acid sequence homology with GDNF, as well as all such identified proteins.

A mammalian gene family comprised of three neurotrophic factors has been described (Leibrock et al. 1989 *Nature* 341:149–152, Maisonpierre et al. 1990 *Science* 247:1446–1451.) The mature forms of the three proteins comprising this family [nerve growth factor (NGF), brain derived neurotrophic factor (BDNF), and neurotrophin-3 (NT-3)] share ~50% amino acid identity with each other. The positions of the six cysteine residues present in each of these proteins are precisely conserved. Although structurally similar, these three proteins display different tissue distributions (Ernfors et al. 1990 *Neuron* 5:511–526, Maisonpierre et al. 1990 *Neuron* 5:501–509, and Phillips et al. 1990 *Science* 250:290–294) and different in vitro activities (Rosenthal et al. 1990 *Neuron* 4:767–773, Whittemore et al. 1987 *Brain Res Rev* 12:439).

GDNF displays no significant homology to any previously described protein but unidentified genes may exist that encode proteins that have substantial amino acid sequence homology to GDNF and which could function in vivo as neurotrophic factors with different tissue specific distribution patterns and/or different spectra of activities. Such proteins would constitute members of the GDNF family of neurotrophic factors. The DNA sequences for the rat and human GDNF genes, presented in FIGS. 13 (SEQ ID NO:3) and 19 (SEQ ID NO:5) and 22 (SEQ ID NO:8) respectively, could be used to identify new members of such a putative "GDNF gene family".

As a consequence of the conservation of amino acid sequence among the protein products of the members of a gene family such as the "NGF gene family" noted above or the "GDNF gene family," there is considerable conservation of sequence at the DNA level. Therefore, under appropriate hybridization conditions, nucleic acid "cross-hybridization" can occur between genes within the family, i.e., a nucleic acid probe derived from the sequence of one of the family members will form a stable hybrid duplex molecule with nucleic acid molecules from different members of the family which have sequences related, but not identical, to the probe (Beltz et al. 1983 *Methods in Enzymology* 100:266–285). Therefore, one may screen for genes related by sequence homology to GDNF by preparing unique or degenerate DNA (or RNA) probes based on the sequence of GDNF from the rat, human or any other species and performing hybridization experiments with a variety of target DNAs (or RNAs) under conditions that will allow stable formation of imperfectly paired nucleic acid duplexes.

Such hybridization conditions, often termed "reduced stringency" are well described in the literature (Beltz et al. supra, Sambrook et al. 1989 *Molecular Cloning,* 2nd edition, Cold Spring Harbor Press) and most frequently involve reduction in temperature of the hybridization reaction when carried out in aqueous solution and/or reduction in concentration of formamide in hybridization systems normally employing solutions containing 50% formamide. Other means of reducing hybridization stringency have also been described and could be employed (Sambrook et al., supra).

The nucleic acid targets in these hybridization experiments could include:

1) genomic DNA libraries containing human, rat, or any mammalian species, or any other species DNA cloned into any convenient vector including bacteriophages, plasmids, cosmids, yeast artificial chromosomes, or any other type of vector;

2) cDNA libraries generated from RNA from any tissue type obtained from any of the above noted organisms or obtained from culture of any type of primary cell obtained from any of the above noted organisms, or from any type of stable cell line currently existing or produced from any primary cell culture;

3) genomic DNAs as described in item #1 above which are digested with restriction enzymes and prepared for Southern blot analysis by gel electrophoresis and transfer onto a solid support;

4) RNAs as described in item #2 above which are subject to electrophoresis and transfer to a solid support for Northern blot analysis. Such RNAs could include total cellular RNA or fractionated, poly $A^+$ RNA.

5) Products of polymerase chain reactions (PCR) which employ oligonucleotide primers based on sequences occurring in GDNF and employing as templates any of the nucleic acid sources described in items #1 through 4.

Any nucleic acid sequence which is demonstrated to hybridize to a GDNF based probe under some empirically determined set of hybridization conditions may be cloned and sequenced by any of a variety of techniques well known to one skilled in the art and the degree of sequence homology may be directly determined to identify members of a GDNF gene family. Such a hybridization approach was used to clone NT-3 by screening with a probe based on NGF sequence (Kaisho et al. 1990 *FEBS Letters* 266:187–191).

An alternative method for identifying GDNF family members involves use of the polymerase chain reaction (PCR) to amplify sequences from GDNF family members followed by cloning and analysis of amplified sequences. Degenerate (or nondegenerate) oligonucleotide primers for PCR may be synthesized based on the sequence of GDNF. Given the conservation of cysteine location and the conservation of amino acid sequences in the immediate vicinity of the cysteine residues that is observed for the NGF family, the regions around the cysteines in mature GDNF represent obvious candidates for primer synthesis but a variety of other primers could also be chosen from both the mature and pre-pro-portions of the protein. PCR reactions may be performed under conditions of reduced annealing temperature which would allow amplification of not only the GDNF sequence but the sequences of any GDNF family members. See, Innis et al. 1990 *PCR Protocols: A Guide to Methods and Applications,* Academic Press. The products of such PCR reactions may be size selected by gel electrophoresis, cloned into an appropriate vector and the cloned DNA sequenced to identify GDNF family members. Alternatively, the clones may first be screened by hybridization to a probe specific for GDNF under conditions of high stringency to identify GDNF clones. Any clones that fail to hybridize to GDNF under high stringency would then be sequenced or such clones could be hybridized to a GDNF probe under conditions of reduced stringency and any clones that did hybridize to the GDNF probe under these conditions would then be sequenced.

A second approach using PCR for cloning GDNF family members would be to label the products of the PCR reaction described above and use those products as a probe to screen nucleic targets enumerated above under conditions of high and/or low stringency. Hybridizing clones or nucleic segments could be analyzed as detailed above to identify GDNF clones and family members. Such an approach has been used to clone NT-3 based on the sequences of NGF and BDNF (Maisonpierre et al. 1990 *Science* 247:1446–1451).

In a preferred embodiment of the present invention, a therapeutic or pharmaceutical composition comprising GDNF is administered in an effective amount to patients suffering from nerve damage. In a preferred embodiment of the present invention, GDNF is used therapeutically to treat patients suffering from Parkinson's disease. Those skilled in the art are familiar with the variety of assays available for indicating which neurons would be responsive to treatment with GDNF, and the determination of other receptive neurons receptive to GDNF could be performed without undue experimentation. One skilled in the art could readily determine where the message for GDNF is expressed throughout the body and what the levels of GDNF protein are in each of those regions. One skilled in the art could also determine the location of binding sites for GDNF throughout the nervous system. This information would allow one skilled in the art to determine the neuronal types likely to be responsive to GDNF, which would in turn suggest the appropriate clinical indications for this protein. Suitable cell culture and animal experiments could then be run to determine the likelihood that GDNF would be useful in treating such indications.

Purified GDNF isolated from B49 conditioned medium has also been shown to promote the survival of parasympathetic and sympathetic nerve cells in cultures. These results are described in detail in Example 4.

Because it is possible that the neurotrophic function of GDNF is imparted by one or more discrete and separable portions, it is also envisioned that the method of the present invention could be practiced by administering a therapeutic composition whose active ingredient consists of that portion (or those portions) of GDNF which controls (or control) GDNF neurotrophic function.

The therapeutic or pharmaceutical composition of the present invention is preferably administered parenterally by injection or directly into the cerebral spinal fluid (CSF) by continuous infusion from an implanted pump. Also, other effective administration forms, such as parenteral slow-release formulations, inhalant mists, orally active formulations, or suppositories, are also envisioned. Also, administration in connection with one or more agents capable of promoting penetration of GDNF across the blood-brain barrier is envisioned. One preferred vehicle is physiological saline solution, but it is contemplated that other pharmaceutically acceptable carriers, such as artificial CSF, may also be used. In one preferred embodiment it is envisioned that the carrier and the GDNF constitute a physiologically-compatible, slow-release formulation. The primary solvent in such a carrier may be either aqueous or non-aqueous in nature. In addition, the carrier may contain other pharmacologically-acceptable excipients for modifying or maintaining the pH, osmolarity, viscosity, clarity, color, sterility, stability, rate of dissolution, or odor of the formulation. Similarly, the carrier may contain still other pharmacologically-acceptable excipients for modifying or maintaining the stability, rate of dissolution, release, or absorption or penetration across the blood-brain barrier of the GDNF. Such excipients are those substances usually and customarily employed to formulate dosages for parenteral administration in either unit dose or multi-dose form or for direct infusion into the CSF by continuous or periodic infusion from an implanted pump.

Once the therapeutic composition has been formulated, it may be stored in sterile vials as a solution, suspension, gel, emulsion, solid, or dehydrated or lyophilized powder. Such formulations may be stored either in a ready to use form or requiring reconstitution immediately prior to administration. The preferred storage of such formulations is at temperatures at least as low as 4° C. and preferably at −70° C.

Preferably, the manner of parenterally administering the formulations containing GDNF is via a subcutaneous, intramuscular, intrathecal or intracerebral route. To achieve the desired dose of GDNF, repeated daily or less frequent subcutaneous or intramuscular injections may be administered, or GDNF may be infused continuously or periodically from an implanted pump. The frequency of dosing will depend on pharmacokinetic parameters of GDNF in the formulation and route of administration used.

To achieve the desired dose of GDNF to dopaminergic and other damaged nerve cells whose cell bodies are within the brain and spinal cord, it is contemplated that GDNF will be administered into the brain or spinal cord subarachnoid space or intracerebroventricularly. Administration can be continuous or periodic and be accomplished by a constant- or programmable-flow implantable pump or by periodic injections. Administration can also occur in conjunction with agents that allow GDNF to penetrate the blood-brain barrier.

It is also contemplated that certain formulations containing GDNF are to be administered orally. Preferably, GDNF which is administered in this fashion is encapsulated. The encapsulated GDNF may be formulated with or without those carriers customarily used in the compounding of solid dosage forms. Preferably, the capsule is designed so that the active portion of the formulation is released at that point in the gastro-intestinal tract when bioavailability is maximized and pre-systemic degradation is minimized. Additional excipients may be included to facilitate absorption of GDNF. Diluents, flavorings, low melting point waxes, vegetable oils, lubricants, suspending agents, tablet disintegrating agents, and binders may also be employed.

Regardless of the manner of administration, the specific dose is calculated according to the approximate body weight or body surface area of the patient. Further refinement of the calculations necessary to determine the appropriate dosage for treatment involving each of the above mentioned formulations is routinely made by those of ordinary skill in the art and is within the ambit of tasks routinely performed by them without undue experimentation, especially in light of the dosage information and assays disclosed herein. These dosages may be ascertained through use of the established assays for determining dosages utilized in conjunction with appropriate dose-response data.

In one embodiment of this invention, GDNF may be therapeutically administered by implanting into patients cells capable of synthesizing and secreting a biologically-active form of GDNF. Such GDNF-producing cells may be cells that are natural producers of GDNF (analogous to B49 cells) or they could be cells whose ability to produce GDNF has been augmented by transformation with the GDNF gene in a form suitable for promoting its expression and secretion. In order to minimize a potential immunological reaction in patients from administering GDNF of a foreign species, it is preferred that the natural-GDNF-producer cells be of human origin and produce human GDNF. Likewise, one would transform cells to express human GDNF using an expression construct coding for human GDNF by methods analogous to those used in Examples 5 and 6 below.

Cells capable of naturally secreting human GDNF may be identified using the following tools: (1) Oligonucleotides representing a portion of the messenger RNA for human GDNF or complementary to a portion of the messenger RNA for human GDNF may be used to discover cell lines producing the human GDNF message by Northern blot analysis, RNase protection, in situ hybridization, the Polymerase Chain Reaction, or other related methods; or (2) Polyclonal or monoclonal antibodies that recognize human GDNF may be used to discover cell lines whose extracts or conditioned culture medium contain GDNF protein by Western blot analysis, ELISA assay, radioimmunological assay, or other related methods. A preferred strategy is to screen the conditioned culture medium from a series of cells of human origin with antibodies to human GDNF by the methods of (2) above to discover cells secreting GDNF into their culture medium. Confirmation of the GDNF so produced would come from purification and amino acid sequence analysis, as performed with the GDNF produced by B49 cells and secreted into their culture medium. Example 7 below describes the production and isolation of antibodies to human recombinant GDNF.

Cells naturally secreting or cells transformed to secrete human GDNF may be used to treat patients. Human or non-human animal cells may be implanted in patients in semi-permeable polymeric enclosures to allow release of GDNF, but prevent destruction of the cells by the patient's immune system. Alternatively, the patient's own cells, transformed to produce GDNF ex vivo, could be implanted directly into the patient without such encapsulation.

The methodology for the membrane encapsulation of living cells is familiar to those of ordinary skill in the art, and the preparation of the encapsulated cells and their implantation in patients may be accomplished without undue experimentation. See, U.S. Pat. Nos. 4,892,538; 5,011,472; and 5,106,627, each of which is specifically incorporated herein by reference. A system for encapsulating living cells is described in PCT Application WO 91/10425 of Aebischer et al., specifically incorporated herein by reference. See also, PCT Application WO 91/10470 of Aebischer et al.; Winn et al 1991 *Exper. Neurol.* 113:322–329; Aebischer et al. 1991 *Exper. Neurol.* 111:269–275; Tresco et al. 1992 ASAIO 38:17–23, each of which is specifically incorporated herein by reference.

In particular, cells secreting GDNF may be implanted in Parkinson's disease patients in the striatum to provide GDNF to the terminal fields of nigral dopaminergic neurons and into the nigra to provide GDNF to the dopaminergic cell bodies. Such locally-applied GDNF would promote sprouting and reinnervation of the striatum by dopaminergic terminals and would prevent or slow the further degeneration of the dopaminergic nerve cells.

The present invention includes, therefore, a method for preventing or treating nerve damage by implanting cells into the body of a patient in need thereof; such cells either selected for their natural ability to generate GDNF or engineered to secrete GDNF. Preferably, the secreted GDNF being human mature GDNF when the patient is human.

It should be noted that the GDNF formulations described herein may be used for veterinary as well as human applications and that the term "patient" should not be construed in a limiting manner. In the case of veterinary applications, the dosage ranges should be the same as specified above.

It is understood that the application of teachings of the present invention to a specific problem or environment will be within the capabilities of one having ordinary skill in the art in light of the teachings contained herein. Examples of representative uses of the present invention appear in the following examples.

EXAMPLES

Example 1

Purification and Sequencing of GDNF

This example describes methods for the bioassay and purification of GDNF. It also describes methods for preparing the B49 cell line conditioned medium that is the starting material for purification. Methods for obtaining amino acid sequence of purified GDNF and partial amino acid sequences obtained from the purified protein are also described.

A. Materials

Timed pregnant rats were from Zivie Miller lab, Allison Park, Pa. Unless specified, all reagents were from Sigma Chemical Co., St. Louis, Mo.

B. Bioassay for dopaminergic neurotrophic activities

Culture conditions: Dissociated mesencephalic cell cultures were prepared as previously described (Friedman and Mytilineou 1987 *Neurosci. Lett.* 79:65–72), with minor modifications. Briefly, rostral mesencephalic tegmentum from brains of Sprague-Dawley rat embryos, at the 16th day of gestation, were dissected under the microscope in sterile conditions, collected in $Ca^{2+}$- and $Mg^{2+}$-free Dulbecco's phosphate buffered saline (Gibco, Gaithersburg, Md.) and dissociated mechanically by mild trituration. The cells were plated in 100 µl per well onto 16-mm diameter tissue culture wells (Falcon, Lincoln Park, N.J., 24-well plate) containing 400 µl medium to give a density of $2.5$–$3.5 \times 10^5$ cells per well. The culture wells had been previously exposed to 0.1 mg/ml solution of poly L-ornithine in 10 mM sodium borate, pH 8.4, for 3 hours at 37° C., washed 3 times in milli-Q $H_2O$ and once in Earle's balanced salt solution (Gibco). The feeding medium (10/10) consisted of minimal essential medium (HEM, Gibco) supplemented with glucose (33 mM), sodium bicarbonate (24.5 mM), glutamine (2 mM), HEPES (15 mM), penicillin G (5 U/ml), streptomycin (5 µg/ml), 10% heat-inactivated fetal calf serum (Gibco) and 10% heat inactivated horse serum (Gibco). The cultures were kept at 37° C. in a water-saturated atmosphere containing 6.5% $CO_2$. After 3 hours, when most of the cells had adhered to the bottom of the well, the medium was replaced with 500 µl of fresh medium. At this time, a serial dilution of the sample to be assayed for GDNF activity was added to each well in duplicate and the plates were incubated in the 37° C. incubator. After a week, the cultures were treated for 24 hours with fluorodeoxyuridine (13 µg/ml) and uridine (33 µg/ml) to prevent excessive glial proliferation and subsequently fed with the above medium without fetal calf serum. The feeding medium was changed weekly.

Alternatively, chemically defined serum-free medium was used in which serum was replaced by a mixture of proteins; hormones and salts. The defined medium (DM) consisted of a mixture of MEM and F12 nutrient mixture (both Gibco, 1:1; vol/vol) with glucose (33 mM), glutamine (2 mM) $NaHCO_3$ (24.5 mM), HEPES (15 mM), supplemented with transferrin (100 µg/ml), insulin (25 µg/ml), putrescine (60 µM), progesterone (20 nM), sodium selenite (30 nM), penicillin G (5 U/ml) and streptomycin (5 µg/ml). The osmolarity of the DM was adjusted to 325 by the addition of milli-Q $H_2O$. (110–125 ml $H_2O$/l). Using DM, few nonneuronal cells were evident, by morphology or by staining for glial fibrillary acidic protein (GFAP), which is an astrocyte-specific cytoskeletal protein. GDNF is active in stimulating dopamine uptake in both serum-containing and defined media. All assays reached in the following examples were done in serum-containing medium.

The functional status of the dopaminergic neurons may be assayed in these cultures by measuring dopamine uptake through specific "scavenger" transporters in the dopaminergic neurons and by counting the number of neurons positive for the dopamine synthetic enzyme tyrosine hydroxylase using immunohistochemistry. The possibility of significant contamination of the cultures with the noradrenergic neurons, which can also transport dopamine and also contain tyrosine hydroxylase, was ruled out by careful dissection and by demonstrating that the dopamine transporters have the pharmacological profile characteristic of dopaminergic, rather than noradrenergic, neurons. Dopamine uptake in these cultures is inhibited by GBR12909, an inhibitor of the monoamine transporter on dopaminergic neurons, with an $ED_{50}$ of 20 nM. In contrast, at least 300-fold more desipramine, an inhibitor of monoamine transporter or noradrenergic neurons, is required to inhibit dopamine uptake in their cultures. These values are those that have been reported for the monoamine transporter in dopaminergic neurons.

Sample Preparation: Prior to being assayed for dopaminergic neurotrophic activity in the mesencephalic cell cultures, all the samples generated from Step 1 to Step 3 of purification (see Section C below) were desalted as follows. One hundred µl of the medium 10/10 (as a carrier) was added to a Centricon-10 (Amicon) and allowed to sit for 10 minutes. Aliquots of the sample to be assayed were added to the Centricon, followed by 1 ml of Dulbecco's high glucose Modified Eagle medium, without bicarbonate, but containing 10 mM HEPES, pH 7.2 (solution A), and centrifuged at 5,000×g for 70 minutes. The retentate (about 0.1 ml) was brought back to 1.1 ml with fresh solution A and reconcentrated twice. The sample was filtered through a 0.11 µm Ultrafree-MC sterile Durapore unit (Millipore, Bedford Mass.) prior to being added to the culture well.

$^3$H-dopamine uptake: Uptake of tritiated dopamine ($^3$H-DA) was performed in cultures at day 6 or day 7 as described previously (Friedman and Mytilineou (1987) Neurosci. Lett. 79:65–72) with minor modifications, and all the solutions were maintained at 37° C. Briefly, the culture medium was removed, rinsed twice with 0.25 ml of the uptake buffer which consists of Krebs-Ringer's phosphate buffer, pH 7.4, containing 5.6 mM glucose, 1.3 mM EDTA, 0.1 mM ascorbic acid and 0.5 mM pargyline, an inhibitor of monoamine oxidase. The cultures were incubated with 0.25 ml of 50 nM $^3$H-DA (New England Nuclear, Boston, Mass. sp. act 36–37 Ci/mmol) for 15 minutes at 37° C. $^3$H-DA uptake was stopped by removing the incubation mixture and cells were then washed twice with 0.5 ml of the uptake buffer. In order to release $^3$H-DA from the cells, the cultures were incubated with 0.5 ml of 95% ethanol for 30 min at 37° C., and then added to 10 ml of EcoLite (ICN, Irvine, Calif.) and counted on a scintillation counter. Blank values were obtained by adding to the uptake buffer 0.5 mM GBR-12909 (RBI), a specific inhibitor of the high-affinity uptake pump of the dopamine neurons (Heikkila et al. 1984 Euro J. Pharmacol. 103:241–48) and were usually less than 5% of the $^3$H-DA uptake in untreated control cultures. The number of trophic units (TU) of GDNF activity was defined as the reciprocal of the dilution that gave 50% of maximal stimulation of the $^3$H-DA uptake of the culture. Specific activity was determined by dividing the number of TUs by the amount of protein present in the sample.

C. Purification of GDNF

Starting material: B49 glioblastoma cells obtained from D. Schubert, Salk Institute, La Jolla, Calif. (See Schubert et al. 1974 Nature 249:224–27) were grown to confluence in DMEM medium containing 10% fetal calf serum, 4 mM glutamine, 50 U/ml penicillin-G and 50 µg/ml streptomycin in culture flasks (225 cm$^2$, Costar, Cambridge, Mass.). The serum-free growth-conditioned medium (CM) was prepared by washing the culture once with 10 ml of serum-free medium and then placing the cells in 50 ml per flask of serum-free medium for 2 days. CM was collected, and the cells were replenished with fresh serum-free medium every 2 days thereafter until day 6. The combined CM of 3 harvests from each batch of cells was centrifuged at 5,000×g for 20 min at 4° C. to remove cells and debris. The supernatant was concentrated approximately 10-fold via Amicon concentrator (YM10 membrane) and centrifuged at 40,000×g for 20 minutes at 4° C. The supernatant was filtered through 0.2µ Micro Culture Capsule (Gelman Sciences) and could be stored at 4° C. for up to one month.

Step 1. Heparin Sepharose Chromatography: The above preparation (200 mg of protein) was loaded onto a column (1×25 cm) of Heparin Sepharose CL-6B (Pharmacia, Piscataway, N.J.) equilibrated with 50 mM NaPi buffer, pH 8.0, containing 0.15 N NaCl (buffer A). The column was then washed with the same buffer until the optical density at 280 nm ($O.D_{280}$) of the effluent returned to baseline and eluted with a 100 ml linear gradient running from buffer A into 50 mM NaPi, pH 8.0, containing 1.5 N NaCl (buffer B). Two ml fractions were collected. Fractions were analyzed for conductivity and the GDNF activity. FIG. 1 shows such a chromatography. The profile of eluted proteins is plotted as $O.D_{280}$. Superimposed are plots of the conductivity and GDNF activity measured in each fraction. The fractions indicated by the bar with peak GDNF activity (around 0.6–0.8 N NaCl) were pooled for further analysis.

Figure 2:
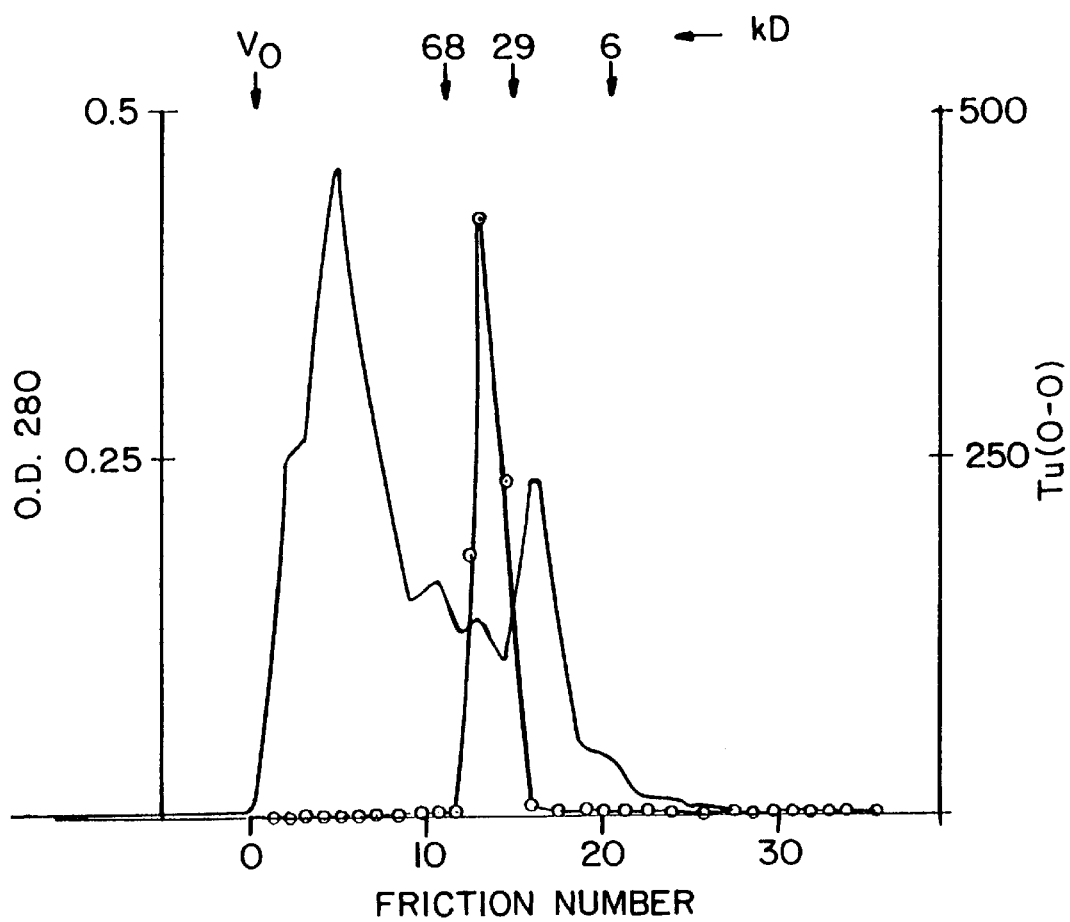
FIG. 2 depicts the results of FPLC superose chromatography from the pooled fractions of FIG. 1. The results are shown of $O.D._{280}$ (——), and GDNF activity in TU (-o-).

Step 2. FPLC Superose Chromatography: The above pool was concentrated to 0.4 ml via Amicon concentrator (Amicon, Beverly, Mass., YM10 membrane) and chromatographed on a fast protein liquid chromatography (FPLC) Superose 12 column (Pharmacia) in 50 mM NaPi buffer, pH 7.4, containing 0.5 N NaCl with a flow rate of 0.5 ml/min. After 14 min of elution, fractions of 0.5 ml were collected into siliconized microfuge tubes containing 5 µl of 0.4% Tween 20. Aliquots from each fraction were analyzed for GDNF activity. FIG. 2 shows such a chromatography with the protein profile traced at $O.D_{280}$ and with the GDNF activity pattern superimposed. 85% of the GDNF activity loaded on the column was recovered in fractions #12–15.

Figure 3A:
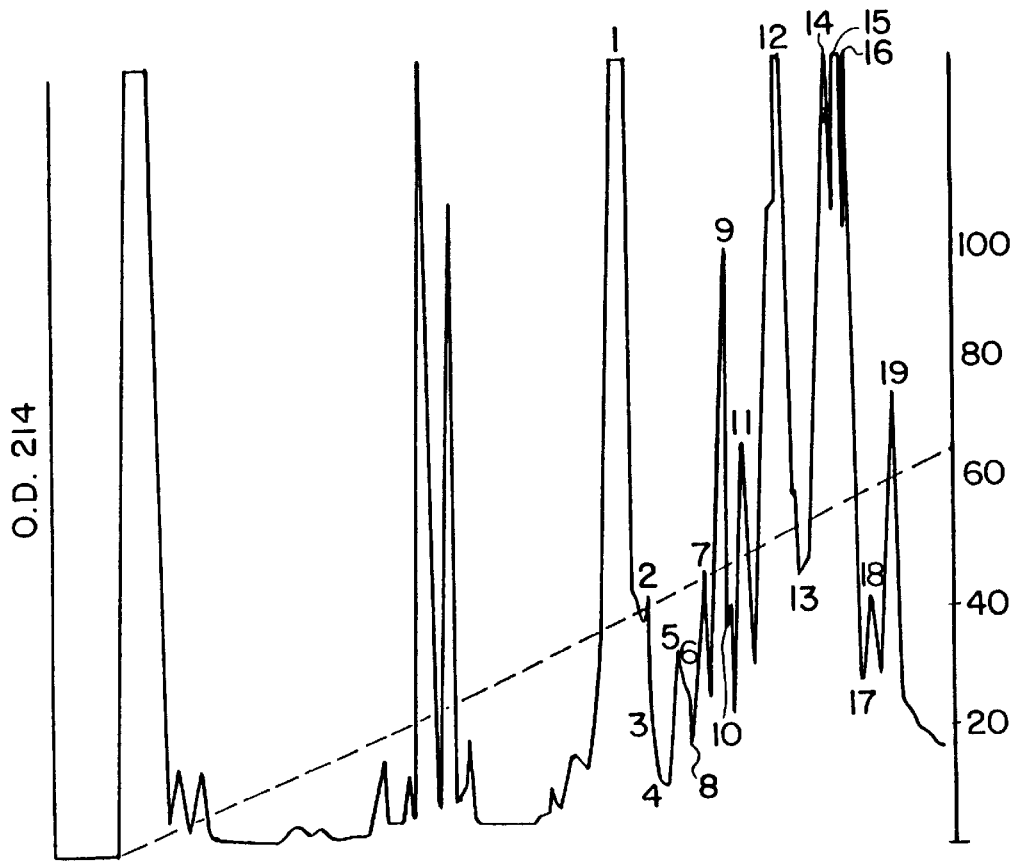
FIGS. 3A–B depicts the results of RP-HPLC on fraction 14 from FIG. 2. The results are shown of $O.D._{214}$, with the GDNF activity in TU shown below (FIG. 3B).
Figure 3B:
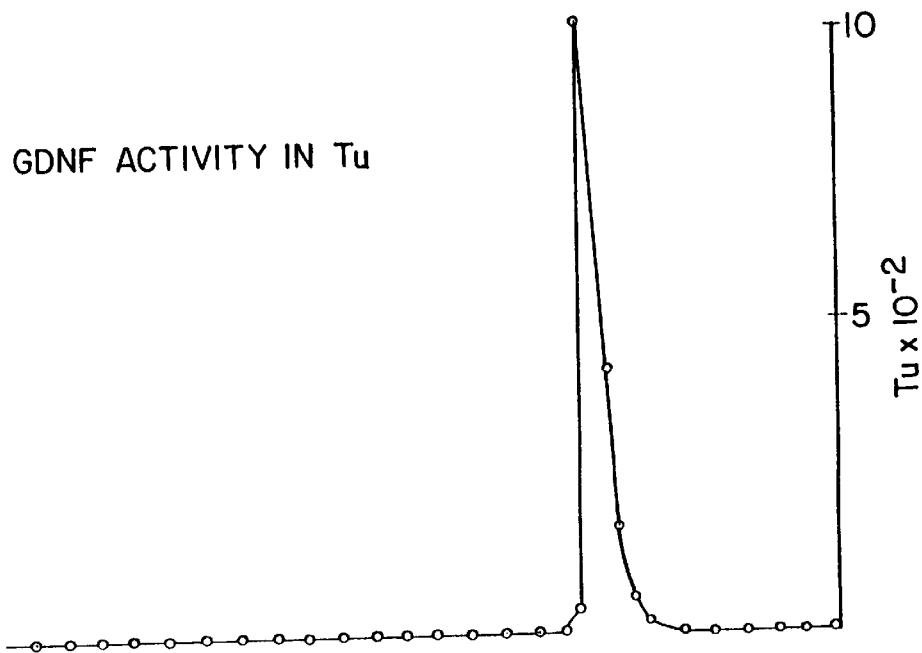
Figure 4:
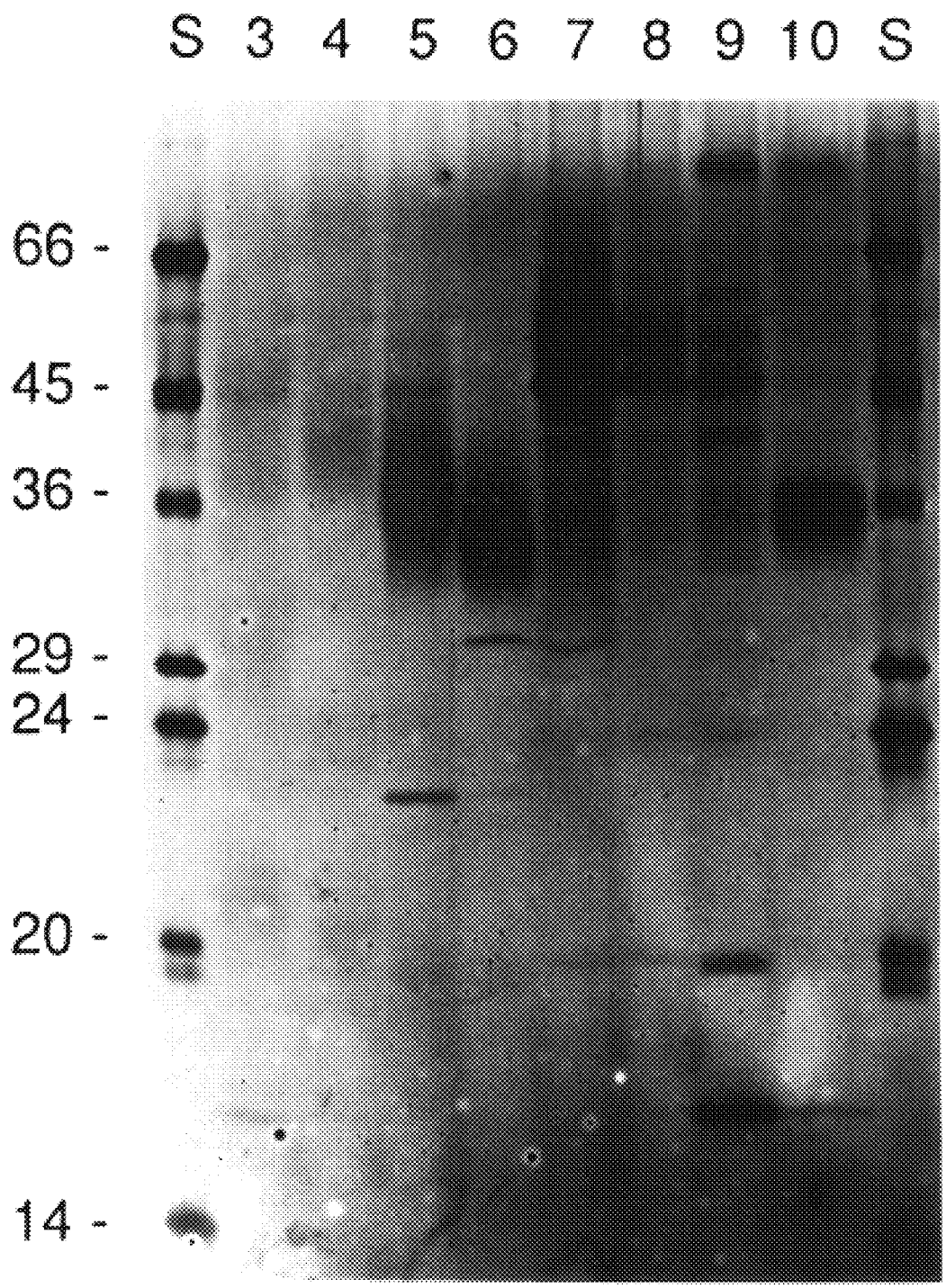
FIG. 4 depicts the results of analysis by silver-stained SDS-PAGE of fractions 3–10 obtained from FIG. 3 above. Lane S contains molecular weight standards.

Step 3. RP-HPLC: Fraction #14 from above was acidified with 10 µl of 25% trifluoroacetic acid (TFA). Half of the acidified material was loaded onto a narrow bore Aquapore RP-300 C-8 reverse phase HPLC column (Brownlee column, Applied Biosystems, San Jose, Calif.), 2.1×220 mm, and eluted with an $H_2O/0.1$% TFA: 80% acetonitrile/ 0.085% TFA gradient. Protein containing fractions were collected manually into siliconized microfuge tubes based on the UV absorption at 214 nm. Aliquots from each fraction were analyzed for GDNF activity. FIG. 3 shows such a chromatography with the protein profile traced at $O.D_{214}$ and with the activity pattern in the lower panel. Fractions 5 and 6 contained about 90% of the activity recovered in RP-HPLC, while fraction 7 accounted for the remaining 10% of the activity. FIG. 4 shows a silver stained SDS-PAGE gel run of the fractions around the GDNF activity peak shown in FIG. 3.

Step 4. Preparative SDS-PAGE: Fractions 5 and 6 containing the peak GDNF activity were pooled and concentrated to 20 µl in the presence of 10 µl of 0.4% Tween 20 on a speed vac. Added to the sample were 1 µl of 1 M Tris base and 5 μl of 0.2 M Tris-HCl, pH 6.8, containing 40% glycerol and 5% SDS, and run on non-reduced 15% SDS-PAGE (Laemmli 1970 *Nature* 277:680–684) (slab of 0.075×14× 11.5 cm, 20 well-comb, 0.075×0.4×2.8 cm/sample well). Electrophoresis was conducted at 10° C. at 40 mA/gel for 2 hours. The gel strip was sliced into 1.14 mm slices. Each slice was cut into 2 smaller pieces and eluted with 3 sequential changes of 25 μl 5 mM NaPi, pH 6.7 containing 0.01% Tween 20, over a 20 hour period with continuous rocking at 4° C. The 3 aliquots of eluted material were combined, assayed for GDNF activity (FIG. 5), and the eluate with highest activity (from gel slice #16–23 corresponding to 30–42 kD in FIG. 5) was pooled. A blank gel strip (on top of which was loaded only the SDS-PAGE sample buffer prior to electrophoresis) was processed similarly as a control.

Figure 5:
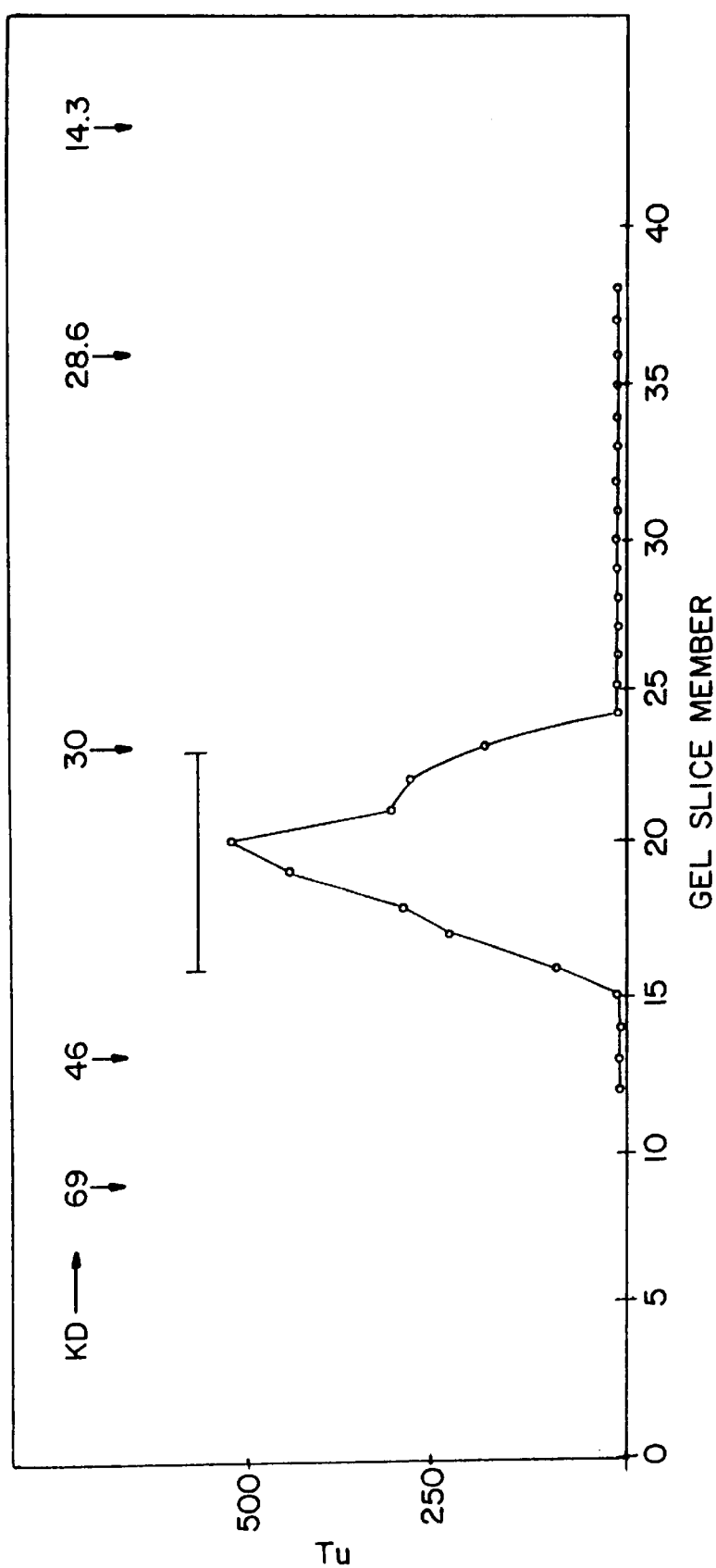
FIG. 5 depicts the results of preparative SDS-PAGE on fractions 5 and 6 from FIG. 4. Gel slices were tested for GDNF activity in TU. Gel slices were also correlated to molecular weight by use of molecular weight markers (Amersham).
Figure 7:
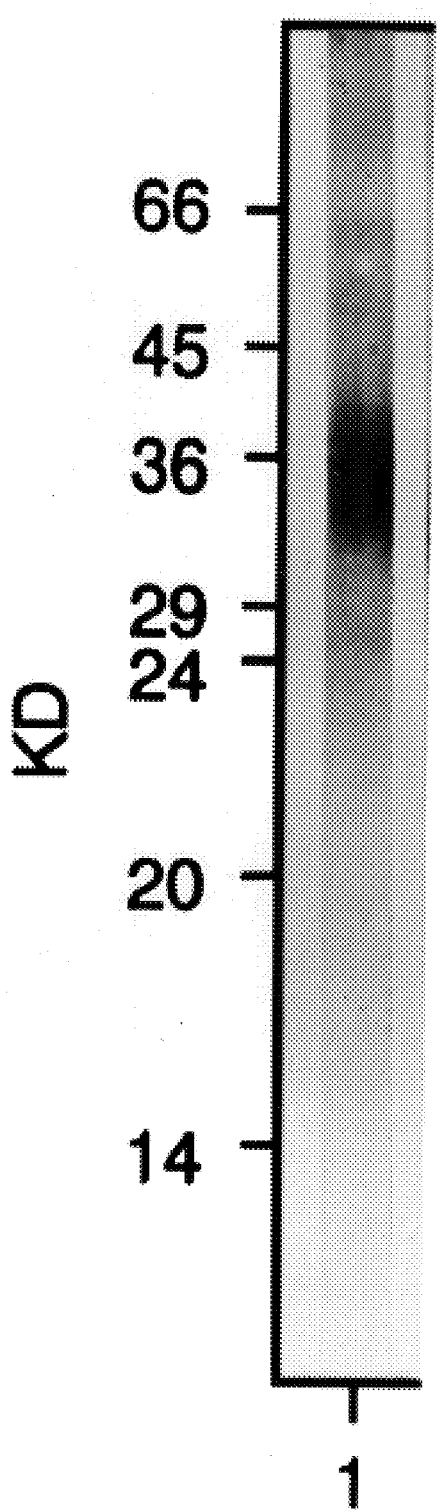
FIG. 7 depicts the results of analysis by silver-stained SDS-PAGE of peak 3 from FIG. 6A (lane 1) and a molecular weight control (lane S).

Step 5. RP-HPLC: The pooled gel eluent was concentrated to about 150 μl on a speed vac, acidified with 20 μl of 25% TFA and run on RP-HPLC as described in Step 3. Protein containing fractions were collected manually into siliconized microfuge tubes, based on $O.D_{214}$ and assayed for GDNF activity. FIG. 6 shows the results of such chromatography. As a control, the eluent from similarly sized blank gel slices was also run on RP-HPLC. The only significant $O.D_{214}$ peak in the sample above the control profile (FIG. 6, panel A vs. B) is peak 3, which contains 70% of the GDNF activity loaded on the HPLC column. FIG. 7 shows peak 3 run on a silver-stained SDS-PAGE gel. The only visible stain is a very broad band between 30–42 kD, coinciding with the GDNF activity profile observed in preparative SDS-PAGE (FIG. 5). The summary of a typical purification is given in Table I.

D. Amino acid sequence of purified GDNF

Amino-terminal sequence: Peak 3 in FIG. 6 was sequenced with a gas phase protein sequencer (Applied Biosystems). The sequence obtained is given in FIG. 8. Sequencing of fractions with the peak GDNF activity after step 3 of the purification (fractions 5 and 6 in FIG. 3) also revealed a single sequence, identical to that in FIG. 8, obtained with the purified sample. The only material these different fractions have in common is the material running as a smear between 30–42 kDa. Therefore, the contaminating bands outside the 30–42 kD regions seen in silver-stained gel of fractions 5 and 6 in FIG. 4 could a) be too small in amount (<1 picomoles) to be sequenced by the current technology; b) be related to the 30–42 kD smear band in sequence; or c) have a blocked amino-terminus.

Figure 9A:
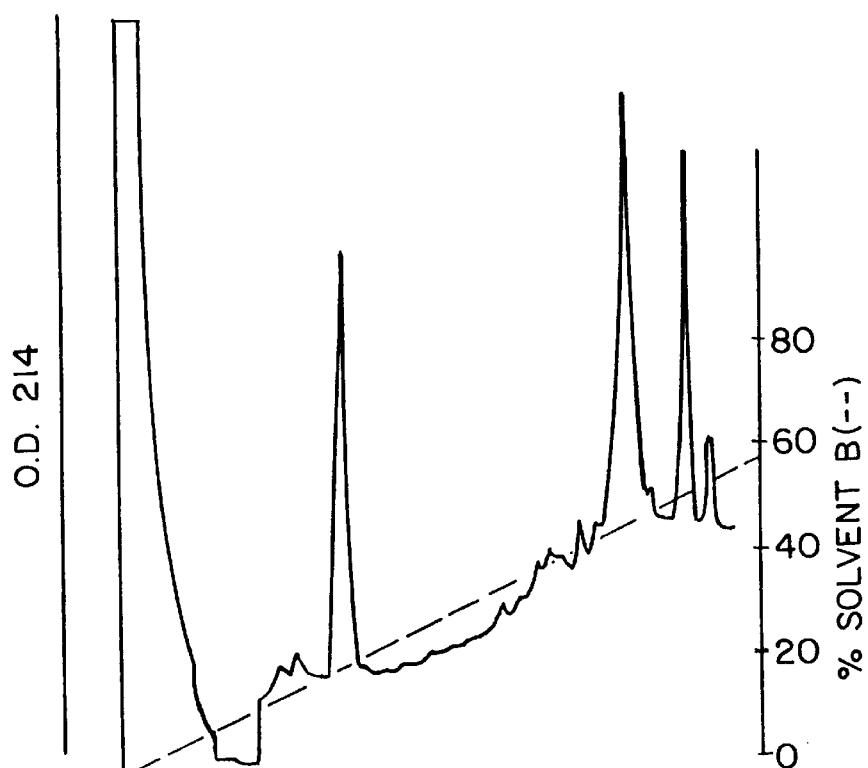
FIGS. 9A–B depicts the results of RP-HPLC on trypsin digested purified GDNF. Chromatogram A contains the sample, and chromatogram B is a control (containing trypsin only).
Figure 9B:
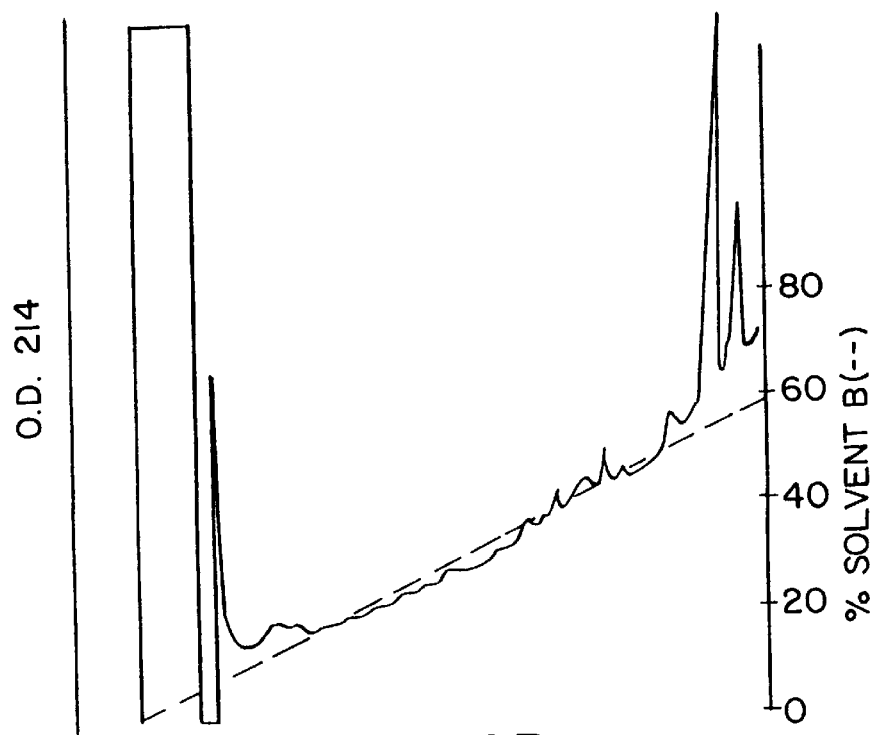
Figure 10:
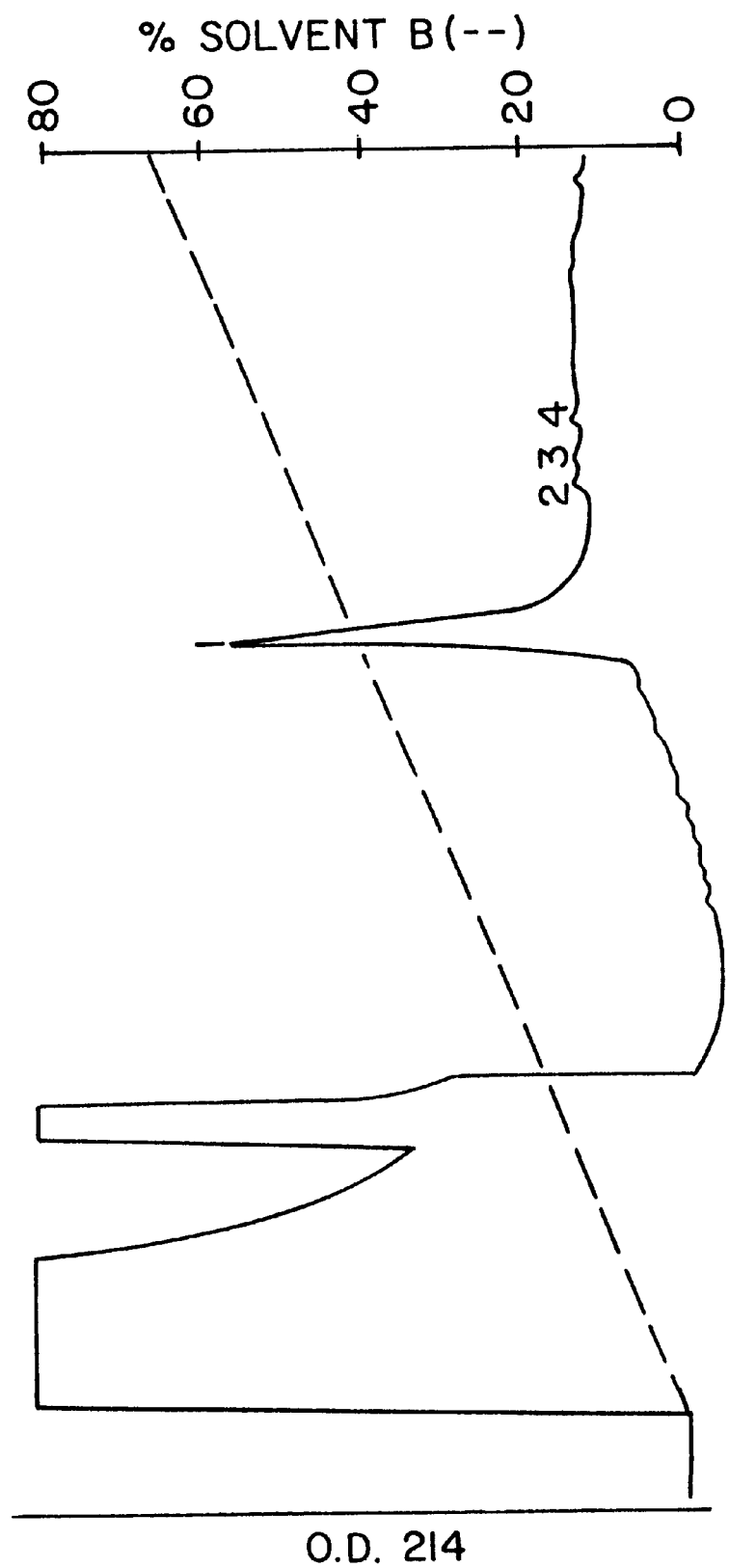
FIG. 10 depicts the results of the RP-HPLC of peak 37 from FIG. 9. following treatment with cyanogen bromide.
Figure 11:
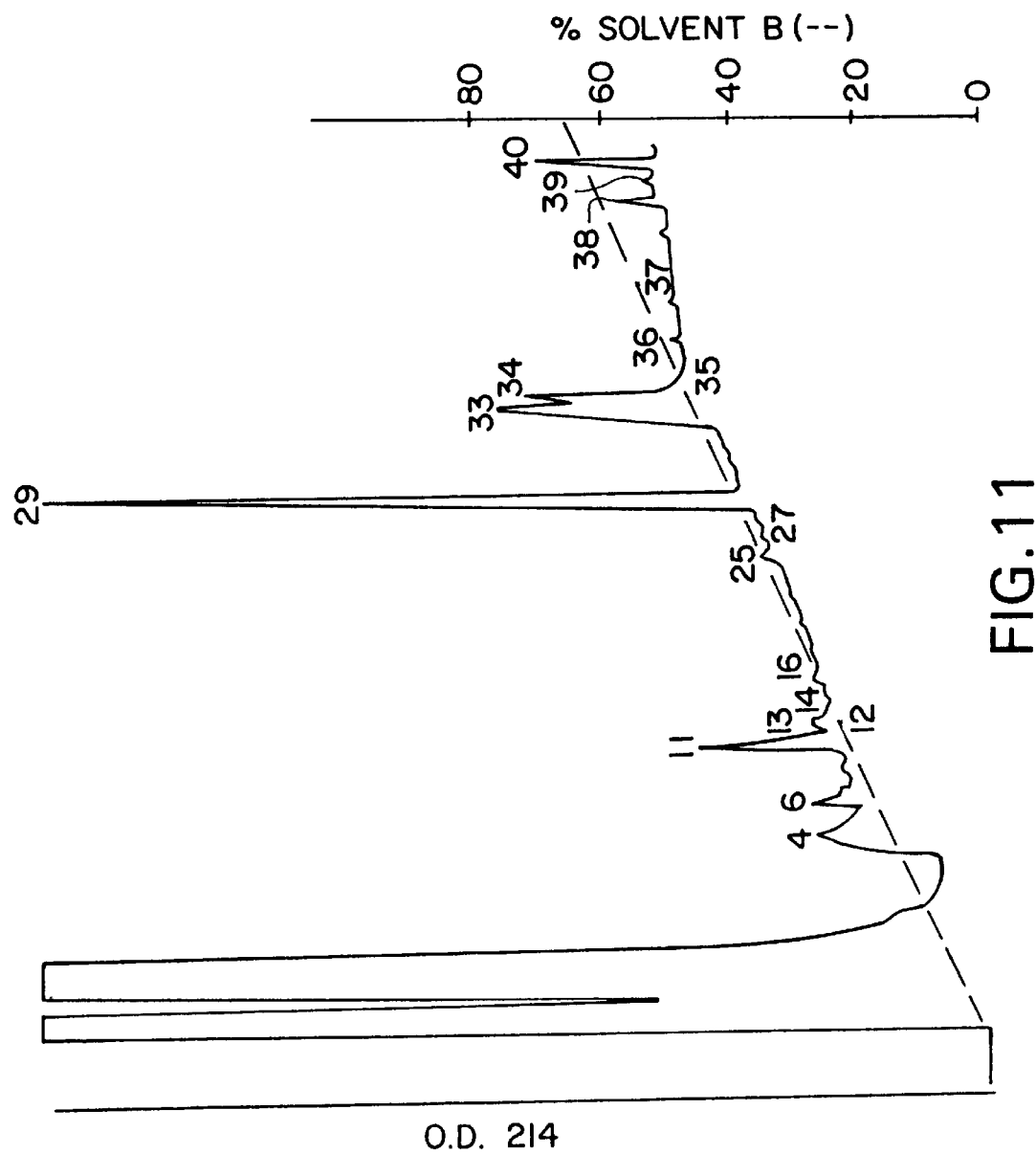
FIG. 11 depicts the results of RP-HPLC on the reduction product of peak 1 from FIG. 10.

Internal sequence: GDNF preparation after step 3 of the purification described above was used as the starting material to obtain internal sequence. Fractions 5 and 6 in FIG. 3 were pooled into a siliconized microfuge tube containing 9 μl of 0.4% Tween and concentrated to 40 μl on a speed vac. Added to the sample were 160 μl of 1% $NH_4HCO_3$ containing 2.5 M guanidine hydrochloride and 1 μg of trypsin, and the sample was incubated overnight at 37° C. The mixture was acidified with 20 μl of 25% TFA, concentrated to about 150 μl on a speed vac, and peptides were separated on a narrow bore Aquapore RP-300 C8 reverse phase HPLC column (Brownlee column), 2.1×220 mm, and eluted with an $H_2O$/0.1% TFA:80% acetonitrile/0.085% TFA gradient. Peptide containing fractions were collected manually into siliconized microfuge tubes based on the absorption at 214 nm. FIG. 9 shows the results of such chromatography. Sequence of peak 10 in FIG. 9 was determined to be identical to the first 13 amino acid residues of the amino-terminal sequence of the untreated protein shown in FIG. 8 (SEQ ID NO:1). Peak 37 in FIG. 9 was further treated with CNBr. The sample was concentrated to 20 μl on a speed vac. Added to the sample was 70 μl of 90% formic acid and 5 mg of CNBr, and the sample was incubated in the dark overnight at room temperature. This mixture was concentrated to 20 μl on a speed vac, diluted with 100 μl of 0.1% TFA and separated on reverse phase HPLC as described above. FIG. 10 shows the results of such chromatography. Peak 1 in FIG. 10 was concentrated to 20 μl in the presence of 5 μl of 0.4% Tween 20 on a speed vac. Added to the sample was 100 μl of 1% $NH_4HCO_3$ and 5 μl of 50 mM dithiothreitol and the sample was incubated at room temperature for an hour. The mixture was acidified with 10 μl of 25% TFA, concentrated to 100 μl on a speed vac and separated on reverse phase HPLC as above. FIG. 11 shows the results of such chromatography. Both peaks 33 and 34 in FIG. 11 gave an identical sequence (FIG. 12) (SEQ ID NO:2).

E. Characteristics of GDNF

Mobility on SDS-PAGE: Without any heat treatment of the sample and under non-reducing conditions, GDNF runs as a smear band between 31–42 kD on SDS-PAGE. When the sample is heated at 100° C. for 3 min in the presence of reducing agent (4% β-mercaptoethanol), GDNF runs as discrete multiple bands between 20–23 kD. Since about 50% of the bioactivity loaded onto the gel could be recovered under the former (non-reducing) but not the latter (reducing) conditions, GDNF may be a disulfide-bonded dimer and only active as a dimer. While a single amino-terminus suggests the GDNF preparation is homogeneous with respect to the core primary structure, the smear or multiple banding pattern is suggestive of a heterogeneously glycosylated protein.

Specific activity: Purified GDNF had an estimated specific activity of about 17 trophic units/ng, which indicates that half-maximal stimulation of dopamine uptake occurs at the relatively low concentration of approximately 60 pg/ml. The specific activity measured for purified GDNF may be underestimated somewhat due to partial inactivation of GDNF during purification by exposure to the acidified organic solvents used in RP-HPLC and to the denaturing conditions in SDS-PAGE.

Figure 20A:
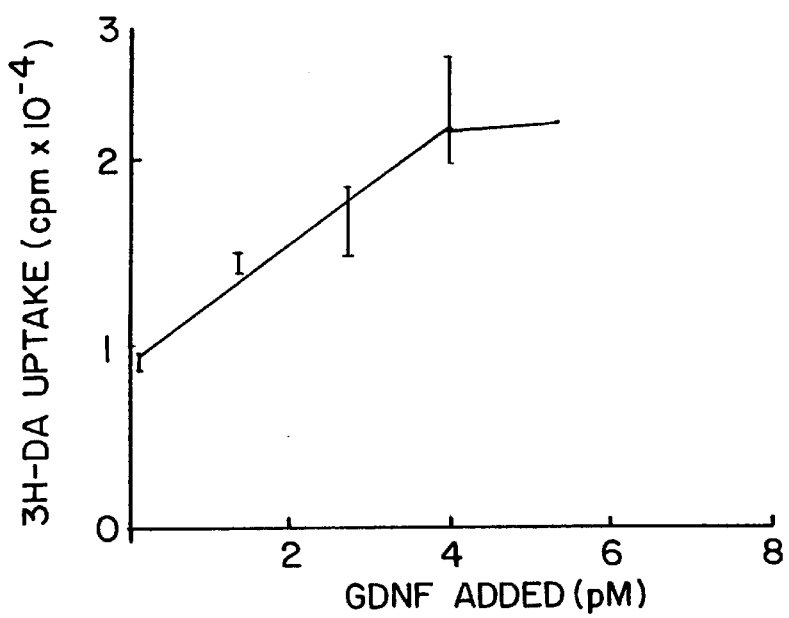
FIGS. 20A–B depicts the ability of GDNF to stimulate dopamine uptake and tyrosine hydroxylase (TH) immunostaining in dopaminergic neurons. Cultures were established as described in Example 1B. GDNF was added on the day of plating and replenished after nine days in vitro. A. $^3$H-DA uptake was measured after 15 days in vitro. B. Cultures were fixed after 16 days in vitro with 4% paraformaldehyde, washed extensively, permeabilized with 0.2% Triton x-100 and stained with polyclonal antibody to TH (Eugine Tech International, Allendale, N.J.). Primary antibody binding was visualized using a Vectastain ABC kit (Vector Labs, Burlingame, Calif.).
Figure 20B:
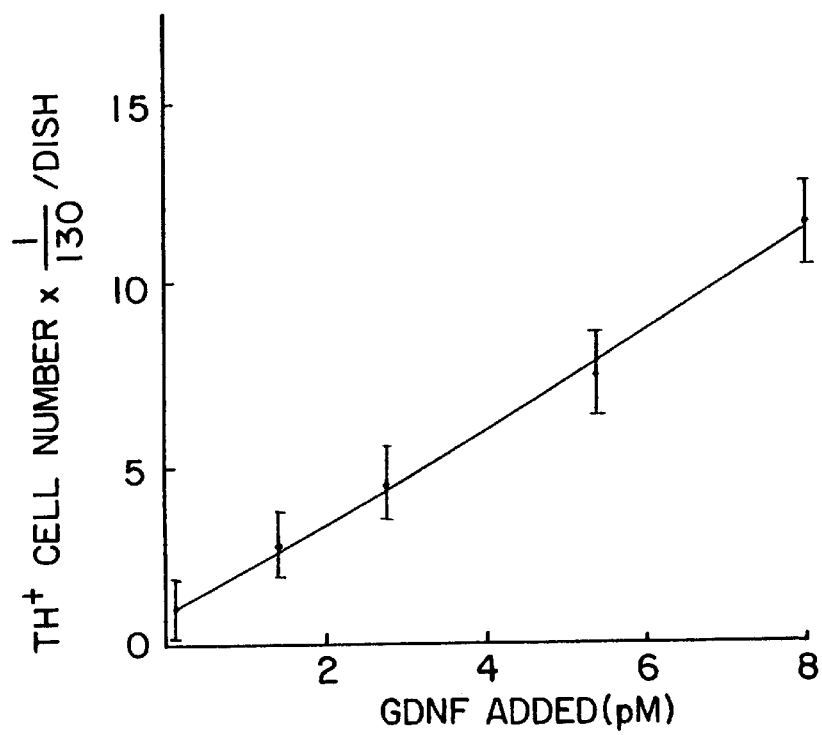

Specificity of GDNF: GDNF was purified by its ability to enhance the uptake of dopamine in dopamine neurons (FIG. 20A). To determine whether GDNF also upregulated another index of survival and/or maturation of the dopamine neurons, tyrosine hydroxylase (TH) immunoreactivity in the mesencephalic cultures was also measured. TH is a marker specific to dopamine neurons in the cultures. The upregulation of immunoreactivity by GDNF could be due to the increased survival of dopamine neurons and/or to an increase in production of TH per dopamine neurons. Purified GDNF added at the day of plating and cultures examined eight days later resulted in a tenfold higher number of $TH^+$ neurons over controls without GDNF. If a second dose of GDNF was added at day 9 and cultures examined seven days later (16 days in vitro), a similar dose-dependent increase over control could still be observed (FIG. 20B). Thus, GDNF could sustain survival of dopamine neurons and/or increase the expression of the TH gene in mesencephalic dopamine neurons.

Figure 21A:
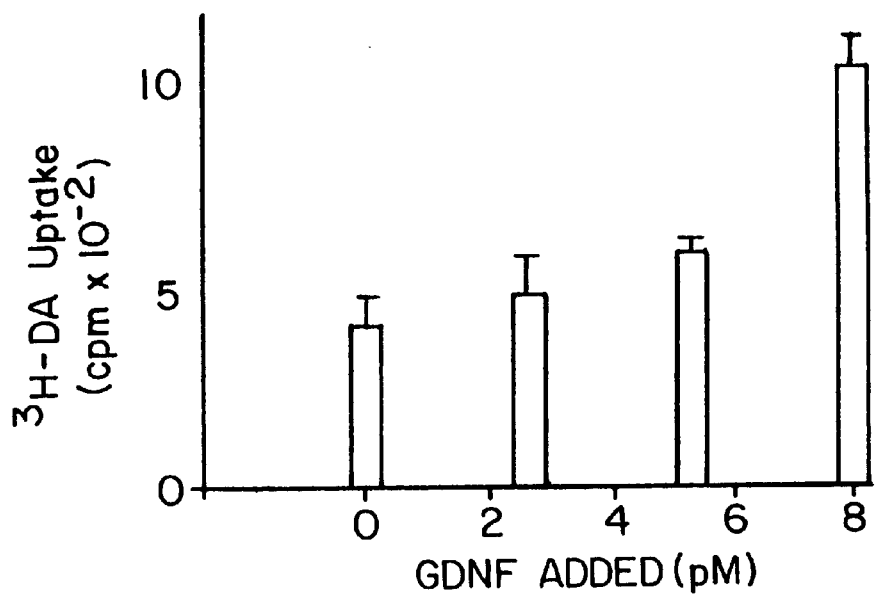
FIGS. 21A–C depicts the specificity of GDNF to dopaminergic neurons. Cultures were established as described in Example 1B. GDNF was added on the day of plating. A. $^3$H-DA uptake was measured after seven days in vitro. B. $^{14}$C-GABA uptake was measured after eight days in vitro. Cells were incubated and treated as for $^3$H-DA uptake, except the uptake buffer consists of Kreb-Ringer's phosphate buffer, pH 7.4, containing 5.6 mM glucose, 1.3 mM EDTA, 10 $\mu$M amino-oxyacetic acid (to prevent GABA breakdown), 2 mM β-alanine (to inhibit glia uptake of GABA) and 0.1 $\mu$M $^{14}$C-GABA (150 mC$_i$/mmole, New England Nuclear, Boston, Mass.). In the presence of 1 mM diaminobutyric acid (DABA), a potent inhibitor of $^{14}$C-GABA uptake into GABA neurons, the $^{14}$C-uptake was reduced to 10%. Control values in the presence of DABA were subtracted from experimental values. C. The ratio of $^3$H-DA/$^{14}$C-GABA uptake as a function of GDNF added.
Figure 21B:
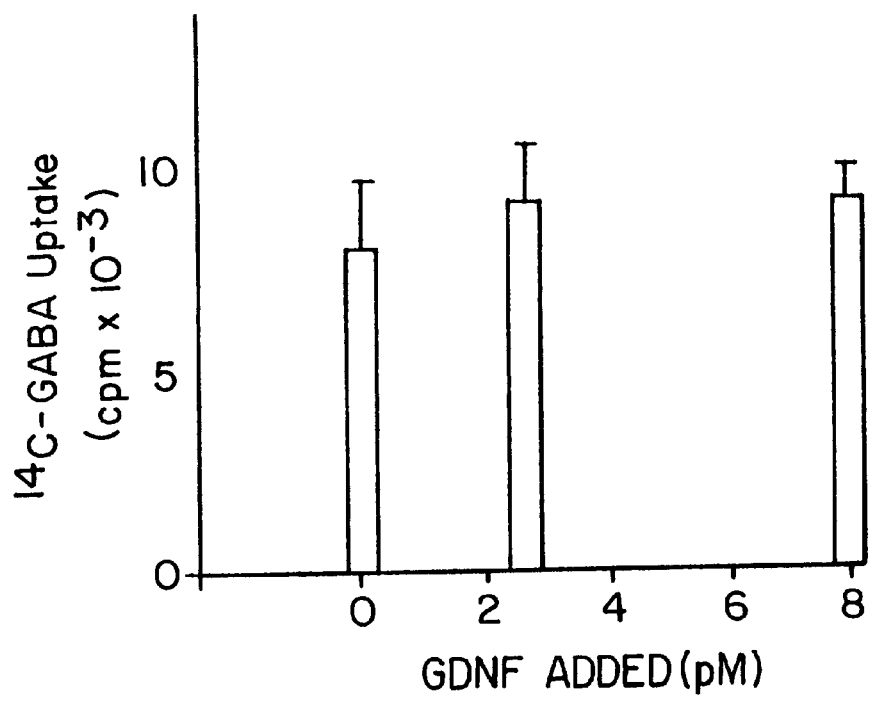
Figure 21C:
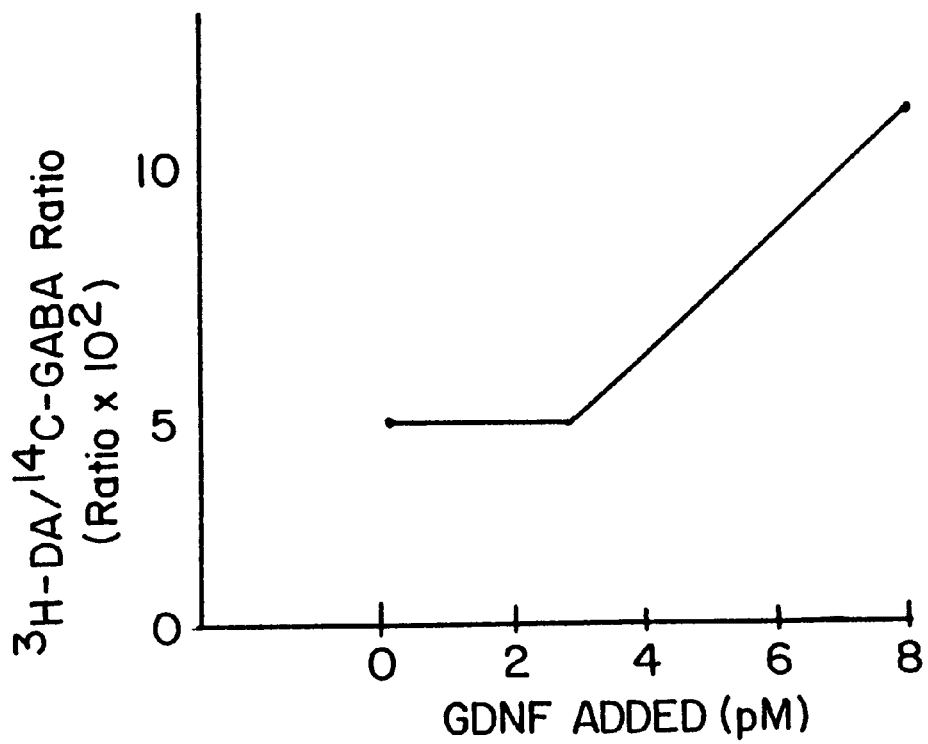

To demonstrate that GDNF exerts a specific stimulating effect on the maturation and/or survival of dopamine neurons and not a general action on all neurons, the responsiveness to GDNF of neurons containing γ-aminobutyric acid (GABA), which are also present in mesencephalic cultures, was analyzed. $H^3$-dopamine ($^3$H-DA) and $^{14}$C-GABA uptake were measured in sister cultures of mesencephalic cells which had been grown with various concentrations of GDNF for 15 and 16 days, respectively. As described above, GDNF enhanced the $^3$H-DA uptake capacity of mesencephalic dopamine neurons ~150% over control without GDNF (FIG. 21A). However, GDNF had no significant effect on the capacity of GABA neurons to take up $^{14}$C-GABA since the $^{14}$C-GABA uptake in the presence of GDNF was only ~20% higher than that of the control (FIG. 21B). This is also illustrated by the increase in the $^3$H-DA/$^{14}$C-GABA uptake ratio calculated (FIG. 21C). These data indicate that dopamine and GABA mesencephalic neurons respond differently to the presence of GDNF and the stimulating effect of GDNF on $^3$H-DA uptake in mesencephalic cultures is specific for dopamine as contrasted to GABA neurons.

These observations further illuminate why GDNF may be used to treat Parkinson's disease or other disorders involving dopaminergic neurons. These results demonstrate that GDNF upregulates at least two important properties of dopaminergic neurons: dopamine uptake and TH enzyme levels. The results also demonstrate that the effects of GDNF are at least partially specific for dopaminergic neurons, since GABA neurons are not similarly affected.

In addition to dopaminergic and GABAergic neurons, there is another neuronal population, serotonergic neurons, in the rat embryo mesencephalic cultures. Some factors, such as epidermal growth factor (EGF) that increase dopamine uptake by dopaminergic neurons in mesencephalic cultures, also increase serotonin uptake by the serotonergic neurons and GABA uptake by GABAergic neurons. See, Casper et al. 1991 *J. Neurosci,* 30:372. This indicates that these factors are not specific for dopaminergic neurons.

In contrast, GDNF fails to increase the uptake of serotonin by the serotonergic neurons. $^3$H-serotonin uptake was measured in the same manner as for $^3$H-DA uptake as described in Example 1B, except that the uptake buffer contained 50 nM $^3$H-serotonin (11 Ci/mole, Amersham, Arlington Heights, Ill.) instead of $^3$H-DA. In the presence of 10 $\mu$M citalpram (obtained from Dr. C. Mytilineou, Mount Sinai School of Medicine), a known potent inhibitor of serotonin uptake in serotonin neurons, the $^3$H-serotonin uptake was reduced to 15%. Control values in the presence of citalpram were subtracted from experimental values shown in FIG. 24.

In contrast to non-specific factors like EGF, GDNF fails to increase GABA uptake (FIG. 21) and serotonin uptake (FIG. 24) under conditions in which dopamine uptake is increased significantly. These and the results described above indicate that GDNF is specific for dopaminergic neurons in the mesencephalic cultures when compared to the GABAergic and serotonergic neurons present in the same cultures. Such specificity enhances the usefulness of GDNF for treating Parkinson's disease, which is considered to be a disease specific to the mesencephalic (nigral) dopaminergic neurons.

Example 2

Cloning of the Gene for GDNF

A. Cloning of a cDNA Copy of the Rat Gene that Encodes GDNF

In order to clone the gene encoding GDNF, a cDNA library was constructed from poly A$^+$ RNA isolated from B49 cells, and this library was screened with a degenerate oligonucleotide probe based on the amino acid sequence obtained from purified GDNF. A cDNA clone that hybridized to this probe was determined, by DNA sequencing, to contain DNA sequences that are located 3' to the sequences used in the degenerate oligonucleotide probe, that encoded an amino acid sequence present in GDNF and located carboxyterminal to the amino acid sequence upon which the screening oligo probe was based.

Culture conditions for the B49 cell line are described in detail in Example 1 above. For RNA preparation, cells were grown to near confluence in serum containing medium, washed once in serum-free medium (DMEM) and grown for 4 days in DMEM with one medium change after 2 days. The cells were then harvested and total RNA extracted by the method of Chomczynski and Sacchi 1987 *Analytical Biochemistry* 162:156–159. Poly adenylated RNA was prepared from this total RNA by passage over an oligo dT cellulose affinity column as described by Maniatis et al. 1989 *Molecular Cloning 2nd Edition,* CSH Press.

Synthesis of cDNA was carried out using M-MLV RNaseH reverse transcriptase (Bethesda Research Lab, Gaithersburg, Md.) according to the protocols described by the vendor. The first strand reaction was primed with an oligo dT$_{15}$ primer (Pharmacia) and also included 8 units of RNasin (Promega, Madison, Wis.) per 5 $\mu$g of poly A+ RNA. Second strand synthesis was directed by *E. coli* DNA polymeraseI, *E. coli* RNaseH, and *E. coli* DNA Ligase (all from BRL) according to the vendor's protocol. To facilitate cloning, the cDNA was treated with T4 DNA polymerase (BRL) to produce flush ends and methylated with EcoRI methylase (BRL). These steps were performed in accordance with protocols supplied by the enzyme vendor. The cDNA was then extracted two times with one volume of a 1:1 mixture of phenol and chloroform and the aqueous fraction precipitated with ½ volume of 7.5 M NH$_4$Ac and 3 vol of ethanol at room temperature. The precipitate was recovered by centrifugation for 15 min at room temperature, at 16,000×g, washed with 70% ethanol, vacuum dried and resuspended in 50 $\mu$l, 50 mM Tris-HCl (7.6), 10 mM MgCl$_2$, 1 mM ATP, 1 mM DTT, 5% PEG8000, containing 500 picomole phosphorylated linker (CCCGAATTCGGG, Pharmacia) (SEQ ID NO:9) and 3 units of T4 DNA ligase (BRL). Linker ligation was carried out at 16° C. overnight (~16 h). The reaction mixture was extracted with phenol/chloroform and precipitated as above. The washed pellet was dried and resuspended in 50 $\mu$l EcoRI digestion buffer (100 mM Tris-HCl (7.5), 5 mM MgCl$_2$, 50 mM NaCl and 0.025% Triton X-100) to which 400 units of EcoRI (New England Biolabs, Beverly, Mass.) was added. The reaction was incubated at 37° C. for 2 h. Following precipitation (as above) the pellet was resuspended in EcoRI digestion buffer and a second round of EcoRI digestion was performed as described above. This reaction was precipitated and resuspended in 40 $\mu$l 10 mM Tris-HCl (8.0), 1 mM EDTA, 100 mM NaCl. This cDNA, which now contained EcoRI-digested linkers, was size fractionated by centrifugation through a sephacryl S-300 (Pharmacia) spin column at about 1100 g for 5 min. The flow through from this column was collected, ethanol precipitated as above, and resuspended in 10 mM Tris-HCl (8.0), 1 mM EDTA at a concentration of about 0.1 $\mu$g/ml.

A cDNA library was constructed in the $\lambda$ZapII (Stratagene, La Jolla, Calif.) cloning vector. Typically 1 $\mu$g of EcoRI-digested and phosphatased vector arms (purchased from Stratagene) were ligated to 0.1 $\mu$g of EcoRI Tinkered cDNA in a 5 $\mu$l ligation using about 3 Weiss units T4 DNA ligase (NEB) in 50 mM Tris-HCl (7.6), 7 mM MgCl$_2$, 1 mM DTT, 5% PEG8000 and 1 mM ATP. Ligations were carried out at 16° C. overnight. Ligations were packaged in Giga-packII Gold packaging extracts (purchased from Stratagene) according to the protocol provided by the vendor. Libraries were plated for titering and screening on the XL1-Blue host provided by Stratagene.

From one such ligation and packaging, about 270,000 plaque forming units were plated out on a total of 12, 150 mm diameter, petri plates. Duplicate nitrocellulose filter lifts were prepared from these plates after the procedures described by Maniatis et al. The filters were hybridized to the following $^{32}$P-labeled degenerate oligonucleotide (SEQ ID NO:7) (I=inosine):

```
5' > CCIGATAAACAAGCIGCIGC > 3'
         C        G  G
```

This sequence is based on the amino acid sequence (FIG. 8)(SEQ ID NO:1) obtained around the amino-terminus of purified GDNF (SEQ ID NO:10) as described in Example 1 above:
Pro-Asp-Lys-Gln-Ala-Ala-Ala
The oligonucleotide was labeled with $^{32}$P derived from $^{32}$P-ATP (Amersham, Arlington Heights, Ill.) using T4 polynucleotide kinase (Pharmacia or United States Biochemical, Cleveland, Ohio). Hybridization reactions were carried out in 6× SSPE, 0.1% SDS, 0.1 mg/ml tRNA (SIGMA, St. Louis, Mo.), and 2× Denhardt's (0.4 mg/ml each: ficoll, polyvinylpyrrolidine, BSA fraction V) reagent, at 50° C. overnight (about 16 h). The hybridization solution contained 2–3×10$^6$ cpm of labeled oligo per ml of solution. Following hybridization, filters were washed twice at room temperature in 2× SSPE, 0.1% SDS and twice in the same solution pre-heated to 50° C. The filters were allowed to air dry and exposed to film for 7 days at −70° C. using intensifying screens.

The developed films were examined to identify plagues which hybridized to the screening oligonucleotide. In this primary screen, 24 putative duplicate positives were identified. Areas of the library plates corresponding to the positive signals were excised, resuspended and replated for a second round of screening via the hybridization procedure detailed above. In this second screen, 8 of the original 24 retested as positives, while 16 gave negative results. These eight positives were plaque purified through 1 or 2 additional rounds of hybridization and six of these were subsequently analyzed by DNA sequencing to determine if they contained DNA sequences that could encode GDNF.

The phagemid portion of the λZapII phage, which contains the cloned inserts, is referred to as pBluescript SK−. pBluescript SK− phagemid was excised from each of the λZapII recombinants that hybridized to the oligonucleotide probe. The procedure for in vivo excision of the recombinant pBluescript SK− plasmid from the λZapII vector is given in detail by the vendor protocols. Briefly, coinfection of λZapII and an M13 "helper" phage results in packaging of a single-stranded DNA copy of the recombinant pBluescript within an infectious M13 virion. When such a virion infects a sensitive cell, the single-stranded DNA is converted to a double-stranded DNA and is propagated vertically as a plasmid. Selection for this event is afforded by the ampicillin resistance gene encoded on pbluescript SK−. Thus *E. coli* XL1-Blue derivatives containing the "rescued" recombinant pBluescript SK− plasmid from each of the eight positive λZapII clones were readily obtained following the protocols described by Stratagene and employing the "helper" phage provided along with the λZapII vector.

For DNA sequencing, double-stranded plasmid DNA was prepared from six of these recombinant plasmids by a "mini-prep" procedure based on Birnboim and Doily 1979 *NAR* 7:1513–1523. DNA sequencing reactions using the dideoxy-chain terminating method were performed using these templates and the screening oligo as the primer. Reagents for sequencing were obtained from United States Biochemical as a kit (Sequenase Version 2.0) and sequencing procedures were carried out according to the protocols provided by the vendor. One clone, pBluescript SK-76.1, derived from the clone λZapII76.1 gave the following sequence (SEQ ID NO:11):

```
5' > GAG AGG AAC CGG CAA GCT
                GCA GCT GCC AGC CCA > 3'
                 T   AA  TA TA     T
```

This sequence can be translated to give the following amino acid sequence (SEQ ID NO:12):
Glu-Arg-Asn-Arg-Gln-Ala-Ala-Ala-Ala-Ser-Pro
which matches the amino acid sequence determined for a region of the amino-terminus of GDNF commencing 5 amino acid residues carboxyterminal to the end of the amino acid sequence used to generate the screening oligo/sequencing primer. This result demonstrated that the cDNA clone contained in λZapII76.1 must encode a portion of, or all of, the GDNF protein purified from the B49 cell conditioned medium.

B. Nucleotide Sequence of the Region of the cDNA Clone λZapII76.1 that Includes the Coding Sequence of GDNF The nucleotide sequence of the first 877 base pairs of the 5' end of the cDNA clone was determined. This region was found to contain an open reading frame (ORF) of 227 amino acids that includes the amino acid sequence obtained for the amino-terminus of purified GDNF and a sequence that is consistent with the internal peptide derived by cleavage of purified GDNF. The carboxyterminal 134 amino acids predicted for this ORF comprise the predicted amino acid sequence of the purified mature GDNF protein. The preceding 93 amino acids include a potential initiating ATG codon followed by a putative secretion signal sequence and contain potential proteolytic processing sites for cleavage of a precursor or "pre-pro" form of the protein to generate the mature, purified form of GDNF described above in Example 1.

Template DNA for sequencing reactions included single-stranded and double-stranded versions of the plasmid pBluescript SK-76.1 DNA. Double-stranded DNA was prepared from cultures of XL1-Blue (pBluescript SK-76.1) by a "boiling prep" procedure (*Anal. Biochem* 114:193:97) and banded in a CsCl density gradient. Single-stranded template was produced by infection of XL1-Blue (pBluescript SK-76.1) with a "helper" M13 phage supplied by the vendor (Stratagene) using the relevant protocols supplied along with the phage. Single-stranded oligonucleotide primers of 15 to 23 nucleotides in length were synthesized on an Applied Biosystems (Foster City, Calif.) DNA Synthesizer, model 380A synthesizer and generally used without purification. The sequence determination was performed using the dideoxy-chain termination method. Reagents used were included in the Sequenase Version 2.0 kit (United States Biochemical) and used in accordance with the protocols supplied by the vendor.

The nucleotide sequence of the first 877 nucleotides of the 5' end of the cDNA clone λZapII76.1, which contains the coding sequence for the purified mature GDNF protein is shown in FIG. 13 (SEQ ID NO:3) along with the inferred amino acid sequence of a 681 base pair open reading frame (ORF) that is found within this sequence. The sequence corresponding to purified mature GDNF starts at position 281 with a serine residue, and is shown in FIG. 14 (SEQ ID NO:4). The DNA sequence obtained for this region predicts an amino acid sequence which agrees perfectly with the first 23 residues of amino acid sequence observed at the amino-terminus of purified GDNF (see Example 1).

Based on an analysis of the gene as depicted in FIG. 13, it is likely that GDNF is initially translated as a pre-pro GDNF polypeptide and that proteolytic processing of the signal sequence and the "pro" portion of this molecule result in production of the form of GDNF that is purified from B49 cell conditioned medium. The most likely site of translation initiation for such a pre-pro form is the ATG codon that occurs at position 50 in the sequence of FIG. 13 (SEQ ID NO:3).

C. Cloning the Human Gene that Encodes GDNF

The amino acid sequences of many neurotrophic factors are highly conserved across a variety of mammalian species (Hallböök, et al. 1991 Neuron 6:845–858; McDonald, et al. 1991 BBA (in press)). As a consequence of the conservation of the amino acid sequences there is considerable conservation of the nucleotide sequences of the genes that encode these proteins. Therefore, it is generally true that the gene encoding a neurotrophic factor in one mammalian species can cross-hybridize (i.e. form a stable double-stranded DNA hybrid) with the genes encoding that factor in other mammalian species under appropriate annealing conditions. This property was used to identify cloned human DNA segments that include the gene for GDNF.

A human genomic library constructed in the vector λFIXII was purchased from Stratagene (catalog #946203) and screened using a $^{32}$P-labeled probe derived from the rat cDNA clone of GDNF (pBluescript SK-76.1) described above in Example 2B. The probe consisted of about 250 bp of coding sequence from the mature GDNF by specific amplification using the polymerase chain reaction (Saiki et al. 1985 Science 230:1350) and was produced as follows. A 50 μl or 100 μl PCR reaction was performed using <1ng λZapII76.1 DNA as template and 10–20 pmol each of two oligonucleotide primers based on sequence from rat GDNF. One oligo was the "screening oligo" (also termed DHD-21) described in Example 2A above, while the second oligo (DHD-26) (SEQ ID NO:13) had the sequence:

```
5' > AAATTTTTIAAIATTTTATC > 3'
        GG  C     G    C G
``` which is based on the amino acid sequence (Asp-Lys-Ile-Leu-Lys-Asn-Leu) (SEQ ID NO:14) obtained from an internal peptide product of cleavage of GDNF (see Example 1). The reaction was carried out in 10 mM Tris-HCl (pH 8.3 at 25° C.), 50 mM KCl, 1.5 MM MgCl$_2$, 10 μg/ml BSA (Promega R3961), 0.2mM each dNTPs (Pharmacia), using 2.5–5μ of Polymerase (USB). The reaction consisted of 30 cycles of: 95° C. for 1 minute, 44° C. for 1½ minutes and 72° C. for 1½ minutes. The product of this reaction was observed by agarose gel electrophoresis to be about 250 bp which is consistent with the positions of the two primers in the cDNA sequence shown in FIG. 13. This unlabeled fragment was eluted from the gel by centrifugation with an Ultrafree-MC Filter Unit (Millipore, Bedford, Mass.) according to the vendor protocols, and used as template in subsequent PCR labeling reactions employing the same two oligo primers. These reactions were performed under identical conditions except that the concentration of cold dCTP was reduced to 12.5 μM and 2.5 μM 3000–5000 Ci/mmol α-$^{32}$P dCTP (AMERSHAM) was added to the reaction. Products of the labeling reaction were passed over a BioSpin 6 spin column (BioRad, Richmond, Calif.). The flow-through from this column was used as the probe to screen the human genomic library.

The library was plated out using the E. coli strain PLK17 provided by STRATAGENE. Twenty-four 150 mm petri plates each containing approximately 50,000 plaques were prepared. Duplicate nitrocellulose filter lifts were prepared from each plate according to the procedures described by Maniatis et al. supra. These forty-eight filters were probed with 250×10$^6$ cpm of the PCR probe (denatured by treatment with 0.5 N NaOH) described above in 250 ml 6× SSPE, 0.1% SDS, 2× Denhardt's reagent, 0.1 mg/ml tRNA and 30% formamide (USB) at 42° C. overnight (~16 h). Filters were then washed twice in 250 ml 2× SSPE, 0.1% SDS at room temperature and twice in 1.6 l 0.1× SSPE, 0.1% SDS preheated to 50° C. The filters were allowed to dry at room temperature and placed under film for 6 days at −70° C. with intensifying screens. Films were developed and scored. Six strong duplicating positives were observed. Areas of the library plates corresponding to the positive signals were excised, resuspended, and replated for a second round of screening via the above detailed hybridization procedure. All six retested as positive and were plaque-purified via one additional round of plating and hybridization.

It is a matter of routine operations for one skilled in the art to subclone and sequence the segment of DNA around the region that hybridizes to the probe, and thus determine all or part of the sequence of the human gene for GDNF. If the entire human GDNF gene is not represented in these clones, it is also a routine matter to "walk" along the genome and clone overlapping segments of DNA around this region to obtain and sequence any remaining portion of the gene.

The above noted procedures and a variety of others that would be obvious to one skilled in the art could be applied to screen other human gene libraries. For example using the above described probe and hybridization protocol, a human cDNA library was screened that was constructed from A$^+$ RNA extracted from the human putamen. This library, contained in the cloning vector λgt10, was purchased from Clontech (Palo Alto, Calif.) (catalog #HL1092a, Lot #1561). This library was plated (Σ about 250,000 plaques) on E. coli LE392 (Maniatis et al. supra) at a density of about 20,000 plaques per plate and screened by hybridization under the conditions described above. Following hybridization, filters were washed twice at room temperature in 0.2× SSPE, 0.1% SDS and twice in 0.1× SSPE, 0.1% SDS preheated to 50° C. Filters were air-dried at room temperature and placed under film. After 3 days exposure at 70° C. with intensifying screens, films were developed and a duplicate positives were identified.

Six λFIX II clones from a human genomic library were identified by hybridization with a rat GDNF probe and plaque-purified to homogeneity (see above). Lysates of each phage were prepared by the method of Sambrook et al. (Molecular Cloning: A Laboratory Manual; 1989). DNA was prepared from these clones by the following procedure: DNAase I (Pharmacia) and RNAase A (Sigma) was added to 5 ml of each culture to give a final concentration of 1 μg/ml. The solution was incubated at 37° C. for 1 hour. Then 5 ml of 20% polyethylene glycol (Sigma), 2M NaCl, was added and the solution was incubated at 0° C. for 1 hour. The λphages were pelleted by centrifugation at 12,000×g for 10 min. The phage pellet was resuspended in 250 μl of TE (10 mm TRIS, pH 7.4, 1 mM EDTA) and sequentially extracted with an equal volume of: a. chloroform; b. phenol; c. a 1:1 mixture of chloroform and phenol; and d. chloroform. Ammonium acetate was added to give a final concentration of 0.25 M and the DNA was precipitated by the addition of 2 volumes of ethanol and centrifugation at 10,000×g. The DNA pellet was resuspended in TE.

DNA from each of the six λ isolates was digested with various restriction endonucleases and the fragments separated by electrophoresis through an agarose gel (Sambrook et al.). The DNA fragments were transferred to two identical nylon membranes (Schleicher and Schuell) and hybridized with radiolabeled probes from rat GDNF. In rat GDNF, there is an Eco R1 site between nucleotides 356 and 357 (following the numbering of FIG. 13). This cleaves within the coding sequence of mature GDNF. To determine whether the human genomic GDNF clones have a site at an homologous position, Eco R1 was used as one of the restriction endonucleases for digesting the human clones. Specific radiolabeled probes were made for regions of the gene either upstream (probe 1) or downstream (probe 2) of the Eco R1 site in rat GDNF. Probe 1 was 268 bp long and consisted of 14 bp of 5' untranslated sequence of rat GDNF and 254 bp of coding sequence (amino acids 1 through 85). It was prepared by amplification of λZap II76.1 DNA using the polymerase chain reaction and the oligonucleotide primers PD1 (GACGGGACTCTAAGATG) (SEQ ID NO:15) and DHD23 (GCIGCIGC(C/T)TG(T/C)TT(A/G)TCIGG) (SEQ ID NO:16). The reaction conditions for preparing the probe are as described above except that the reaction consisted of 30 cycles of: 95° C. for 1 minute, 50° C. for 1½ minutes and 72° C. for 1½ minutes. Probe 2 was 195 bp long and consisted of 17 nucleotides of 3' untranslated sequence of rat GDNF and 178 bp of coding sequence (amino acids 153 through 211). It was prepared using the polymerase chain reaction and oligonucleotide primers LF2 (CGAGACAATGTACGACA) (SEQ ID NO:17)and PD2 (CTCTGGAGCCAGGGTCA) (SEQ ID NO:18) and λZAPII76.1 as the DNA template. The reaction conditions were the same as for probe 1.

Five of the six λ clones gave identical hybridization patterns. Probe 1 hybridized to an approximately 700 bp Eco R1 fragment and probe 2 hybridized to an approximately 2.8 Kb Eco R1 fragment. The fact that the two probes hybridized to two different Eco R1 DNA fragments strongly suggested that the human GDNF gene contains an homologous Eco R1 site. The 700 bp and the 1.8 Kb Eco R1 fragments were subcloned separately into Bluescript SK– (Strategene). Nucleotide sequences of these two fragments were determined as described in Example 2B. The sequence of these DNA fragments is shown in FIG. 19 (SEQ ID NO:5). From the sequence it is clear that there is an intron preceding amino acid 52 of pre-proGDNF. There is no intron in the portion of the gene that codes for mature human GDNF. The predicted amino acid sequence of mature human GDNF is 93% homologous to mature rat GDNF. This is approximately the same degree of amino acid sequence homology found among rat and human proteins for other neurotrophic factors (Amino acid sequence homology between rat and human CNTF is 83%; McDonald et al. BBA (1991) (in press). Amino acid sequence homology between rat and human NGF is 95%, BDNF is 100%, and NT-3 is 100%; Hallbook et al. 1991 *Neuron* 6:845–855).

To obtain the complete human pre-proGDNF sequence, a radiolabeled hybridization probe may be made based on the sequence of human GDNF already obtained, and this probe may be used to screen human cDNA libraries. Because cDNAs are copies of the processed mRNA, the introns are not present and the sequence of the complete coding sequence can be obtained. Alternatively, now that the position of the intron relative to the coding sequence is known, a hybridization probe that is specific for sequences upstream of the intron can be made from the rat cDNA clone and this probe can be used to screen a genomic library for clones that contain the 5' exon(s).

D. Nucleotide Sequence Encoding the First 50 Amino Acids of Human Pre-proGDNF

As detailed in Example 2C, there is an intron that splits the nucleotide sequence corresponding to amino acid 51 of human pre-proGDNF. In order to obtain the sequence of this portion of the molecule, a human genomic library was screened with a probe derived from the amino-terminal coding sequence of rat pre-proGDNF and one hybridizing clone was sequenced and shown to contain the coding sequence of amino acids 1 through 50 of human pre-proGDNF as shown in FIG. 22 (SEQ ID NO:8)

For this library screen a PCR probe was synthesized as described in Example 2C. The oligonucleotide primers employed were:

PD1=5'>CCCGAATTCGACGGGACTCTAAGATG>3' (SEQ ID NO:19)

LFA=5'>CGGTGGCCGAGGGAGTGGTCTTC>3' (SEQ ID NO:20)

Conditions for the PCR (both "cold" and $^{32}$P-labelling) reactions were as described in Example 2B except that the reaction consisted of 25 or 30 cycles of: 95° C. for 1 min., 50° C. for 1½ min., and 72° C. for 1 min. The product of this reaction contains the first 122 bp of rat pre-proGDNF coding sequence and 14 base pair 5' to the putative initiator ATG (see FIG. 13 and SEQ ID NO:3). Conditions for screening the human genomic library with this probe were as described in Example 2C. The same filter lifts used to identity clones carrying sequences for mature human GDNF were washed twice for 15 min. in deionized-distilled $H_2O$ heated to boiling, probed overnight, and washed according to the protocol described in Example 2C. The filters were exposed to film for 3 days at –70° C. with intensifying screens. When developed, numerous duplicate positives of varying intensities were observed. Twelve relatively strong positives were picked and 10 of these were plaque purified by successive rounds of hybridization under the screening conditions.

The cloned DNAs of these recombinant phages were analyzed by Southern blot hybridization. An approximately 1000 bp AluI fragment was found to hybridize to the screening probe and was subcloned into SmaI-digested pBluescript SK– to produce pBSSK-λ3AluI. This cloned AluI fragment was further subcloned to facilitate sequencing of the relevant DNA segment. Purified pBSSK-λ3AluI DNA was digested with a series of restriction enzymes that cleave the vector only once (within the polylinker region) and the digestion products were analyzed by agarose gel electrophoresis. Two restriction enzymes (PstI and SacII) were thus identified that cleaved once within the cloned DNA. FIG. 22 shows a map of SacII and PstI sites. Southern blots revealed that the region of the cloned segment that hybridized to the screening probe was located between the SacII and PstI sites of the cloned AluI segment. Therefore, for sequencing, two deletion derivatives of pBBSK-λ3AluI were constructed. In one instance the small, about 300 bp, PstI fragment was deleted as follows: The plasmid was digested with PstI and the digest was ligated and transformed into *E. coli*. Transformants were screened for those lacking the small PstI fragment. In parallel, the 300 bp SacII fragment was similarly deleted from pBSSK-λ3AluI to produce a second deletion derivative. These two deletion plasmids were used as templates for sequencing reactions. Sequencing was carried out as described in Example 2B.

FIG. 22 (SEQ ID NO:8) presents 233 base pairs of the sequence thus obtained. This sequence contains a region of 151 bp that exhibits a very high degree of homology with the first 151 bp of coding sequence for rat pre-proGDNF; 88% identity at the amino acid level and 95% identity at the DNA level. Therefore, it is concluded that this region is part of the exon that carries the coding sequence of the amino-terminal 50 residues of the human pre-proGDNF and the first nucleotide of the codon for residue 51. The sequence immediately 3' to this 151 bp sequence is homologous to the consensus sequence for the 5' end of mammalian introns [Shapiro and Senapathy 1987 Nucl. Acids Res. 15:7155–7174]. The sequence immediately 5' to the putative initiator ATG shows strong homology to the rat sequence for 28 bp; 27 of 28 residues are identical. At this point the upstream sequence diverges sharply. The sequence around the point of divergence shows considerable homology to the consensus sequence for the 3' end of mammalian introns. (Shapiro and Senapathy, supra.) Thus, it seems likely that this is a splice site although there is no direct evidence for this. The open reading frame containing human pre-proGDNF extends at least 27 base pairs upstream of the initiator ATG. As discussed in the Detailed Description of Preferred Embodiments above, it is possible that other forms of a pre-proGDNF could be produced that would contain additional upstream amino acids. These forms might also be processed to produce the mature GDNF molecule that has been purified and sequenced (see Example 1).

The nucleotide sequences presented here and in Example 2C, contain the entire coding sequence for a human pre-proGDNF that exhibits extensive homology to the rat pre-proGDNF which has been successfully expressed in mammalian cells (see Example 5) to produce active rat GDNF.

Example 3

Use of GDNF to Prevent Experimental Parkinsonism

This example describes methods for creating experimental Parkinsonism in monkeys by appropriate administration to the animals of the neurotoxin MPTP (1-methyl-4-phenyl-1,2,3,6 tetrahydro-pyridine). It also describes methods for administering GDNF to animals exposed to MPTP in order to alleviate the development of Parkinsonism in such animals.

A. Administration of GDNF in monkeys treated with MPTP to produce experimental Parkinsonism A stainless-steel cannula may be implanted into the right lateral ventricle and connected to a subcutaneously-implanted osmotic minipump (Alzet 2002). The minipump contains GDNF at various concentrations or its diluent as a negative control. The pump delivers 0.5 µl/h for 14 days. Two days after the cannula-pump implant, monkeys (*Cebus apella*) receive an injection of 0.6 mg/kg of MPTP into the right carotid artery. Six weeks after the initial implant, animals are perfused with saline and the brain rapidly removed. The brain is dissected on ice and punches of tissue are removed from the caudate nucleus and putamen. The substantia nigra is placed in fixative. The caudate-putamen tissue is analyzed by HPLC-EC for dopamine, the substantia nigra is processed for tyrosine hydroxylase (TH) immunoreactivity.

B. Efficacy of GDNF

Degeneration of nigral dopaminergic nerve cells and their axonal projections to the caudate/putamen cause experimental Parkinsonism in this monkey model. There are several experimental indications that GDNF may prevent or reduce the severity of this neuronal degeneration. For example, GDNF may prevent the loss of TH positive nerve cell bodies in the substantia nigra. This indicates sparing by GDNF of nigral dopaminergic nerve cells from the toxic effects of MPTP. GDNF may also prevent the loss of TH positive fibers in the caudate/putamen. This indicates sparing by GDNF of the axonal projections of the nigral dopaminergic neurons from the toxic effects of MPTP. GDNF may also prevent the loss of dopamine content in the caudate/putamen. This indicates sparing from the toxic effects of MPTP by GDNF of the axons and their dopamine content extending from the nigral dopaminergic neurons to the caudate/putamen.

Example 4

Biological Activities and Potential Clinical Indications for GDNF

Purified GDNF increases dopamine uptake by dopaminergic neurons present in cultures of embryonic mesencephalic nerve cells in both enriched and defined culture media, as demonstrated in Example 1. This indicates that GDNF is a neurotrophic factor for these dopaminergic nerve cells. As such, GDNF may prove useful in treating the degeneration of these neurons that occurs in Parkinson's disease. In addition, GDNF may prove useful in treating improper functioning of other brain dopaminergic neurons. Such improper functioning may occur in schizophrenia and other disorders requiring treatment with neuroleptics.

A. Purified GDNF promotes the survival of parasympathetic and sympathetic nerve cells in culture 1. Assay for neuronal survival:

Materials

3-[4,5-dimethylthiazol-2 yl)-2,5-diphenyl-tetrazolium bromide (MTT) was obtained from Sigma chemical Co., St. Louis, Mo. Fetal calf serum was purchased from Hyclone Laboratories, Logan, Utah. Culture media and salt solutions were obtained from Irvine Scientific, Santa Ana, Calif. Culture dishes were obtained from Costar, Cambridge, Mass. Utility grade pathogen-free fertile chick embryo eggs were obtained from Spafas, Roanoke, Ill.

Assay

Cultures of primary chick embryo ciliary ganglia and sympathetic chain ganglia were prepared as previously described (Collins 1978 *Develop. Biol.* 65:50; Manthorpe et al. 1986 *Develop. Brain Res.* 25:191). Briefly, ciliary or sympathetic ganglia were removed from fertile, pathogen free chicken eggs that had been incubated for 8 and 10 days, respectively, at 38° C. in a humidified atmosphere. The ganglia were chemically dissociated by exposure first to Hanks' Balanced Salt Solution without divalent cations, containing 10 mM HEPES buffer pH 7.2 for 10 min at 37° C., and then by exposure to a solution of 0.125% bactotrypsin 1:250 (Difco, Detroit, Mich.) in Hanks' Balanced Salt Solution modified as above for 12 min at 37° C. Trypsinization was stopped by addition of fetal calf serum to a final concentration of 10%.

After this treatment, ganglia were transferred to a solution consisting of Dulbecco's high glucose Modified Eagle Medium without bicarbonate containing 10% fetal calf serum and 10 mM HEPES, pH 7.2 and were mechanically dissociated by trituration approximately 10 times through a glass Pasteur pipet whose opening had been fire polished and constricted to a diameter such that it took 2 seconds to fill the pipet.

The dissociated ganglia were then plated in culture medium (Dulbecco's Modified Eagle Medium supplemented with 10% fetal calf serum, 4 mM glutamine, 60 mg/L penicillin-G, 25 mM HEPES, pH 7.2) in 100 mm diameter tissue culture dishes (40 dissociated ganglia per dish) for three hours. This preplating was done in order to separate the nonneuronal cells, which adhere to the dish, from the nerve cells, which do not adhere. After three hours, the nonadherent nerve cells were collection by centrifugation, resuspended in culture medium, and plated in 50 µl per well onto half area 96 well microtiter tissue culture plates at a density of 1500 nerve cells per well. The microtiter wells had been previously exposed to a 1 mg/ml solution of poly-L-ornithine in 10 mM sodium borate, pH 8.4 overnight at 4° C., washed in distilled water and air dried.

Ten µl of a serial dilution of the sample to be assayed for neurotrophic activity was added to each well and the dishes were incubated for 20 hours at 37° C. in a humidified atmosphere containing 7.5% $CO_2$. After 18 hours for ciliary and 40 hours for sympathetic ganglia, 15 µl per well of a 1.5 mg/ml solution of the tetrazolium dye MTT in Dulbecco's high glucose Modified Eagle Medium without bicarbonate containing 10 mM HEPES, pH 7.2, was added and the cultures placed in the 37° C. incubator for 4 hours. Then, 75 µl of a solution of 6.7 ml of 12 M HCl per liter of isopropanol was added and the contents of each well triturated 30 times to break open the cells and suspend the dye. The absorbance of 570 nm was determined relative to a 690 nm reference for each well using an automatic microtiter plate reader (Dynatech, Chantilly, Va.). The absorbance of wells which had not received any neurotrophic agent (negative controls) was subtracted from the absorbance of sample-containing wells. The resulting absorbance is proportional to the number of living cells in each well, defined as those nerve cells capable of reducing the dye. The number of trophic units of neurotrophic activity was defined as the reciprocal of the dilution that gave 50% of maximal survival of nerve cells. Specific activity was determined by dividing the number of trophic units by the amount of protein present in the sample.

Results

Figure 15:
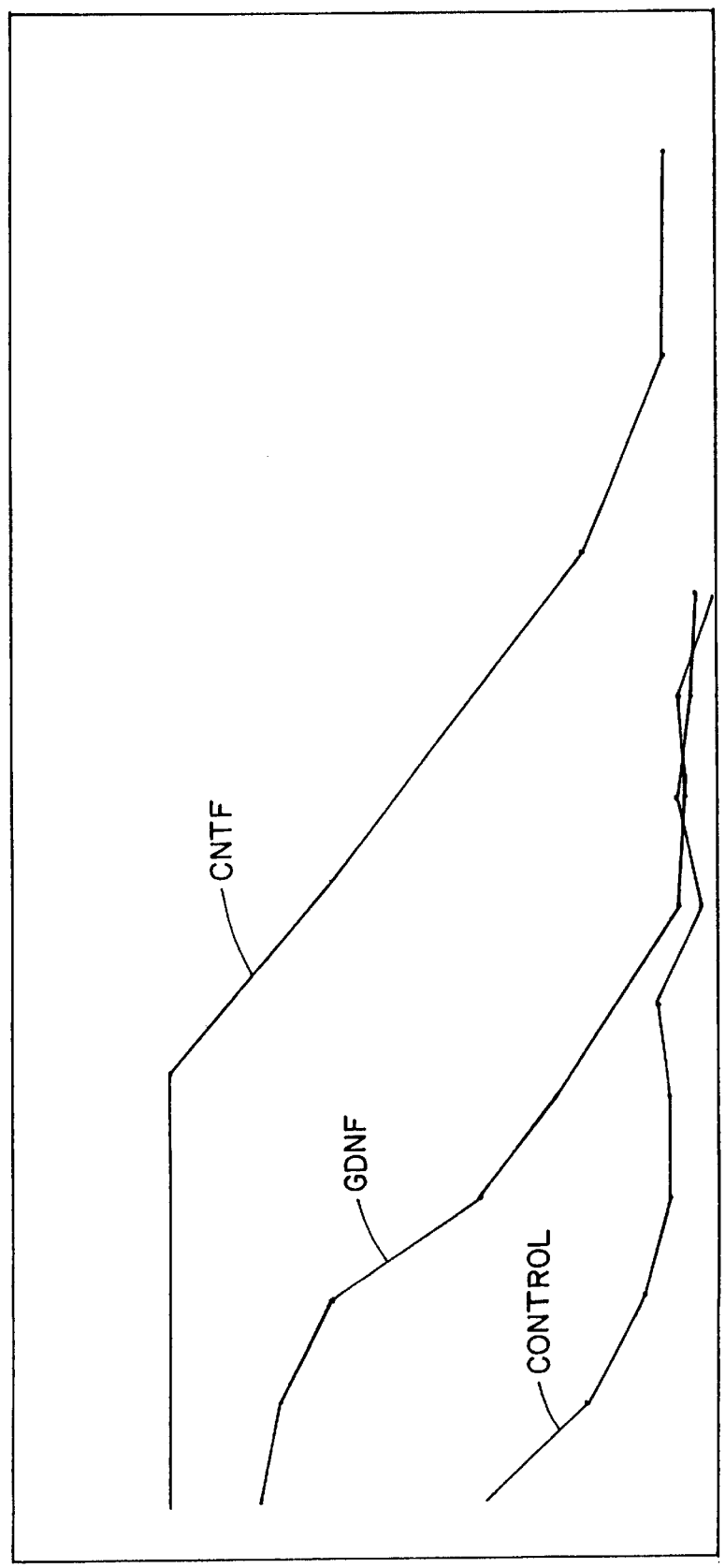
FIG. 15 depicts the results of purified B49 cell GDNF and human recombinant CNTF to promote the survival of parasympathetic neurons from chick embryo ciliary ganglia. Increasing optical density on the Y-axis represents increasing neuronal survival. The X-axis represents decreasing concentrations of each neurotrophic factor. The curve labeled control is equal volumes of inactive HPLC fractions adjacent to those containing the GDNF used to generate the curve labeled GDNF.
Figure 16:
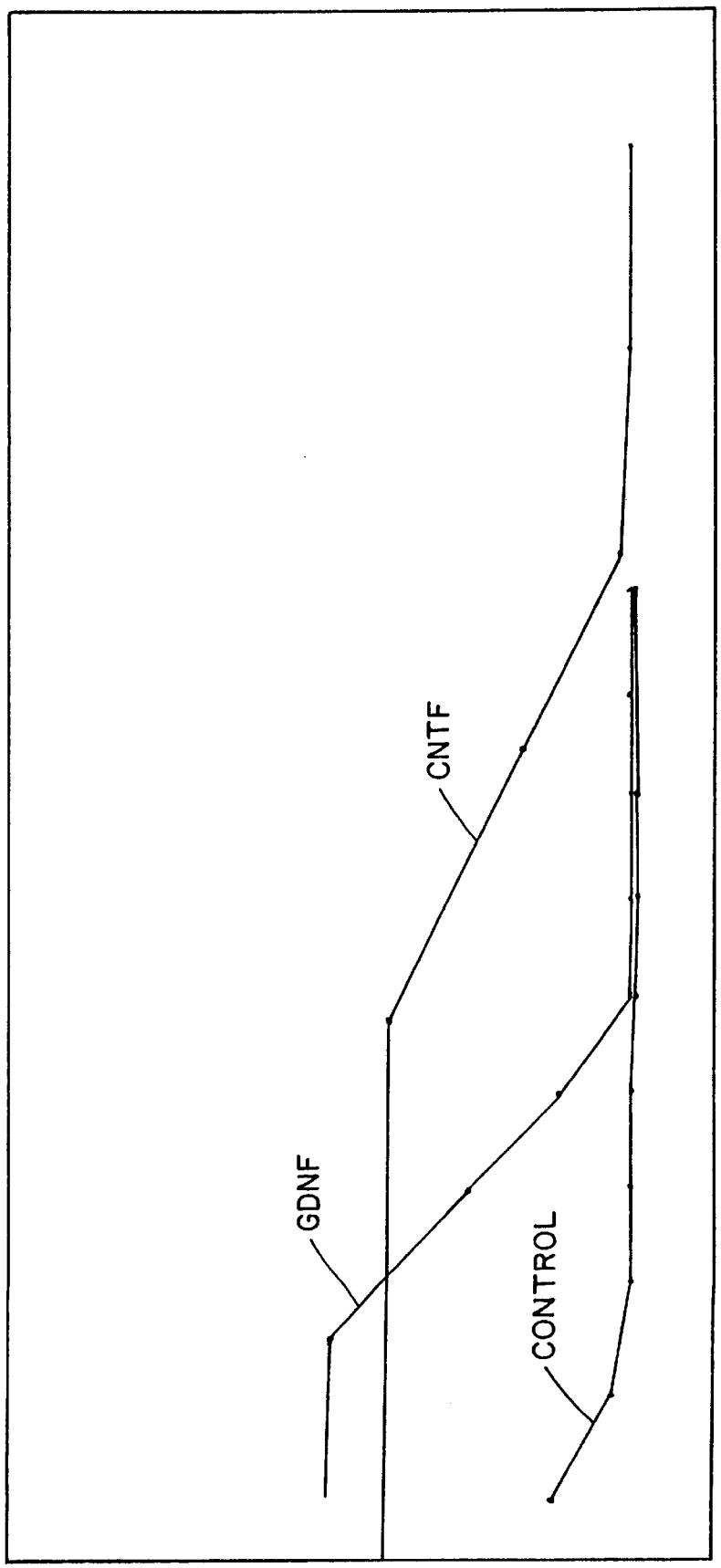
FIG. 16 depicts the results of purified B49 cell GDNF and human recombinant CNTF to promote the survival of sympathetic neurons from chick embryo sympathetic chain ganglia. Increasing optical density on the Y-axis represents increasing neuronal survival. The X-axis represents decreasing concentrations of each neurotrophic factor. The curve labeled control is equal volumes of inactive HPLC fractions adjacent to those containing the GDNF used to generate the curve labeled GDNF.

As illustrated in FIG. 15, purified GDNF promotes the survival in culture of parasympathetic nerve cells from chick embryo ciliary ganglia. As illustrated in FIG. 16, purified GDNF also promotes the survival in culture of sympathetic nerve cells from chick embryo sympathetic chain ganglia.

These results indicate that GDNF acts as a survival factor for parasympathetic and sympathetic neurons. As such, it may be useful in treating various forms of nerve damage to the autonomic (i.e., parasympathetic and sympathetic) nervous system. Such damage may occur from metabolic conditions, such as diabetes or renal dysfunction. Such damage may also occur from treatment of patients with various chemotherapeutic agents, such as the cancer chemotherapeutic agents cisplatin and vincristine, or the AIDS chemotherapeutic agents, ddI and ddC. Such damage may also occur from genetic conditions, such as dysautonomia. Such damage may also occur from traumatic injury.

Example 5

Expression of Recombinant GDNF in Animal Cells

A. Construction of recombinant plasmids for COS cell expression

An approximately 1.5 kb SmaI fragment of pBluescript SK-76.1 that contains the entire GDNF coding sequence was subcloned into the plasmid vector pSG5 (Green et al. 1988 *Nucl. Acids. Res.* 16:369) which is designed for transient expression of cloned genes in cells expressing SV40 T antigen, such as COS cells.

The DNA sequence of the GDNF cDNA (FIG. 13) (SEQ ID No:3) and restriction endonuclease mapping identified a SmaI fragment delineated by one SmaI site located in the polylinker of the vector (18 bp 5' to the 5' end of the cDNA clone) and one SmaI site (~1500 bp distant) located within the cDNA clone approximately 800 bp 3' to the end of coding sequence for mature GDNF. This SmaI fragment was cloned into pSG5 as follows. Purified pSG5 plasmid DNA (Stratagene) was digested with EcoRI and treated with calf intestinal alkaline phosphatase (CIAP), (Promega) according to the vendor protocols. Subsequently the vector was electrophoresed and eluted from an agarose gel. Purified pBluescript SK-76.1 plasmid DNA was methylated with EcoRI methylase, digested with SmaI and ligated with the EcoRI linker molecule described in Example 2A. Following EcoRI digestion and agarose gel electrophoresis, the approximately 1.5 Kb SmaI fragment of interest (now EcoRI methylated and linked) was eluted and ligated to the EcoRI digested and phosphatased pSG5 vector. Ligation products were used to transform competent *E. coli* XL1-Blue using the $CaCl_2$ procedure (Maniatis et al. supra). Ampicillin-resistant transformants were selected and analyzed for recombinant plasmids by restriction endonuclease digestion and agarose gel electrophoresis. Digestion with EcoRI indicated that most transformants contained plasmids carrying the desired insert. Digestion with BamHI identified the orientation of the cloned GDNF gene relative to the SV40 promoter present in the vector (note the BamHI site at position 15 in the sequence in FIG. 13). Both orientations were obtained.

Two transformants were chosen for further analysis; one contained a plasmid, termed pSG5::rGDNF-7, carrying the GDNF gene in the proper orientation for it to be expressed in RNA transcripts initiated at the SV40 promoter, while the second contained a plasmid, termed pSG5::rGDNF-4, carrying the GDNF gene in the opposite orientation; in which RNA transcripts initiating at the SV40 promoter will not express GDNF. Purified preparations of both of these plasmids were prepared by CsCl density gradient centrifugation for use in COS cell expression experiments.

B. Expression of GDNF in COS-7 cells

Plasmid DNA from these constructs was prepared by the method of alkaline lysis followed by CsCl density centrifugation (Maniatis et al., supra). This DNA was transfected into COS-7 cells by the method of Sompayrac and Danna (1981 *Proc. Natl. Acad, Sci, USA* 78:7575–7578). As a control, equivalent COS cell cultures were transfected with plasmid vector DNA containing the GDNF insert in the opposite orientation, which would not allow expression of the GDNF protein. Per 100 mm culture dish, 30 µg lipofectin and 0.3–1 µg plasmid DNA were used.

After transfecting for 24 hours, the medium was aspirated off and replaced with OptiMEM I±3% FCS. Cultures were incubated for 48 hours and harvested as follows:

a) the medium (conditioned medium or CM) was drawn off and stored at −80° C.;

b) 5 ml of PBS+2.5 mM EDTA was added to the cell lawn and held at 25° C. for 3 minutes; and, then the cells were pipetted off the dish and centrifuged at 1000×g for 5 minutes. The supernatant was removed and the cell pellets were stored at −80° C.

The CM was concentrated 30-fold on Centricon 10 concentrators and assayed for bioactivity. The cell pellets were sonicated in 500 µl 10 mM EDTA, pH 7.0, plus 1 mM benzamidine, 100 µM PMSF, 1 mM E-amino-N-caproic acid. The cell lysates were centrifuged at 14,000×g for 5 minutes and the supernatants assayed for bioactivity.

C. Bioassay of expressed GDNF

Figure 17:
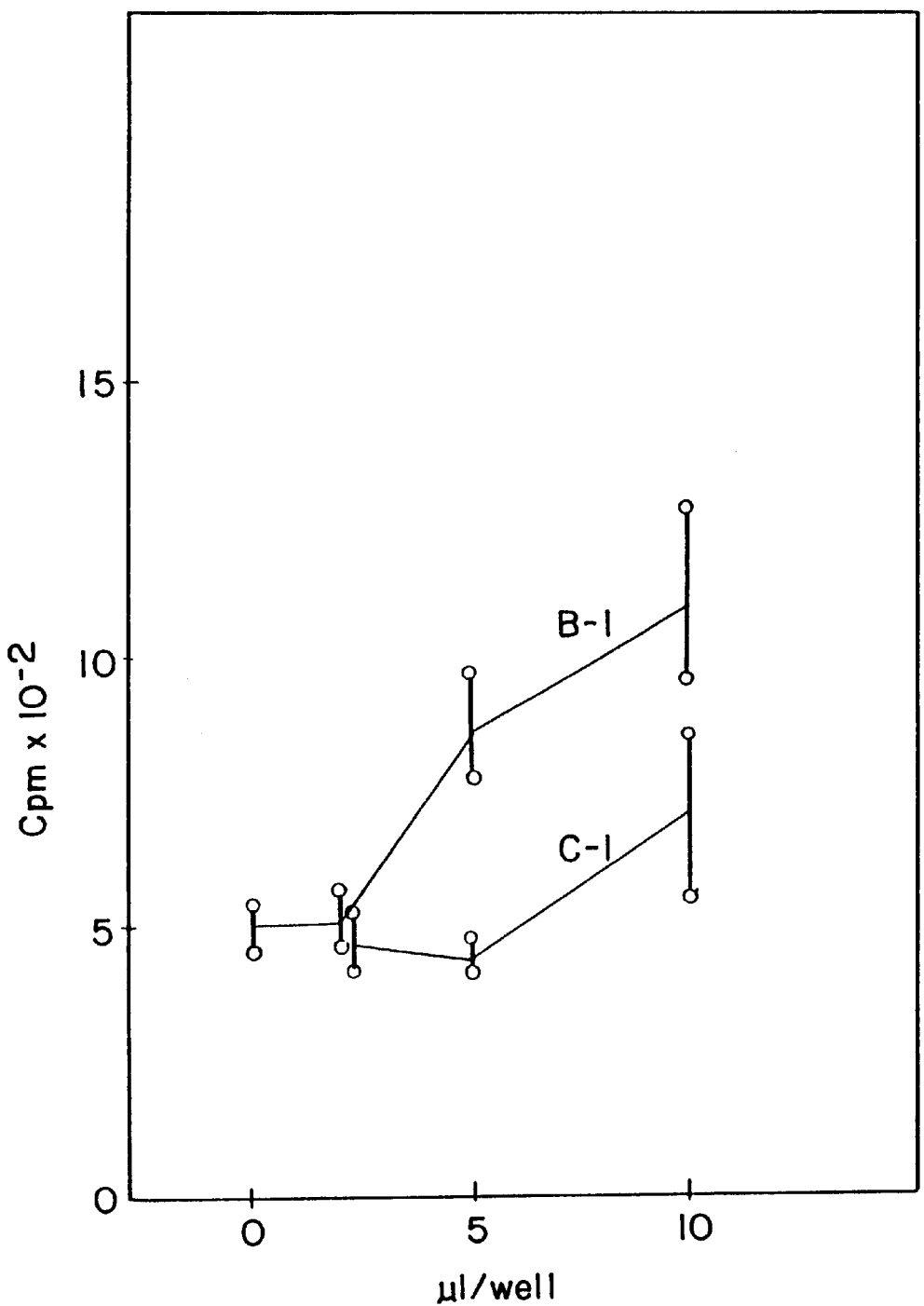
FIG. 17 depicts the results of bioassay of COS cell conditioned media for ability to increase dopamine uptake by mesencephalic dopaminergic neurons in culture. The Y-axis presents the amount of radiolabeled dopamine taken up versus increasing amounts of concentrated COS cell culture medium on the X-axis. The curve labeled B-1 represents the serum-free conditioned medium from COS cells transfected with the GDNF gene in the proper orientation for expression of GDNF. The curve labeled C-1 represents the serum-free conditioned medium from COS cells transfected with the GDNF gene in the opposite orientation, which prevents expression of GDNF.
Figure 18:
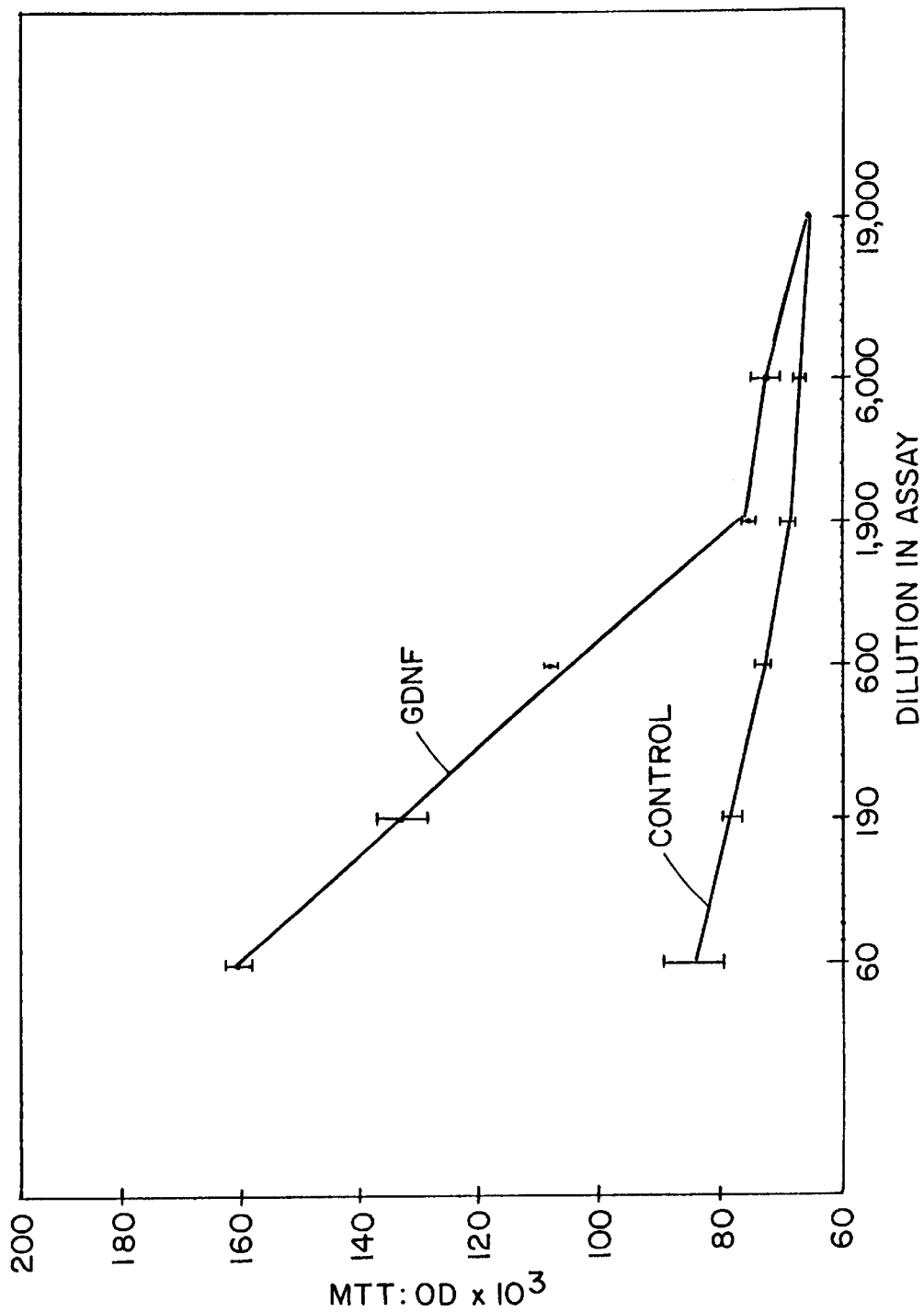
FIG. 18 depicts the results of bioassay of COS cell conditioned media for ability to increase survival in culture of sympathetic neurons from the sympathetic chain in chicken embryos. The Y-axis presents the amount of MTT dye reduced by the cultures and is proportional to neuronal survival. The X-axis represents increasing dilution of concentrated COS cell culture medium. The curve labeled GDNF represents the serum-free conditioned medium from COS cells transfected with the GDNF gene in the proper orientation for expression of GDNF. The curve labeled CONTROL represents the serum-free conditioned medium from COS cells transfected with the GDNF gene in the opposite orientation, which prevents expression of GDNF.

The cell lysate and culture media from COS cells transfected with GDNF-expressing and control plasmids (with the GDNF coding sequence in the incorrect orientation) were assayed for both the ability to increase dopamine uptake in cultures of mesencephalic neurons (see Example 1) and for the ability to increase the survival of sympathetic ganglia neurons (see Example 4). The COS cell culture medium (FIG. 17) and cell lysate (data not shown) increased dopamine uptake, as expected of GDNF. As shown in FIG. 18, the COS cell culture medium and cell lysate increased the survival of sympathetic chain neurons, as expected of GDNF.

These results clearly indicate that expression of the GDNF gene in an animal cell results in the production of a protein with the biological activities demonstrated for purified GDNF.

Example 6

Expression of Human GDNF in *E. coli*

A. Construction of a plasmid which codes for human GDNF

Using the sequence information of the human GDNF gene (Example 2C), synthetic oligonucleotides PD3 and PD4 were made as primers for the amplification of the human GDNF gene and its expression from a plasmid expression vector in *E. coli*. The sequences of oligonucleotides PD3 (SEQ ID NO:21) and PD4 (SEQ ID NO:22) are:

```
PD3: 5' CGCGGATCCAATAAGGAGGAAAAAAAATGTCACCAGATAAACAAAT 3'

PD4: 5' CGCGGTACCCAGTCTCTGGAGCCGGA 3'
```

Oligonucleotide PD3 is 46 nucleotides long. The 17 nucleotides at the 3' end are a perfect match to the human GDNF gene in the region that codes for the N-terminus of the mature protein. These 17 nucleotides are preceded by a translation initiation codon, ATG, so that synthesis of mature human GDNF will start at the correct amino acid in *E. coli* The other nucleotides are designed to provide other signals deemed necessary for good expression in *E. coli* as well as a BamH1 endonuclease restriction site necessary for construction of the GDNF expression plasmid.

Oligonucleotide PD4 is 26 nucleotides long. The 17 nucleotides at the 3' end are a perfect match to 17 nucleotides of the human GDNF gene 3' of the stop codon. This oligonucleotide also provides sequences necessary to reconstruct a KpnI restriction endonuclease site for construction of the GDNF expression plasmid.

The reaction conditions for the amplification of the human GDNF are as follows: the total reaction volume was 100 µl and contained 1 ng of a λDNA clone containing the human GDNF gene, 20 pmoles each of PD3 and PD4, 20 mM Tris-HCl pH8.8, 10 mM KCl, 6 mM $(NH_4)_2SO_4$, 1.5 mm $MgCl_2$, and 0.1% Triton X-100. The reaction mixture was heated to 95° C. for 5 minutes, cooled to 44° C., and 2 units of Pfu DNA polymerase (Stratagene) were added. The reaction consisted of 30 cycles of: 72° C. for 1½ minutes, 95° C. for 1 minute, and 44° C. for 1½ minutes. At the end of the reaction, $MgCl_2$ was added to a final concentration of 10 mM. 5 units of DNA polymerase I large (Klenow) fragment (Promega) were added, and the reaction incubated at 37° C. for 10 minutes. Then 10 µl of 3M NaAc and 220 µl of EtOH were added, and the solution was centrifuged at 12,000×g for 15 minutes to precipitate the DNA. The precipitated DNA was resuspended in 100 µl of 50 mM Tris-HCl (pH 8), 50 mM NaCl, 10 mM $MgCl_2$, 20 units of BamH1 and 20 units of KpnI and incubated at 37° C. for 1 hour. A DNA fragment of the correct size was identified after electrophoresis through an agarose gel and purified using an Ultrafree-MC Filter Unit (Millipore). This fragment was ligated into an *E. coli* expression vector, pT3XI-2, (described below). Ligation conditions were as follows: the total reaction volume was 5 µl and contained 10 ng of pT3XI-2 DNA linearized with KpnI and BamHI, 5 ng of the human GDNF DNA fragment as described above, 50 mM Tris-HCl (pH 7.6), 10 mM $MgCl_2$, 1 mM ATP, 1 mM DTT, 5% polyethlene glycol-8000, and 1 unit of T4 DNA ligase (Bethesda Research Laboratories). The reaction was incubated at 14° C. for 2 hours.

The vector pT3XI-2 was constructed in the following manner. The starting plasmid for this construction was plasmid pKK223-3 (Brosius and Holy, 1984) purchased from Pharmacia. Plasmid pKK223-3 carries a partial gene for tetracycline resistance. This nonfunctional gene was replaced by a complete tetracycline resistance gene carried on plasmid pBR322. Plasmid pKK223-3 was digested completely with SphI and partially with BamH1. A 4.4 kilobase pair fragment was gel purified and combined with a synthetic adapter (SEQ ID NO:23):

```
5' GATCTAGAATTGTCATGTTTGACAGCTTATCAT    3'
3'     ATCTTAACAGTACAAACTGTCGAATAGTAGC   5'
    BglII                          ClaI
``` and a 539 base pair fragment of DNA from a ClaI, SphI digest of the tetracycline resistance gene of pBR322 (PL Biochemicals, 27-4891-01). The resulting plasmid was designated pCJ1.

Next, a XhoI linker purchased from New England Biolabs was inserted into plasmid pCJ1's PvuII site to form plasmid pCJX-1. This insertion disrupts the rop gene which controls plasmid copy number. Next, an EcoRI fragment containing the lacI gene was purified from plasmid pMC9 (Calos et al., 1983), and then inserted into the XhoI site with XhoI to EcoRI adapters. The polylinker region in plasmid pKK223-3 was next replaced with a polylinker containing additional sites by cutting with EcoRI and PstI (SEQ ID NO:24):

```
5' AATTCCCGGG TACCAGATCT GAGCTCACTA GTCTGCA3'

3'    GGGCCC ATGGTCTAGA CTCGAGTGAT CAG   5'
```

The plasmid vector so obtained is designated pCJXI-1.

Finally, the tetracycline resistance gene was replaced with a similar gene which had the recognition sites for restriction enzymes HindIII, BamH1, and SalI destroyed by bisulfite mutagenesis. The following procedure was used to mutate the tetracycline resistance gene of pBR322. Plasmid pBR322 was cut with HindIII, then mutagenized with sodium bisulfite (Shortle and Botstein, 1983). The mutagenized DNA was ligated to form circular DNA, then cut with HindIII to linearize any plasmid that escaped mutagenesis. *E. coli* JM109 (Yanisch-Perron et al., 1985). Tetracycline-resistant plasmids were isolated and checked for loss of the HindIII site in the tetracycline resistance gene. Successfully mutated plasmid was designated pT1. A similar procedure was followed to mutagenize the BamHl site in pT1, yielding plasmid pT2. Plasmid pT2 in turn was mutagenized to remove the SalI site, forming plasmid pT3. A ClaI-StyI fragment of pT3 carrying the mutated tetracycline resistance gene was isolated and used to replace the homologous fragment of pCJXI-1 to form pT3XI-2. The mutated tetracycline resistance gene still encodes for a functional protein. Downstream of the tac promoter region, a polylinker was introduced which contains, among other sites, BamHl and KpnI restriction sites useful for cloning genes for expression in *E. coli*

After the 2 hour ligation of the vector with the human mature GDNF construct, 2 μl of the reaction mix was used to transform Epicurian Coli SURE® supercompetent *E. coli* cells (Statagene) according to the manufacturer's instructions. The DNA sequence of one of the recombinant plasmids was determined as described in Example 2B. The sequence confirmed that this plasmid contained the complete coding sequence of the human GDNF gene coding for mature human GDNF.

B. Expression of human GDNF in *E. coli*

The recombinant plasmid containing DNA sequences encoding human GDNF was transformed into *E. coli* strain JM107ϕrMCB0005, a T1 resistant variant of JM107 (Yanisch-Perron et al. (1985)), using the $CaCl_2$ method described in Sambrook et al. (1989). One of the recombinants was grown in 50 ml of LB media (Sambrook et al.) with 100 μg/ml ampicillin (Sigma) with shaking at 37° C. overnight. The next day the culture was diluted 1:70 in LB media with 100 μg/ml ampicillin and grown for 5 hours with shaking at 37° C. 20 ml of cells were harvested by centrifugation at 8,000×g for ten minutes. The pellet was resuspended in 4 ml of 10 mM EDTA pH 7.4. The cells were disrupted using a French Press Pressure Cell (SLM Instruments) at 18,000 psig. The lysate was centrifuged at 12,000×g for 15 minutes at 4° C. The pellet was resuspended in 10 mM EDTA. It has been found that relatively more GDNF accumulates if fermentation is allowed to take place at 42° C. rather than 37° C. or 30° C.

The presently preferred method for obtaining high levels of GDNF expression in *E. coli* using the recombinant plasmid described in Example 6A (in which the coding sequence for human mature GDNF is cloned in the expression vector pT3XI-2) is as follows. For a 10 l fermentation a 500 ml inoculum is grown in LB medium (pH 7) containing 15 μg/ml tetracycline at 37° C. in a 2 l baffled shake flask to an optical density ($A_{660}$) of between 2 and 3. This culture is used to inoculate 10 l of growth medium containing: 12 g/l tryptone, 24 g/l yeast extract, 25 g/l glycerol, 1.3 g/l $K_2HPO_4$, 0.4 g/l $KH_2PO_4$, 0.1 ml/l of 4:1 mixture of Macol19:GE60, and 15 mg/l tetracycline HCl. This culture is grown for approximately 12 to 18 hours at 42° C. to optical densities of approximately 12 to 20 ($A_{660}$). The pH of the fermentation is maintained at 7.0 and the dissolved oxygen is maintained at 30% of saturation. Post-fermentation, the culture is chilled at 4° C. and cells are harvested by centrifugation.

The production of human GDNF from this plasmid described above is not specific to this strain of *E. coli* but can be produced in any suitable strain. The plasmid has been transformed into two other strains of *E. coli,* JM108 (Yanisch Perron et al., 1985) and SURE® (Stratagene). In both of these strains a new protein band of the correct molecular weight has been visualized by Coomassie Blue staining after electrophoresis through a polyacrylamide gel.

An aliquot of the resuspended material was electrophoresed through a polyacrylamide gel. The gel was stained with Coomassie Blue. A protein of the expected molecular weight for GDNF (15,000 daltons) was present only in the cultures that contained the recombinant human GDNF plasmid but not in the cultures that contained vector pT3XI-2 alone. The recovered protein was subjected to standard amino terminal sequencing procedures, and the first 22 amino acids of this protein are identical to the amino acid sequence of human GDNF as shown in FIG. 19, confirming that human GDNF is being correctly expressed in *E. coli*.

C. Refolding and bioactivity of recombinant human GDNF produced in bacteria

Preparation of material for refolding. The *E. coli* transformant JM107 (pT3X12::huGDNF) was grown to stationary phase at 37° C. in a yeast extract (#0127-01 Difco Laboratories, Detroit, Mich.) and tryptone (#0123-05 Difco Laboratories, Detroit, Mich.) based complex medium (24 g/L yeast extract, 12 g/L tryptone, 5 g/L glycerol, 1.3 g/L $K_2HPO_4$, 0.4 g/L $KH_2PO_4$, 0.1 ml/L Macol 19/GE60 (4:1), 15 mg/L tetracycline) without IPTG induction. The cells were centrifuged at 16,000×g in a JA10 rotor at 4° C. for 20 minutes and the cell paste stored at 20° C.

The cells were processed as follows: 5 gm of cell paste was homogenized with 40 ml of 10 mM EDTA, pH 7.0 on ice using an OCI Instruments homogenizer. The slurry was French-pressed three times at 20,000 psi then centrifuged at 30,000×g in a JA 20 rotor for 10 minutes at 4° C. The supernatant was discarded and the pellet was homogenized and centrifuged as above. In one embodiment, the pellet from the re-extraction was homogenized with 40 mL of 25 mM Tris, pH 7.4, centrifuged as above, and the supernatant discarded. The pellet was homogenized with 20 mL of 50 mM Tris, pH 8.0, containing 8 M urea with or without addition of 30 mM 2-mercaptoethanol, centrifuged as above and the supernatant retained. The supernatant is referred to as the TU extract. In the preferred embodiment, the pellet was homogenized in 40 ml of 10 mM Tris, pH 8.0, containing 1 mM EDTA, 1% NP-40, centrifuged as above, and the supernatant discarded. The pellet was solubilized by sulfonylation as follows: The pellet was homogenized in 25 ml of 20 mM sodium phosphate, pH 7.4 containing 8 m urea, 100 mM sodium sulfite and 10 mM sodium tetrathionate. The sulfonylation was allowed to proceed at 4° C. overnight with stirring and then centrifuged at 16,000×g, 4° C., for 10 minutes to clarify the solution.

Figure 25:
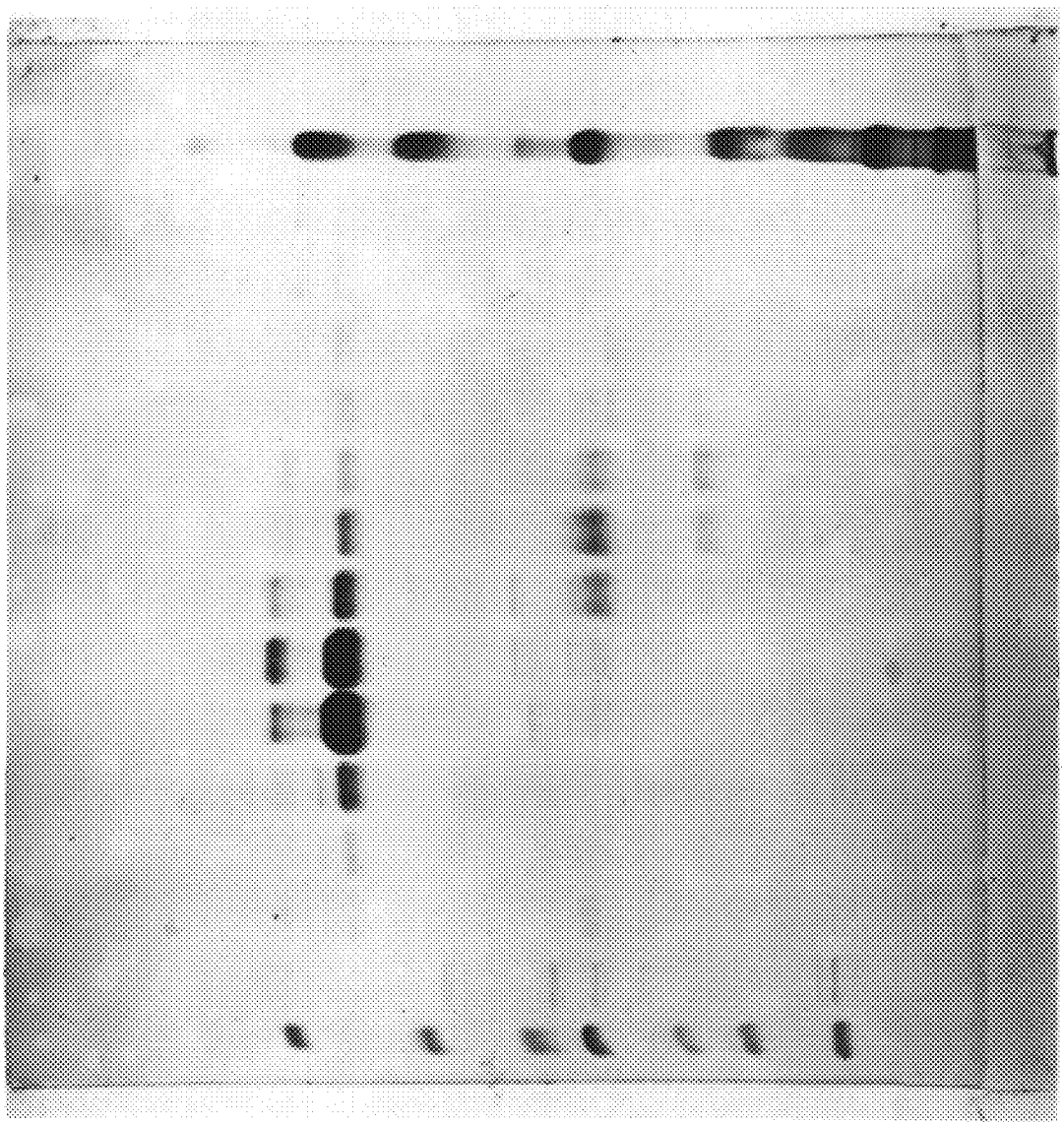
FIG. 25 depicts Coomassie Blue stained SDS-PAGE, run under reducing conditions, of fractions from chromatography of a bacterial extract containing unrefolded GDNF on an S-sepharose column prior to refolding (see Example 6C). Lanes 2–8 represent consecutive fractions from the column eluate. Fractions 3–5, enriched for GDNF, were pooled for refolding. Lane 1 is molecular weight standards (SDS-70L, Sigma).

Partial purification of TU extract prior to refolding. The TU extract was partially purified by ion exchange chromatography on S-Sepharose Fast Flow resin (Pharmicia). The column was equilibrated and run at room temperature in 25 mM Tris, pH 7.4, containing a 8 M urea and 30 mM 2-mercaptoethanol (buffer A). After loading the sample and washing with buffer A to baseline optical density, the column was eluted at 10% column volume per minute with 5 column volumes each of buffer A and 100 mM Tris, pH 9.0, containing 8 M urea, 500 mM NaCl, and 30 mM 2-mercaptoethanol (buffer B). Column fractions were monitored at 280 nM and analyzed by SDS-PAGE. GDNF eluted as the major protein peak at 60–70% of the gradient. Fractions enriched in GDNF were pooled for refolding (FIG. 25).

Partial purification of sulfonylated extract prior to refolding. The sulfonylated extract was partially purified by ion exchange chromatography on Q-Sepharose Fast Flow resin (Pharmicia). The column was equilibrated and run at 4° C. in 10 mM Tris, pH 8.0, containing 4M urea (buffer A). After loading the sample and washing with buffer A to baseline optical density, the column was eluted as 5% column volume per minute with 5 column volumes each of buffer A and 10 mM Tris, pH 8.0, containing 4M urea and 500 mM NaCl (buffer B). Column fractions were monitored at 280 nM and analyzed by SDS-PAGE. GDNF eluted at the major protein peak at 50% of the gradient. Fractions enriched in GDNF were pooled for refolding.

Refolding of partially purified TU extract. GDNF, partially purified as described above, was refolded as follows: To 4 ml of pooled column eluate containing GDNF at approximately 1 mg/ml, dithiothreitol was added to 5 mM. The tube was capped so as to exclude air and held at 25° C. for 15 minutes. Next, oxidized glutathione disodium salt was added to 15 mM, the tube capped again so as to exclude air, and held at 25° C. for 15 minutes. This solution was then diluted with 14 volumes of refold buffer (100 mM $Na_2HPO_4$, 10 mM ethanolamine, pH 8.3, containing 4 M urea; 5% polyethylene glycol 300; and 2 mM cysteine) and held under argon at 5° C. for 3 days.

Refolding of partially purified sulfonylated extract. GDNF, partially purified as described above, was refolded as follows: Pooled column eluate containing GDNF at approximately 3 mg/ml was diluted with 19 volumes of refold buffer (100 mM $Na_2HPO_4$ Tris, pH 8.3, containing 4 M urea; 5% polyethylene glycol 300; and 3 mM cysteine) and held under argon at 5° C. for 3 days.

Figure 26:
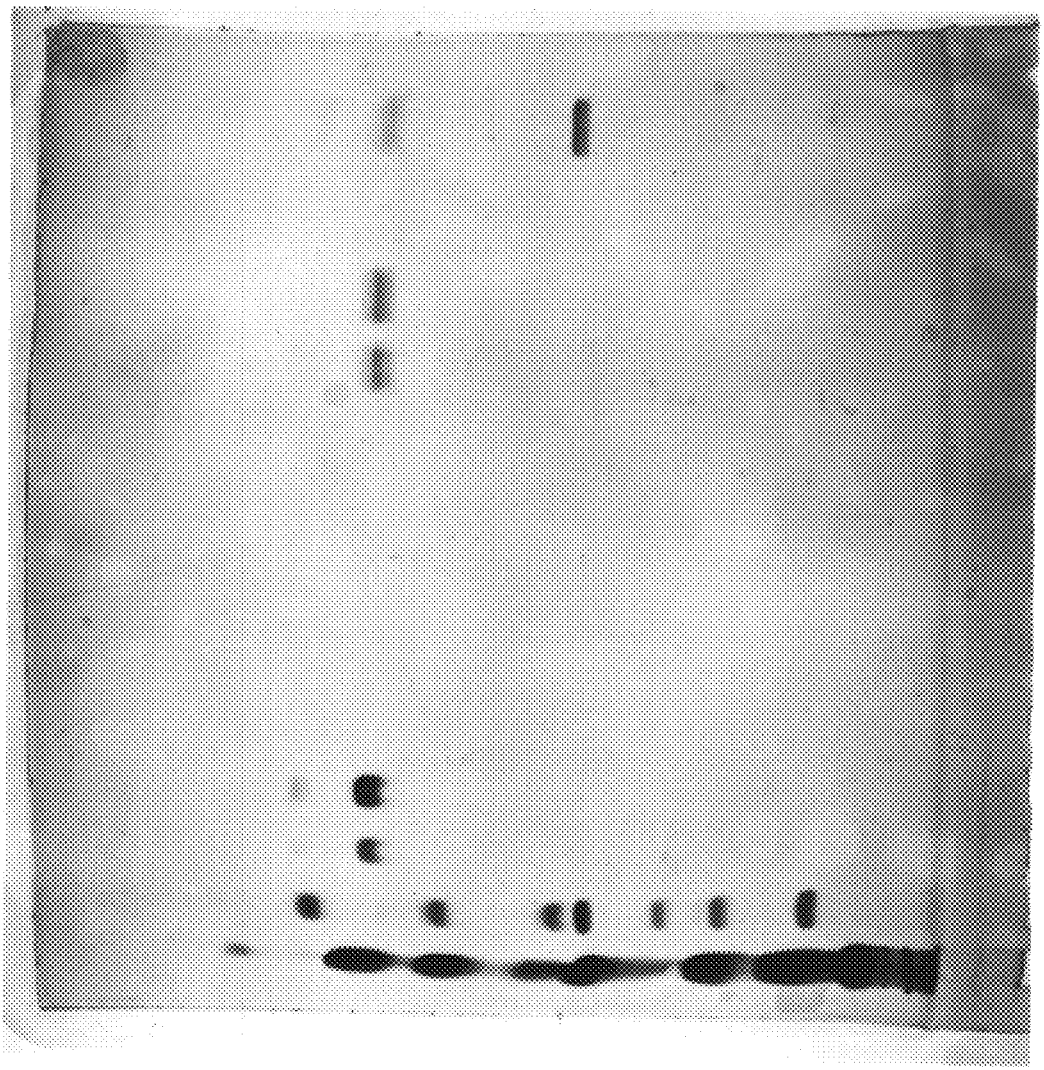
FIG. 26 depicts Coomassie Blue stained SDS-PAGE of the GDNF solution; prior to refolding (lanes 6 & 13), after refolding (lane 2), and after refolding and subsequent back reduction with 150 mM 2-mercaptoethanol (lane 5). The material prior to refolding and after back reduction runs as a monomer at about 16 kDa. GDNF after successful refolding runs (without reduction) as a dimer at about 30 kDa (see Example 6C). Lane 15 is molecular weight standards (SDS-70L, Sigma).

Analysis of Refolded GDNF by SDS-PAGE. GDNF extracted from bacteria without prior exposure to reducing agents migrates as a monomer on SDS-PAGE, at an apparent molecular weight of about 16 kDa compared to the migration of molecular weight standard proteins. There is no detectable GDNF at the position of a dimer. GDNF, exposed to reducing agent (30–150 mM 2-mercaptoethanol) either during extraction or just before SDS-PAGE but prior to refolding, migrates at a position indistinguishable from the non-reduced bacterial protein, with an apparent molecular weight of about 16 kDa (FIG. 26, lanes 6 & 13). This indicates that GDNF prepared from the bacterial cells is not dimerized prior to refolding.

After refolding as above, most of the bacterially-produced recombinant GDNF migrates on non-reducing SDS-PAGE as an apparent dimer at approximately 30 kDa (FIG. 26, lane 2). Reduction of the refolded GDNF with 150 mM 2-mercaptoethanol prior to SDS-PAGE causes it to again migrate at the position of the monomer at approximately 16 kDa (FIG. 23, lane 5). These results indicate that refolding of GDNF causes the protein to become a disulfide-bonded dimer. SDS-PAGE of refolded GDNF was run without reduction, and the gel sliced along its length and the slices assayed for bioactivity in the sympathetic ganglia neuron survival assay (see below). The only detectable bioactivity was at the position of the dimer, indicating that the dimer is biologically active.

Analysis of Refolded GDNF on Reversed-Phase HPLC (RP-HPLC). GDNF partially purified by S-Sepharose or Q-Sepharose chromatography, but prior to refolding, migrated on RP-HPLC, performed as indicated below, with a retention time of about 21 minutes. GDNF after refolding migrated under identical conditions with a retention time of about 15 minutes. A shift in retention time is expected for successful refolding of GDNF. It is often seen that a shift in retention times on RP-HPLC is observed after refolding of proteins.

RP-HPLC of these samples was performed as follows: at a flow rate of 1 ml/minute: A 0.46×25 cm C-4 column (VyDac #214TP54) was developed as follows: Solvent A=0.1% trifluoracetic acid (TFA) in water; Solvent B=0.1% TFA in acetonitrile; From 0.5 to 1.5 minutes, B is increased from 5% to 25%; From 1.5 to 31.5 minutes, B is increased from 25% to 55%.

Figure 27:
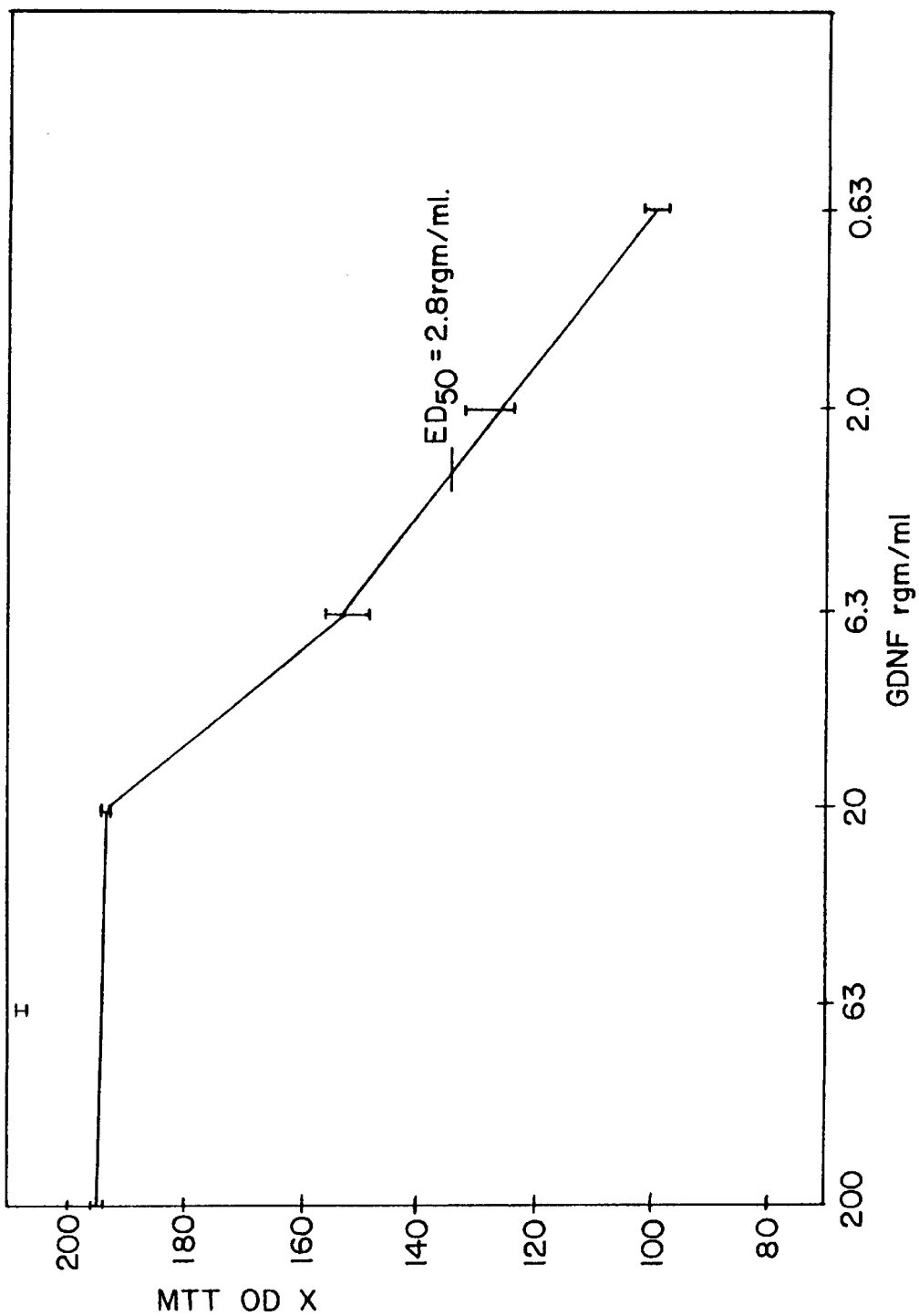
FIG. 27 depicts the results of a bioassay using refolded GDNF; measuring the ability to promote the survival of chick embryo sympathetic neurons in culture. The bioassay procedure is as described in Example 4A. Optical density (proportional to the number of surviving neurons) on the Y-axis is plotted against GDNF concentration on the X-axis (determined by laser-densitometry scanning of Coomassie Blue stained SDS-PAGE gels). The calculated ED50 of refolded GDNF for chick embryo sympathetic neuron survival is about 3 ng/ml.
Figure 28:
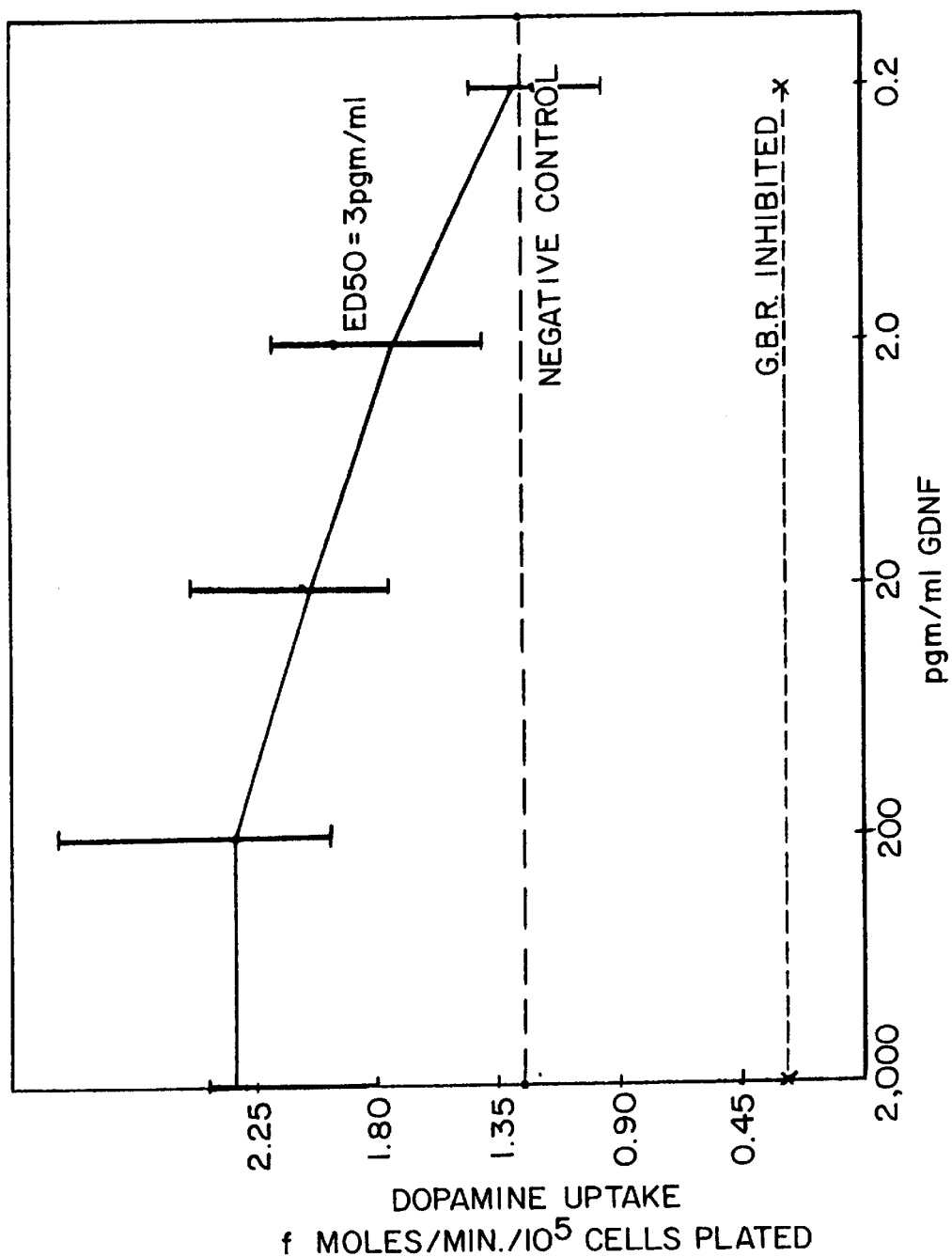
FIG. 28 depicts the results of a bioassay using refolded GDNF; measuring the ability to increase dopamine uptake by nigral dopaminergic neurons in cultures of rat embryonic mesencephalon. The bioassay procedure is as described in Example 1B. Dopamine uptake on the Y-axis is plotted against GDNF concentrations on the X-axis. The calculated ED50 of refolded GDNF for increasing dopamine uptake in these cultures is about 3 pg/ml.

Analysis of Refolded GDNF by Bioassays. Refolded GDNF was bioassayed in both the chick embryo (E10) sympathetic ganglia neuron survival bioassay (Example 4A) and the rat embryo (E16) mesencephalic culture dopamine uptake bioassay (Example 1B). Prior to refolding, GDNF, exposed to 30 mM 2-mercaptoethanol and purified by S-Sepharose or Q-Sepharose chromatography as above, exhibited no detectable bioactivity in the mesencephalic culture dopamine uptake assay and greatly reduced bioactivity in the sympathetic neuron survival bioassay. The apparent ED50 in the sympathetic neuron survival bioassay of S-Sepharose chromatographed material was about 1 $\mu$g/ml, which is about 333-fold lower than refolded rhGDNF (see below). For Q-Sepharose chromatographed material the apparent ED50 in the sympathetic neuron survival bioassay was about 3 $\mu$g/ml, which is about 100-fold lower than refolded rhGDNF (see below). After refolding, GDNF, with or without prior exposure to 2-mercaptoethanol, was apparently fully active in both bioassays (FIGS. 27–28). This result indicates that GDNF acquired significant bioactivity upon refolding and also that the reduced or absent bioactivity before refolding was not due to exposure to 2-mercaptoethanol.

The ED50 of refolded recombinant human GDNF (rhGDNF) in these bioassays was similar to that observed previously for rat GDNF purified from B49-cell conditioned medium. In the sympathetic neuron survival bioassay the ED50 for rhGDNF was about 3 ng/ml (FIG. 27) and the ED50 for rat GDNF was about 5 ng/ml. In the mesencephalic culture dopamine uptake assay, the ED50 for rhGDNF was about 30 pg/ml (FIG. 28) and for rat GDNF about 50 pg/ml. These results indicate that a substantial proportion of rhGDNF was successfully refolded and fully biologically active.

Example 7

Production and Isolation of Antibodies to GDNF

Antibodies to rhGDNF were generated by the following procedure. This procedure is seen to include but not be limited to this adjuvant, immunization protocol, and species of animal. Also, antibodies to GDNF may be raised using the refolded, native protein or the denatured, inactive protein as in the procedure given below or with contiguous peptides of the GDNF sequence from human or other animal species.

Monoclonal antibodies may be generated by one of many standard procedures (see *Antibodies, a laboratory manual;* Cold Spring Harbor Laboratory 1988 ISBN 087969-314-2 editor Ed Harlow and David Lane). In brief, such a procedure for generating monoclonal antibodies typically but not exclusively involves immunizing the appropriate animals and monitoring the antibody response of these animals to the immunizing protocol, isolating antibody producing cells such as from a lymphoid organ of one or more responsive animals, fusing these cells with an appropriate cell line such as myeloma cells to produce hybridomas that are antibody secreting immortal cells, and screening to progressively isolate hybridomas until single cell clones are obtained producing the desired monoclonal antibody.

Polyclonal antibodies in rabbits were raised as follows: Two milliters of sterile saline containing 0.005–0.25 mg rhGDNF were injected into a vial of the RIBI adjuvant MPL-TDM-CWS emulsion (RIBI ImmunoChem Research, Inc.) and vortexed to form an emulsion as per the manufacturer's instructions. Anesthetized female New Zealand white rabbits were injected following the suggested immunization protocol from RIBI. One milliliter of adjuvant antigen emulsion was administered as follows:

0.30 ml intradermal (0.05 ml in each of six sites)

0.40 ml intramuscular (0.20 ml into each hind leg)

0.10 ml subcutaneous (neck region)

0.20 ml intraperitoneal

The animals were injected again (boosted) every 4–6 weeks by the same protocol. Blood was drawn from the animals before the first injection and at 10–14 days after each boost to test for antibody production with a neutralization assay or a standard ELISA.

The neutralization assay was carried out as follows using the rat E16 mesencephalic culture assay. Rabbit test serum was diluted into Dulbecco's minimal essential medium buffered with 25 mM HEPES to pH7.4 containing 5 mg/ml of bovine serum albumin (referred to as BSA5). This in turn was added to the assay wells (25 μl of diluted test serum into 500 μl of tissue culture solution) and allowed to incubate at 37° for 30 minutes. Next rhGDNF was added as 25 μl of a stock diluted solution in BSA5 containing rhGDNF at 6.32 ngm/ml for a final rhGDNF concentration of 0.316 ngm/ml in the assay. Dopamine uptake was measured after eight days in culture by the previously described procedure. Results with antisera from the second boosts are shown below for the neutralization assay (Refer to Table 2 below).

TABLE 2

| Rabbit Number | Antigen | *Neut. $EC_{50}$ | +Elisa $EC_{50}$ |
|---|---|---|---|
| 1604 | refolded rhGDNF | $20 \times 10^3$ | $25 \times 10^3$ |
| 2257 | refolded rhGDNF | $12 \times 10^3$ | $7 \times 10^3$ |
| 2506 | refolded rhGDNF | $2 \times 10^3$ | $3 \times 10^3$ |
| 9380 | denatured rhGDNF | $2 \times 10^3$ | $2 \times 10^3$ |

*antiserum dilution for 50% neutralization of GDNF stimulated dopamine uptake
+antiserum dilution for 50% of the maximum (plateau) signal in ELISA The antisera were also titered for GDNF antibodies in a standard ELISA by the following procedure: Microtiter plates (96 well, Nunc maxisorp) were coated with 100 μl per well of rhGDNF at 1.0 μgm/ml in 50 mM sodium bicarbonate, pH9.6 coating buffer overnight at 4° C. The plates were washed four times with plate wash buffer (PWB; phosphate buffered physiological saline, pH7.2 containing 0.5% Tween 20) and then blocked for 2 hours at 25° C. with 200 μl per well of 2% bovine serum albumin in phosphate buffered physiological saline, pH7.2. The plates were washed again with PWB and serum samples to be titered (100 μl diluted in 20% normal goat serum and PWB) added to the wells. Plates were incubated for 1.5 hours at 35° C. and washed again with PWB. Alkaline phosphatase conjugated goat anti-rabbit IgG (Jackson Immunochemicals) at a 1:2500 dilution in PWB was added to each well (100 μl) and incubated for 1.5 hours at 35° C. The plates were washed with PWB as before. Next p-NPP substrate (disodium p-nitrophenyl phosphate; Sigma Cat. No. MP389) was added to each well (100 μl at 1.0 mg/ml p-NPP in 10% diethanolamine, pH9.8) and the plate incubated at 25° C. Color development was followed by reading the plates at 405–490 nm on a plate reader (Molecular Devices Enax).

Antisera were also used to detect and quantitate GDNF on Western Blots as follows: Sodium dodecyl sulfate polyacrylamide gel electrophoresis (SDS PAGE) was performed by the basic procedure first described by U.K. Laemmli (Nature 227:680–685 (1970)) using a 12½% acrylamide resolving gel and 4½% acrylamide stacking gel. Gels (16×14×0.15 cm) were electrophoresed at 40 m amp constant current for 3 hours. For reduction/denaturation, samples were heated at 100° C. for 10 minutes in sample buffer containing 1% SDS and 150 mM 2-mercaptoethanol.

For Western blotting, the gel was then transblotted onto Immobilon-P membrane (Millipore Cat. No. IPVH 151 50) at 80 m amp constant current for 16 hours in 25 mM Trisbase, 192 mM glycine, 0.1% SDS, and 20% methanol and processed as follows:

1) The membrane was blocked for one hour at 25° C. in blocking buffer (10 mM Tris, pH 7.4 containing 150 mM NaCl; 0.05% Tween 20; 4% skim milk; and 0.02% sodium azide) with gentle rocking.

2) The membrane was next incubated at 25° C. for 2 hours with gentle rocking in blocking buffer containing diluted primary antisera to GDNF.

3) The membrane was washed (4 5-minute washes) in blocking buffer.

4) The membrane was next incubated at 25° C. for 2 hours with gentle rocking in blocking buffer containing diluted secondary antibody (alkaline phosphatase conjugated affinity purified goat anti-rabbit IgG; Cappel Cat. No. 59299).

5) The membrane was washed (4 5-minute washes) with blocking buffer excluding the skim milk.

6) The membrane was developed in 50 ml of developing buffer (100 mM Tris, pH 9.5 containing 100 mM NaCl and 5 mM $MgCl_2$) with 165 μl of NBT and 83 μl of BCIP (Promega kit Cat No. P3771) at 25° C. with gentle rocking until the desired staining is achieved.

Example 8

Preparation of Membrane Encapsulated Cells that Secrete GDNF, and Implantation into Patient Cells that secrete GDNF may be encapsulated into semipermeable membranes for implantation into patients suffering from nerve damage. In a preferred embodiment, the patient is suffering from Parkinson's disease, and the encapsulated cells that secrete GDNF are implanted into the striatum of the patient to provide GDNF to the dopaminergic cell bodies.

In one embodiment of the invention, cells that have been engineered to secrete GDNF—such as those prepared and described in Examples 5 and 6 above—are incorporated into biocompatible, implantable, and retrievable polymeric inserts. The inserts may be designed so as to permit the secreted GDNF to enter into the tissue surrounding the implanted cells, while preventing factors from the surrounding tissue that would be detrimental to the cells from access to the cells.

The cells that have been engineered to secrete GDNF may be encapsulated into such semipermeable membranes according to the method described in published PCT application WO 91/10425, entitled Cell Capsule Extrusion Systems. The membrane encapsulated cells may be implanted into the striatum pursuant to standard surgical procedures.

What is claimed is:

1. An implantable device for the delivery of glial cell line-derived neurotrophic factor polypeptide comprising:
   a membrane; and
   cells transformed to express and secrete a glial cell line-derived neurotrophic factor polypeptide comprising an amino acid sequence of SEQ ID NO:4 or SEQ ID NO:6, wherein said cells are encapsulated within said membrane,
   said membrane being permeable to said glial cell line-derived neurotrophic factor polypeptide, and substantially impermeable to immune system materials which are detrimental to said cells.

2. The device of claim 1 wherein said cells are transformed to contain a heterologous expression regulatory element operatively linked to a nucleic acid sequence encoding said glial cell line-derived neurotrophic factor polypeptide.

3. The device of claim 1 wherein said glial cell line-derived neurotrophic factor polypeptide comprises an amino acid sequence as set forth in SEQ ID NO:6.

4. An implantable device for the delivery of glial cell line-derived neurotrophic factor polypeptide comprising:
   a membrane; and
   one or more cells encapsulated within said membrane, comprising cells transformed to express and secrete glial cell line-derived neurotrophic factor polypeptide,
   wherein said membrane is permeable to said glial cell line-derived neurotrophic factor polypeptide, and substantially impermeable to immune system materials which are detrimental to said cells, and
   wherein said glial cell line-derived neurotrophic factor polypeptide comprises an amino acid sequence which is in excess of 70% identical to an amino acid sequence set forth in SEQ ID NO:4 or SEQ ID NO:6 when four gaps in a length of 100 amino acids may be introduced to assist in that alignment, and wherein said glial cell line-derived neurotrophic factor polypeptide has the ability to promote the survival or function of nerve cells.

5. A device of claim 4 wherein said cells contain an expression regulatory element operatively linked to a nucleic acid sequence encoding said glial cell line-derived neurotrophic factor polypeptide.

6. A device of claim 4 wherein said glial cell line-derived neurotrophic factor polypeptide comprises an amino acid sequence which is in excess of 70% identical to an amino acid sequence of SEQ ID NO:6 when four gaps in a length of 100 amino acids may be introduced to assist in that alignment.

7. A device of claim 4 wherein said glial cell line-derived neurotrophic factor polypeptide comprises the amino acid sequence of SEQ ID NO:6.

8. A device for the delivery of glial cell line-derived neurotrophic factor polypeptide, comprising:
   a membrane; and
   cells contained within said membrane, wherein said cells are recombinantly modified to express and secrete a glial cell line-derived neurotrophic factor polypeptide comprising the amino acid sequence of SEQ ID NO:6, and
   wherein said membrane is permeable to said glial cell line-derived neurotrophic factor polypeptide and substantially impermeable to immune system materials which are detrimental to said cells.

9. An article for the delivery of glial cell line-derived neurotrophic factor polypeptide, comprising: one or more cells that have been transformed to express and secrete glial cell line-derived neurotrophic factor polypeptide wherein said glial cell line-derived neurotrophic factor polypeptide comprises an amino acid sequence set forth in SEQ ID NO:4 or SEQ ID NO:6 or a polypeptide which is in excess of 70% identical to an amino acid sequence set forth in SEQ ID NO:4 or SEQ ID NO:6 when four gaps in a length of 100 amino acids may be introduced to assist in that alignment, and wherein said glial cell line-derived neurotrophic factor polypeptide has the ability to promote the survival or function of nerve cells.

10. An article of claim 9 further comprising an implantable membrane in which said one or more cells are contained wherein said membrane is substantially impermeable to immune system materials which are detrimental to said cells.

11. An article of claim 9 wherein said polypeptide is in excess of 70% identical to the amino acid sequence of SEQ ID NO:6 when four gaps in a length of 100 amino acids may be introduced to assist in that alignment.

12. An article for the delivery of glial cell line-derived neurotrophic factor polypeptide, comprising: cells transformed to express and secrete glial cell line-derived neurotrophic factor polypeptide comprising the amino acid sequence of SEQ ID NO:6 wherein said cells are suitable for implantation.

13. An article of claim 12 further comprising an implantable membrane in which said cells are contained, wherein said membrane is substantially impermeable to immune system materials which are detrimental to said cells.

14. An article of claim 12 further comprising an implantable polymeric membrane in which said cells are contained, wherein said membrane is substantially impermeable to immune system materials which are detrimental to said cells.

15. An article of claim 12 wherein said cells are human cells.

16. An article of claim 12 wherein said cells are suitable for implantation in the central nervous system.

17. A method of delivering glial derived neurotrophic factor polypeptide comprising implanting an article of claim 12.

18. A device of claim 8 wherein said membrane is a polymeric membrane.

19. A device of claim 8 wherein said cells are human cells.

20. A device of claim 8 suitable for implantation in the central nervous system.

* * * * *

UNITED STATES PATENT AND TRADEMARK OFFICE
CERTIFICATE OF CORRECTION

PATENT NO.    : 6,221,376 B1
DATED         : April 24, 2001
INVENTOR(S)   : Lin et al.

It is certified that error appears in the above-identified patent and that said Letters Patent is hereby corrected as shown below:

Column 10,
Line 28, change "diners" to -- dimers --.

Column 22,
Line 38, change "HEM" to -- MEM --.

Column 28,
Line 59, change "tinkered" to -- linked --.

Column 32,
Line 46, change "a" to -- 8 --.

Column 42,
Line 29, change "20° C." to -- -20° C. --

Signed and Sealed this

Sixteenth Day of October, 2001

Attest:

*Attesting Officer*

NICHOLAS P. GODICI
*Acting Director of the United States Patent and Trademark Office*

SEQUENCE LISTING (1) GENERAL INFORMATION:

(iii) NUMBER OF SEQUENCES: 26

(2) INFORMATION FOR SEQ ID NO:1:

(i) SEQUENCE CHARACTERISTICS:
       (A) LENGTH: 25 amino acids
       (B) TYPE: amino acid
       (D) TOPOLOGY: linear (v) FRAGMENT TYPE: N-terminal fragment (xi) SEQUENCE DESCRIPTION:   SEQ ID NO:1:

Ser Pro Asp Lys Gln Ala Ala Ala Leu Pro Arg Arg Glu Arg Asn Xaa
                 5                  10                  15
Gln Ala Ala Ala Ala Ser Pro Asp Asn
             20                  25

(2) INFORMATION FOR SEQ ID NO:2:

(i) SEQUENCE CHARACTERISTICS:
       (A) LENGTH:   13 amino acids
       (B) TYPE:     amino acid
       (C) TOPOLOGY: linear (v) FRAGMENT TYPE: internal fragment (ix) FEATURE:
       (D) OTHER INFORMATION: Xaa is either Lys or Gln (xi) SEQUENCE DESCRIPTION: SEQ ID NO:2:

Asp Xaa Ile Leu Lys Asn Leu Gly Arg Val Arg Arg Leu
                 5                  10

(2) INFORMATION FOR SEQ ID NO:3:

(i) SEQUENCE CHARACTERISTICS:
       (A) LENGTH: 900 base pairs
       (B) TYPE: nucleic acid
       (C) STRANDEDNESS: single
       (D) TOPOLOGY: linear (ix) FEATURE:
       (A) NAME/KEY: nucleic acid for rat GDNF (xi) SEQUENCE DESCRIPTION: SEQ ID NO:3:

```
CCCCCGGGCT GCAGGAATTC GGGG GTC TAC GGA GAC CGG ATC CGA GGT           48
                           Val Tyr Gly Asp Arg Ile Arg Gly
                                             -90

GCC GCC GCC GGA CGG GAC TCT AAG ATG AAG TTA TGG GAT GTC GTG          93
Ala Ala Ala Gly Arg Asp Ser Lys Met Lys Leu Trp Asp Val Val
-85                 -80                 -75

GCT GTC TGC CTG GTG TTG CTG CAC ACC GCG TCT GCC TTC CCG CTG         138
Ala Val Cys Leu Val Leu Leu His Thr Ala Ser Ala Phe Pro Leu
-70                 -65                 -60

CCC GCC GGT AAG AGG CTT CTC GAA GCG CCC GCC GAA GAC CAC TCC         183
Pro Ala Gly Lys Arg Leu Leu Glu Ala Pro Ala Glu Asp His Ser
-55                 -50                 -45

CTC GGC CAC CGC CGC GTG CCC TTC GCG CTG ACC AGT GAC TCC AAT         228
Leu Gly His Arg Arg Val Pro Phe Ala Leu Thr Ser Asp Ser Asn
-40                 -35                 -30

ATG CCC GAA GAT TAT CCT GAC CAG TTT GAT GAC GTC ATG GAT TTT         273
Met Pro Glu Asp Tyr Pro Asp Gln Phe Asp Asp Val Met Asp Phe
-25                 -20                 -15
```

```
ATT CAA GCC ACC ATC AAA AGA CTG AAA AGG TCA CCA GAT AAA CAA          318
Ile Gln Ala Thr Ile Lys Arg Leu Lys Arg Ser Pro Asp Lys Gln
-10              -5                   1                   5

GCG GCG GCA CTT CCT CGA AGA GAG AGG AAC CGG CAA GCT GCA GCT          363
Ala Ala Ala Leu Pro Arg Arg Glu Arg Asn Arg Gln Ala Ala Ala
                 10                  15                  20

GCC AGC CCA GAG AAT TCC AGA GGG AAA GGT CGC AGA GGC CAG AGG          408
Ala Ser Pro Glu Asn Ser Arg Gly Lys Gly Arg Arg Gly Gln Arg
                25                  30                  35

GGC AAA AAT CGG GGG TGC GTC TTA ACT GCA ATA CAC TTA AAT GTC          453
Gly Lys Asn Arg Gly Cys Val Leu Thr Ala Ile His Leu Asn Val
                 40                  45                  50

ACT GAC TTG GGT TTG GGC TAC GAA ACC AAG GAG GAA CTG ATC TTT          498
Thr Asp Leu Gly Leu Gly Tyr Glu Thr Lys Glu Glu Leu Ile Phe
                55                  60                  65

CGA TAT TGT AGC GGT TCC TGT GAA GCG GCC GAG ACA ATG TAC GAC          543
Arg Tyr Cys Ser Gly Ser Cys Glu Ala Ala Glu Thr Met Tyr Asp
                70                  75                  80

AAA ATA CTA AAA AAT CTG TCT CGA AGT AGA AGG CTA ACA AGT GAC          588
Lys Ile Leu Lys Asn Leu Ser Arg Ser Arg Arg Leu Thr Ser Asp
                85                  90                  95

AAG GTA GGC CAG GCA TGT TGC AGG CCG GTC GCC TTC GAC GAC GAC          633
Lys Val Gly Gln Ala Cys Cys Arg Pro Val Ala Phe Asp Asp Asp
                100                 105                 110

CTG TCG TTT TTA GAC GAC AGC CTG GTT TAC CAT ATC CTA AGA AAG          678
Leu Ser Phe Leu Asp Asp Ser Leu Val Tyr His Ile Leu Arg Lys
                115                 120                 125

CAT TCC GCT AAA CGG TGT GGA TGT ATC TGA CCCTGGCTCC                   718
His Ser Ala Lys Arg Cys Gly Cys Ile
                130

AGAGACTGCT GTGTATTGCA TTCCTGCTAC ACTGCGAAGA AAGGGACCAA               768

GGTTCCCAGG AAATATTTGC CCAGAAAGGA AGATAAGGAC CAAGAAGGCA               818

GAGGCAGAGG CGGAAGAAGA AGAAGAAAAG AAGGACGAAG GCAGCCATCT               868

GTGGGAGCCT GTAGAAGGAG GCCCAGCTAC AG                                  900

(2) INFORMATION FOR SEQ ID NO:4:

(i) SEQUENCE CHARACTERISTICS:
        (A) LENGTH: 134 amino acid residues
        (B) TYPE: amino acid
        (D) TOPOLOGY: linear (ix) FEATURE:
        (A) NAME/KEY: inferred amino acid sequence for mature
            rat GDNF (xi) SEQUENCE DESCRIPTION: SEQ ID NO:4:

Ser Pro Asp Lys Gln Ala Ala Ala Leu Pro Arg Arg Glu Arg Asn Arg
1               5                   10                  15

Gln Ala Ala Ala Ser Pro Glu Asn Ser Arg Gly Lys Gly Arg Arg
            20                  25                  30

Gly Gln Arg Gly Lys Asn Arg Gly Cys Val Leu Thr Ala Ile His Leu
        35                  40                  45

Asn Val Thr Asp Leu Gly Leu Gly Tyr Glu Thr Lys Glu Glu Leu Ile
    50                  55                  60

Phe Arg Tyr Cys Ser Gly Ser Cys Glu Ala Ala Glu Thr Met Tyr Asp
65                  70                  75                  80
```

```
Lys Ile Leu Lys Asn Leu Ser Arg Ser Arg Arg Leu Thr Ser Asp Lys
            85                  90                  95

Val Gly Gln Ala Cys Cys Arg Pro Val Ala Phe Asp Asp Asp Leu Ser
        100                 105                 110

Phe Leu Asp Asp Ser Leu Val Tyr His Ile Leu Arg Lys His Ser Ala
        115                 120                 125

Lys Arg Cys Gly Cys Ile
        130
```

(2) INFORMATION FOR SEQ ID NO:5:

(i) SEQUENCE CHARACTERISTICS:
        (A) LENGTH: 562 base pairs
        (B) TYPE: nucleic acid
        (C) STRANDEDNESS: single
        (D) TOPOLOGY: linear (ix) FEATURE:
        (A) NAME/KEY: nucleic acid sequence for human GDNF (xi) SEQUENCE DESCRIPTION: SEQ ID NO:5:

```
ATTT TCTCTTTTCT TTTTGAACAG CA AAT ATG CCA GAG GAT TAT CCT           47
                              Ser Asn Met Pro Glu Asp Tyr Pro
                                      -25                 -20

GAT CAG TTC GAT GAT GTC ATG GAT TTT ATT CAA GCC ACC ATT            89
Asp Gln Phe Asp Asp Val Met Asp Phe Ile Gln Ala Thr Ile
            -15                 -10

AAA AGA CTG AAA AGG TCA CCA GAT AAA CAA ATG GCA GTG CTT           131
Lys Arg Leu Lys Arg Ser Pro Asp Lys Gln Met Ala Val Leu
-5                   1               5

CCT AGA AGA GAG CGG AAT CGG CAG GCT GCA GCT GCC AAC CCA           173
Pro Arg Arg Glu Arg Asn Arg Gln Ala Ala Ala Ala Asn Pro
10                  15                  20

GAG AAT TCC AGA GGA AAA GGT CGG AGA GGC CAG AGG GGC AAA           215
Glu Asn Ser Arg Gly Lys Gly Arg Arg Gly Gln Arg Gly Lys
        25                  30                  35

AAC CGG GGT TGT GTC TTA ACT GCA ATA CAT TTA AAT GTC ACT           257
Asn Arg Gly Cys Val Leu Thr Ala Ile His Leu Asn Val Thr
        40                  45                  50

GAC TTG GGT CTG GGC TAT GAA ACC AAG GAG GAA CTG ATT TTT           299
Asp Leu Gly Leu Gly Tyr Glu Thr Lys Glu Glu Leu Ile Phe
        55                  60                      65

AGG TAC TGC AGC GGC TCT TGC GAT GCA GCT GAG ACA ACG TAC           341
Arg Tyr Cys Ser Gly Ser Cys Asp Ala Ala Glu Thr Thr Tyr
                70                  75

GAC AAA ATA TTG AAA AAC TTA TCC AGA AAT AGA AGG CTG GTG           383
Asp Lys Ile Leu Lys Asn Leu Ser Arg Asn Arg Arg Leu Val
80              85                  90

ACT GAC AAA GTA GGG CAG GCA TGT TGC AGA CCC ATC GCC TTT           425
Ser Asp Lys Val Gly Gln Ala Cys Cys Arg Pro Ile Ala Phe
95                  100                 105

GAT GAT GAC CTG TCG TTT TTA GAT GAT AAC CTG GTT TAC CAT           467
Asp Asp Asp Leu Ser Phe Leu Asp Asp Asn Leu Val Tyr His
        110                 115                 120

ATT CTA AGA AAG CAT TCC GCT AAA AGG TGT GGA TGT ATC TGA           509
Ile Leu Arg Lys His Ser Ala Lys Arg Cys Gly Cys Ile
                125                 130

CTCCGGCTCC AGAGACTGCT GTGTATTGCA TTCCTGCTAC AGTGCAAAGA            559

AAG                                                               562
```

(2) INFORMATION FOR SEQ ID NO:6:

(i) SEQUENCE CHARACTERISTICS:
        (A) LENGTH: 134 amino acid residues
        (B) TYPE: amino acid
        (D) TOPOLOGY: linear (ix) FEATURE:
        (A) NAME/KEY: inferred amino acid sequence for mature
            human GDNF (xi) SEQUENCE DESCRIPTION: SEQ ID NO:6:

```
Ser Pro Asp Lys Gln Met Ala Val Leu Pro Arg Arg Glu Arg Asn Arg
 1               5                  10                  15

Gln Ala Ala Ala Asn Pro Glu Asn Ser Arg Gly Lys Gly Arg Arg
            20                  25                  30

Gly Gln Arg Gly Lys Asn Arg Gly Cys Val Leu Thr Ala Ile His Leu
            35                  40                  45

Asn Val Thr Asp Leu Gly Leu Gly Tyr Glu Thr Lys Glu Glu Leu Ile
            50                  55                  60

Phe Arg Tyr Cys Ser Gly Ser Cys Asp Ala Ala Glu Thr Thr Tyr Asp
65                  70                  75                  80

Lys Ile Leu Lys Asn Leu Ser Arg Asn Arg Arg Leu Val Ser Asp Lys
                85                  90                  95

Val Gly Gln Ala Cys Cys Arg Pro Ile Ala Phe Asp Asp Leu Ser
            100                 105                 110

Phe Leu Asp Asp Asn Leu Val Tyr His Ile Leu Arg Lys His Ser Ala
            115                 120                 125

Lys Arg Cys Gly Cys Ile
            130
```

(2) INFORMATION FOR SEQ ID NO:7:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ix) FEATURE:
        (A) NAME/KEY: oligonucleotide probe
        (D) OTHER INFORMATION: N at positions 3, 15, and 18 is
            inosine (xi) SEQUENCE DESCRIPTION: SEQ ID NO:7:

```
CCNGAYAARC ARGCNGCNGC                                          20
```

(2) INFORMATION FOR SEQ ID NO:8:

(i) SEQUENCE CHARACTERISTICS:
        (A) LENGTH: 223 base pairs
        (B) TYPE: nucleic acid
        (C) STRANDEDNESS: single
        (D) TOPOLOGY: linear (ix) FEATURE:
        (A) NAME/KEY: nucleic acid sequence for human GDNF (xi) SEQUENCE DESCRIPTION: SEQ ID NO:8:

```
TTCTCTCCCC CACCTCCCGC CTGCCCGCGC A GGT GCC GCC GCC GGA         46
                                 Gly Ala Ala Ala Gly
                                                -5

CGG GAC TTT AAG ATG AAG TTA TGG GAT GTC GTG GCT GTC TGC        88
Arg Asp Phe Lys Met Lys Leu Trp Asp Val Val Ala Val Cys
         1               5                  10
```

```
CTG GTG CTG CTC CAC ACC GCG TCC GCC TTC CCG CTG CCC GCC           130
Leu Val Leu Leu His Thr Ala Ser Ala Phe Pro Leu Pro Ala
             15                  20

GGT AAG AGG CCT CCC GAG GCG CCC GCC GAA GAC CGC TCC CTC           172
Gly Lys Arg Pro Pro Glu Ala Pro Ala Glu Asp Arg Ser Leu
 25                  30                  35

GGC CGC CGC CGC GCG CCC TTC GCG CTG AGC AGT GAC T                 209
Gly Arg Arg Arg Ala Pro Phe Ala Leu Ser Ser Asp
     40                  45                  50

GTAAGAACCG TTCC                                                   223
```

(2) INFORMATION FOR SEQ ID NO:9:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ix) FEATURE:
        (A) NAME/KEY: linker (xi) SEQUENCE DESCRIPTION: SEQ ID NO:9:

```
CCCGAATTCG GG                                                      12
```

(2) INFORMATION FOR SEQ ID NO:10:

(i) SEQUENCE CHARACTERISTICS:
        (A) LENGTH: 7 amino acid residues
        (B) TYPE: amino acid
        (D) TOPOLOGY: linear (xi) SEQUENCE DESCRIPTION: SEQ ID NO:10:

```
Pro Asp Lys Gln Ala Ala Ala
                 5
```

(2) INFORMATION FOR SEQ ID NO:11:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ix) FEATURE:
        (A) NAME/KEY: nucleic acid sequence from pBluescript
            SK-76.1

(xi) SEQUENCE DESCRIPTION: SEQ ID NO:11:

```
GAGAGGAACC GGCAAGCTGC WGMWGYMWGM CCW                               33
```

(2) INFORMATION FOR SEQ ID NO:12:

(i) SEQUENCE CHARACTERISTICS:
        (A) LENGTH: 11 amino acid residues
        (B) TYPE: amino acid
        (D) TOPOLOGY: linear (xi) SEQUENCE DESCRIPTION: SEQ ID NO:12:

```
Glu Arg Asn Arg Gln Ala Ala Ala Ala Ser Pro
                 5                  10
```

(2) INFORMATION FOR SEQ ID NO:13:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ix) FEATURE:
        (A) NAME/KEY: oligonucleotide DHD-26
        (D) OTHER INFORMATION: N at positions 9 and 12 are
            inosine (xi) SEQUENCE DESCRIPTION: SEQ ID NO:13:

ARRTTYTTNA RNATYTTRTC                                           20

(2) INFORMATION FOR SEQ ID NO:14:

(i) SEQUENCE CHARACTERISTICS:
        (A) LENGTH: 7 amino acid residues
        (B) TYPE: amino acid
        (D) TOPOLOGY: linear (xi) SEQUENCE DESCRIPTION: SEQ ID NO:14:

Asp Lys Ile Leu Lys Asn Leu
                5

(2) INFORMATION FOR SEQ ID NO:15:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ix) FEATURE:
        (A) NAME/KEY: oligonucleotide primer PD1

(xi) SEQUENCE DESCRIPTION: SEQ ID NO:15:

GACGGGACTC TAAGATG                                              17

(2) INFORMATION FOR SEQ ID NO:16:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ix) FEATURE:
        (A) NAME/KEY: oligonucleotide primer DHD23
        (D) OTHER INFORMATION: N at positions 3, 6, and 18 is
            inosine (xi) SEQUENCE DESCRIPTION: SEQ ID NO:16:

GCNGCNGCYT GYTTRTCNGG                                           20

(2) INFORMATION FOR SEQ ID NO:17:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ix) FEATURE:
              (A) NAME/KEY: oligonucleotide primer LF2

(xi) SEQUENCE DESCRIPTION: SEQ ID NO:17:

CGAGACAATG TACGACA                                                    17

(2) INFORMATION FOR SEQ ID NO:18:

(i) SEQUENCE CHARACTERISTICS:
              (A) LENGTH: 17 base pairs
              (B) TYPE: nucleic acid
              (C) STRANDEDNESS: single
              (D) TOPOLOGY: linear (ix) FEATURE:
              (A) NAME/KEY: oligonucleotide primer PD2

(xi) SEQUENCE DESCRIPTION: SEQ ID NO:18:

CTCTGGAGCC AGGGTCA                                                    17

(2) INFORMATION FOR SEQ ID NO:19:

(i) SEQUENCE CHARACTERISTICS:
              (A) LENGTH: 26 base pairs
              (B) TYPE: nucleic acid
              (C) STRANDEDNESS: single
              (D) TOPOLOGY: linear (ix) FEATURE:
              (A) NAME/KEY: oligonucleotide primer PD1

(xi) SEQUENCE DESCRIPTION: SEQ ID NO:19:

CCCGAATTCG ACGGGACTCT AAGATG                                          26

(2) INFORMATION FOR SEQ ID NO:20:

(i) SEQUENCE CHARACTERISTICS:
              (A) LENGTH: 24 base pairs
              (B) TYPE: nucleic acid
              (C) STRANDEDNESS: single
              (D) TOPOLOGY: linear (ix) FEATURE:
              (A) NAME/KEY: oligonucleotide primer LFA (xi) SEQUENCE DESCRIPTION: SEQ ID NO:20:

CGGTGGCCAG AGGGAGTGGT CTTC                                            24

(2) INFORMATION FOR SEQ ID NO:21:

(i) SEQUENCE CHARACTERISTICS:
              (A) LENGTH: 46 base pairs
              (B) TYPE: nucleic acid
              (C) STRANDEDNESS: single
              (D) TOPOLOGY: linear (ix) FEATURE:
              (A) NAME/KEY: oligonucleotide primer PD3

(xi) SEQUENCE DESCRIPTION: SEQ ID NO:21:

CGCGGATCCA ATAAGGAGGA AAAAAAATGT CACCAGATAA ACAAAT                    46

(2) INFORMATION FOR SEQ ID NO:22:

(i) SEQUENCE CHARACTERISTICS:
              (A) LENGTH: 26 base pairs
              (B) TYPE: nucleic acid

```
            (C) STRANDEDNESS: single
            (D) TOPOLOGY: linear (ix) FEATURE:
            (A) NAME/KEY: oligonucleotide primer PD4

(xi) SEQUENCE DESCRIPTION: SEQ ID NO:22:

CGCGGTACCC AGTCTCTGGA GCCGGA                                              26

(2) INFORMATION FOR SEQ ID NO:23:

(i) SEQUENCE CHARACTERISTICS:
            (A) LENGTH: 33 base pairs
            (B) TYPE: nucleic acid
            (C) STRANDEDNESS: double
            (D) TOPOLOGY: linear (ix) FEATURE:
            (A) NAME/KEY: adapter fragment for plasmid pCJ1

(xi) SEQUENCE DESCRIPTION: SEQ ID NO:23:

GATCTAGAAT TGTCATGTTT GACAGCTTAT CAT                                      33

(2) INFORMATION FOR SEQ ID NO:24:

(i) SEQUENCE CHARACTERISTICS:
            (A) LENGTH: 37 base pairs
            (B) TYPE: nucleic acid
            (C) STRANDEDNESS: double
            (D) TOPOLOGY: linear (ix) FEATURE:
            (A) NAME/KEY: polylinker sequence for plasmid pCJX1-1

(xi) SEQUENCE DESCRIPTION: SEQ ID NO:24:

AATTCCCGGG TACCAGATCT GAGCTCACTA GTCTGCA                                  37

(2) INFORMATION FOR SEQ ID NO:25:

(i) SEQUENCE CHARACTERISTICS:
            (A) LENGTH: 747 base pairs
            (B) TYPE: nucleic acid
            (C) STRANDEDNESS: single
            (D) TOPOLOGY: linear (ix) FEATURE:
            (A) NAME/KEY: nucleic acid sequence for human GDNF (xi) SEQUENCE DESCRIPTION: SEQ ID NO:25:

TTCTCTCCCC CACCTCCCGC CTGCCCGCGC A GGT GCC GCC GCC GGA                    46
                                  Gly Ala Ala Ala Gly
                                              -85

CGG GAC TTT AAG ATG AAG TTA TGG GAT GTC GTG GCT GTC TGC                    88
Arg Asp Phe Lys Met Lys Leu Trp Asp Val Val Ala Val Cys
-80                 -75                 -70

CTG GTG CTG CTC CAC ACC GCG TCC GCC TTC CCG CTG CCC GCC                   130
Leu Val Leu Leu His Thr Ala Ser Ala Phe Pro Leu Pro Ala
        -65                 -60                 -55

GGT AAG AGG CCT CCC GAG GCG CCC GCC GAA GAC CGC TCC CTC                   172
Gly Lys Arg Pro Pro Glu Ala Pro Ala Glu Asp Arg Ser Leu
            -50                 -45                 -40

GGC CGC CGC CGC GCG CCC TTC GCG CTG AGC AGT GAC TCA AAT                   214
Gly Arg Arg Arg Ala Pro Phe Ala Leu Ser Ser Asp Ser Asn
                -35                 -30

ATG CCA GAG GAT TAT CCT GAT CAG TTC GAT GAT GTC ATG GAT                   256
Met Pro Glu Asp Tyr Pro Asp Gln Phe Asp Asp Val Met Asp
-25                 -20                 -15
```

```
TTT ATT CAA GCC ACC ATT AAA AGA CTG AAA AGG TCA CCA GAT              298
Phe Ile Gln Ala Thr Ile Lys Arg Leu Lys Arg Ser Pro Asp
    -10              -5                   -1   1

AAA CAA ATG GCA GTG CTT CCT AGA AGA GAG CGG AAT CGG CAG              340
Lys Gln Met Ala Val Leu Pro Arg Arg Glu Arg Asn Arg Gln
    5                   10                  15

GCT GCA GCT GCC AAC CCA GAG AAT TCC AGA GGA AAA GGT CGG              382
Ala Ala Ala Ala Asn Pro Glu Asn Ser Arg Gly Lys Gly Arg
            20                  25                  30

AGA GGC CAG AGG GGC AAA AAC CGG GGT TGT GTC TTA ACT GCA              424
Arg Gly Gln Arg Gly Lys Asn Arg Gly Cys Val Leu Thr Ala
                35                  40                  45

ATA CAT TTA AAT GTC ACT GAC TTG GGT CTG GGC TAT GAA ACC              466
Ile His Leu Asn Val Thr Asp Leu Gly Leu Gly Tyr Glu Thr
                    50                  55

AAG GAG GAA CTG ATT TTT AGG TAC TGC AGC GGC TCT TGC GAT              508
Lys Glu Glu Leu Ile Phe Arg Tyr Cys Ser Gly Ser Cys Asp
60                  65                  70

GCA GCT GAG ACA ACG TAC GAC AAA ATA TTG AAA AAC TTA TCC              550
Ala Ala Glu Thr Thr Tyr Asp Lys Ile Leu Lys Asn Leu Ser
    75                  80                  85

AGA AAT AGA AGG CTG GTG ACT GAC AAA GTA GGG CAG GCA TGT              592
Arg Asn Arg Arg Leu Val Ser Asp Lys Val Gly Gln Ala Cys
            90                  95                  100

TGC AGA CCC ATC GCC TTT GAT GAT GAC CTG TCG TTT TTA GAT              634
Cys Arg Pro Ile Ala Phe Asp Asp Asp Leu Ser Phe Leu Asp
                105                 110                 115

GAT AAC CTG GTT TAC CAT ATT CTA AGA AAG CAT TCC GCT AAA              676
Asp Asn Leu Val Tyr His Ile Leu Arg Lys His Ser Ala Lys
                    120                 125

AGG TGT GGA TGT ATC TGA CTCCGGCTCC AGAGACTGCT GTGTATTGCA             724
Arg Cys Gly Cys Ile
130

TTCCTGCTAC AGTGCAAAGA AAG                                            747

(2) INFORMATION FOR SEQ ID NO:26:

(i) SEQUENCE CHARACTERISTICS:
        (A) LENGTH:    220 amino acids
        (B) TYPE:      amino acid
        (C) TOPOLOGY:  linear (xi) SEQUENCE DESCRIPTION: SEQ ID NO:26:

Gly Ala Ala Ala Gly
                5

Arg Asp Phe Lys Met Lys Leu Trp Asp Val Ala Val Cys
                10                  15

Leu Val Leu Leu His Thr Ala Ser Ala Phe Pro Leu Pro Ala
20                  25                  30

Gly Lys Arg Pro Pro Glu Ala Pro Ala Glu Asp Arg Ser Leu
    35                  40                  45

Gly Arg Arg Arg Ala Pro Phe Ala Leu Ser Ser Asp Ser Asn
        50                  55                  60

Met Pro Glu Asp Tyr Pro Asp Gln Phe Asp Asp Val Met Asp
                65                  70                  75

Phe Ile Gln Ala Thr Ile Lys Arg Leu Lys Arg Ser Pro Asp
                    80                  85
```

```
Lys Gln Met Ala Val Leu Pro Arg Arg Glu Arg Asn Arg Gln
 90              95                 100

Ala Ala Ala Ala Asn Pro Glu Asn Ser Arg Gly Lys Gly Arg
    105                 110             115

Arg Gly Gln Arg Gly Lys Asn Arg Gly Cys Val Leu Thr Ala
        120             125                 130

Ile His Leu Asn Val Thr Asp Leu Gly Leu Gly Tyr Glu Thr
            135             140                 145

Lys Glu Glu Leu Ile Phe Arg Tyr Cys Ser Gly Ser Cys Asp
                150             155

Ala Ala Glu Thr Thr Tyr Asp Lys Ile Leu Lys Asn Leu Ser
160             165             170

Arg Asn Arg Arg Leu Val Ser Asp Lys Val Gly Gln Ala Cys
    175             180             185

Cys Arg Pro Ile Ala Phe Asp Asp Leu Ser Phe Leu Asp
        190             195             200

Asp Asn Leu Val Tyr His Ile Leu Arg Lys His Ser Ala Lys
            205             210             215

Arg Cys Gly Cys Ile
            220
```